(12) United States Patent
Shihadeh et al.

(10) Patent No.: US 10,036,043 B2
(45) Date of Patent: Jul. 31, 2018

(54) PROCESSES FOR PRODUCING ETHANOL AND YEAST

(71) Applicants: Novozymes A/S, Bagsvaerd (DK); MICROBIOGEN PTY. LTD, Sdyney, New South Wales (AU)

(72) Inventors: Katie Shihadeh, Raleigh, NC (US); Jeremy Saunders, Raleigh, NC (US); Joyce Craig, Pittsboro, NC (US); Mark Stevens, Kittrell, NC (US); Jennifer Headman, Franklinton, NC (US); Bernardo Vidal, Jr., Wake Forest, NC (US); John Matthews, Louisburg, NC (US); Suzanne Clark, Youngsville, NC (US); Paul Victor Attfield, Sydney (AU); Phillip John Livingstone Bell, Sydney (AU); Michael Akerman, Wake Forest, NC (US)

(73) Assignees: Novozymes A/S, Bagsvaerd (DK); Microbiogen Pty. Ltd., Sydney (AU)

( * ) Notice: Subject to any disclaimer, the term of this patent is extended or adjusted under 35 U.S.C. 154(b) by 0 days.

(21) Appl. No.: 15/127,748

(22) PCT Filed: Mar. 20, 2015

(86) PCT No.: PCT/US2015/021754
§ 371 (c)(1),
(2) Date: Sep. 20, 2016

(87) PCT Pub. No.: WO2015/143324
PCT Pub. Date: Sep. 24, 2015

(65) Prior Publication Data
US 2017/0166934 A1    Jun. 15, 2017

Related U.S. Application Data

(60) Provisional application No. 62/093,852, filed on Dec. 18, 2014, provisional application No. 62/078,198, filed on Nov. 11, 2014, provisional application No. 62/021,276, filed on Jul. 7, 2014.

(30) Foreign Application Priority Data

Mar. 21, 2014 (AU) ................................. 2014901009

(51) Int. Cl.
*C12P 7/06* (2006.01)
*C12P 7/14* (2006.01)
*C12R 1/865* (2006.01)
*C12N 1/18* (2006.01)
*C12C 11/09* (2006.01)

(52) U.S. Cl.
CPC ................ *C12P 7/14* (2013.01); *C12C 11/09* (2013.01); *C12N 1/18* (2013.01); *C12R 1/865* (2013.01)

(58) Field of Classification Search
CPC .................................. C12P 7/06; C12R 1/865
USPC .......................................................... 435/161
See application file for complete search history.

(56) References Cited

U.S. PATENT DOCUMENTS

2017/0145443 A1* 5/2017 Shihadeh .................. C12P 7/06

FOREIGN PATENT DOCUMENTS

EP        2 277 989 A1    7/2009
WO       2011035392 A1    3/2011

OTHER PUBLICATIONS

Hahn-Hagerdal, 2007, Appl Microbiol Biotechnol 74(5), 937-953.
He et al, 2014, Biotechnol Lett 36(3), 523-529.
Sonderegger et al, 2004, Biotechnol Bioengg 87(1), 90-98.
Yang et al, 2008, Biobased Industry Outlook Conf, 1-20.

* cited by examiner

*Primary Examiner* — Tekchand Saidha
(74) *Attorney, Agent, or Firm* — Eric Fechter

(57) ABSTRACT

The present invention relates to processes for producing ethanol from starch-containing material by liquefying the starch-containing material at a temperature above the initial gelatinization temperature using an alpha-amylase; saccharifying using a glucoamylase and fermenting using a *Saccharomyces cerevisiae* yeast strain deposited under Accession No. V14/004037 at National Measurement Institute, Victoria, Australia) or a fermenting organism strain having properties that are about the same as that of the deposited *Saccharomyces cerevisiae* strain or a derivative of *Saccharomyces* strain V14/004037 having the defining characteristics of strain V14/004037. The invention also relates to a *Saccharomyces* yeast strain deposited under the Budapest Treaty and having NMI accession no. V14/004037 or a derivative of strain V14/004037 which exhibits one or more defining characteristics of strain V14/004037. The invention also relates to a process of recovering/extracting oil from an ethanol process of the invention using a *Saccharomyces* strain of the invention and compositions comprising a *Saccharomyces* yeast strain of the invention and naturally occurring and/or non-naturally occurring components.

8 Claims, 5 Drawing Sheets

SEQUENCE LISTING

```
<160> NUMBER OF SEQ ID NOS: 28

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300
```

```
Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
    515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2 atg cgg ctc gtt gct tcc cta acg gcc ttg gtg gcc ttg tcc gta         45
Met Arg Leu Val Ala Ser Leu Thr Ala Leu Val Ala Leu Ser Val
            -175                -170                -165 cct gtc ttt ccc gct gct gtc aac gtg aag cgt gct tcg tcc tac         90
Pro Val Phe Pro Ala Ala Val Asn Val Lys Arg Ala Ser Ser Tyr
        -160                -155                -150 ctg gag atc act ctg agc cag gtc agc aac act ctg atc aag gcc        135
Leu Glu Ile Thr Leu Ser Gln Val Ser Asn Thr Leu Ile Lys Ala
    -145                -140                -135 gtg gtc cag aac act ggt agc gac gag ttg tcc ttc gtt cac ctg        180
Val Val Gln Asn Thr Gly Ser Asp Glu Leu Ser Phe Val His Leu
-130                -125                -120
```

| | | | | | | | | | | | | | | | | |
|---|---|---|---|---|---|---|---|---|---|---|---|---|---|---|---|---|
| aac | ttc | ttc | aag | gac | ccc | gct | cct | gtc | aaa | aag | gta | tcg | gtc | tat | | 225 |
| Asn | Phe | Phe | Lys | Asp | Pro | Ala | Pro | Val | Lys | Lys | Val | Ser | Val | Tyr | | |
| | | | -115 | | | | -110 | | | | -105 | | | | | |

| cgc | gat | ggg | tct | gaa | gtg | cag | ttc | gag | ggc | att | ttg | agc | cgc | tac | aaa | 273 |
|---|---|---|---|---|---|---|---|---|---|---|---|---|---|---|---|---|
| Arg | Asp | Gly | Ser | Glu | Val | Gln | Phe | Glu | Gly | Ile | Leu | Ser | Arg | Tyr | Lys | |
| | | | -100 | | | | -95 | | | | | | -90 | | | |

| tcg | act | ggc | ctc | tct | cgt | gac | gcc | ttt | act | tat | ctg | gct | ccc | gga | gag | 321 |
|---|---|---|---|---|---|---|---|---|---|---|---|---|---|---|---|---|
| Ser | Thr | Gly | Leu | Ser | Arg | Asp | Ala | Phe | Thr | Tyr | Leu | Ala | Pro | Gly | Glu | |
| | | -85 | | | | | -80 | | | | | -75 | | | | |

| tcc | gtc | gag | gac | gtt | ttt | gat | att | gct | tcg | act | tac | gat | ctg | acc | agc | 369 |
|---|---|---|---|---|---|---|---|---|---|---|---|---|---|---|---|---|
| Ser | Val | Glu | Asp | Val | Phe | Asp | Ile | Ala | Ser | Thr | Tyr | Asp | Leu | Thr | Ser | |
| | -70 | | | | | -65 | | | | | -60 | | | | | |

| ggc | ggc | cct | gta | act | atc | cgt | act | gag | gga | gtt | gtt | ccc | tac | gcc | acg | 417 |
|---|---|---|---|---|---|---|---|---|---|---|---|---|---|---|---|---|
| Gly | Gly | Pro | Val | Thr | Ile | Arg | Thr | Glu | Gly | Val | Val | Pro | Tyr | Ala | Thr | |
| -55 | | | | | -50 | | | | | -45 | | | | | -40 | |

| gct | aac | agc | act | gat | att | gcc | ggc | tac | atc | tca | tac | tcg | tct | aat | gtg | 465 |
|---|---|---|---|---|---|---|---|---|---|---|---|---|---|---|---|---|
| Ala | Asn | Ser | Thr | Asp | Ile | Ala | Gly | Tyr | Ile | Ser | Tyr | Ser | Ser | Asn | Val | |
| | | | | -35 | | | | | -30 | | | | | -25 | | |

| ttg | acc | att | gat | gtc | gat | ggc | gcc | gct | gct | gcc | act | gtc | tcc | aag | gca | 513 |
|---|---|---|---|---|---|---|---|---|---|---|---|---|---|---|---|---|
| Leu | Thr | Ile | Asp | Val | Asp | Gly | Ala | Ala | Ala | Ala | Thr | Val | Ser | Lys | Ala | |
| | | | -20 | | | | | -15 | | | | | -10 | | | |

| atc | act | cct | ttg | gac | cgc | cgc | act | agg | atc | agt | tcc | tgc | tcc | ggc | agc | 561 |
|---|---|---|---|---|---|---|---|---|---|---|---|---|---|---|---|---|
| Ile | Thr | Pro | Leu | Asp | Arg | Arg | Thr | Arg | Ile | Ser | Ser | Cys | Ser | Gly | Ser | |
| -5 | | | | | | -1 | 1 | | | | 5 | | | | | |

| aga | cag | agc | gct | ctt | act | acg | gct | ctc | aga | aac | gct | gct | tct | ctt | gcc | 609 |
|---|---|---|---|---|---|---|---|---|---|---|---|---|---|---|---|---|
| Arg | Gln | Ser | Ala | Leu | Thr | Thr | Ala | Leu | Arg | Asn | Ala | Ala | Ser | Leu | Ala | |
| 10 | | | | | 15 | | | | | 20 | | | | | 25 | |

| aac | gca | gct | gcc | gac | gcg | gct | cag | tct | gga | tca | gct | tca | aag | ttc | agc | 657 |
|---|---|---|---|---|---|---|---|---|---|---|---|---|---|---|---|---|
| Asn | Ala | Ala | Ala | Asp | Ala | Ala | Gln | Ser | Gly | Ser | Ala | Ser | Lys | Phe | Ser | |
| | | | 30 | | | | | 35 | | | | | 40 | | | |

| gag | tac | ttc | aag | act | act | tct | agc | tct | acc | cgc | cag | acc | gtg | gct | gcg | 705 |
|---|---|---|---|---|---|---|---|---|---|---|---|---|---|---|---|---|
| Glu | Tyr | Phe | Lys | Thr | Thr | Ser | Ser | Ser | Thr | Arg | Gln | Thr | Val | Ala | Ala | |
| | | | 45 | | | | | 50 | | | | | 55 | | | |

| cgt | ctt | cgg | gct | gtt | gcg | cgg | gag | gca | tct | tcg | tct | tct | tcg | gga | gcc | 753 |
|---|---|---|---|---|---|---|---|---|---|---|---|---|---|---|---|---|
| Arg | Leu | Arg | Ala | Val | Ala | Arg | Glu | Ala | Ser | Ser | Ser | Ser | Ser | Gly | Ala | |
| | | 60 | | | | | 65 | | | | | 70 | | | | |

| acc | acg | tac | tac | tgc | gac | gat | ccc | tac | ggc | tac | tgt | tcc | tcc | aac | gtc | 801 |
|---|---|---|---|---|---|---|---|---|---|---|---|---|---|---|---|---|
| Thr | Thr | Tyr | Tyr | Cys | Asp | Asp | Pro | Tyr | Gly | Tyr | Cys | Ser | Ser | Asn | Val | |
| 75 | | | | | 80 | | | | | 85 | | | | | | |

| ctg | gct | tac | acc | ctg | cct | tca | tac | aac | ata | atc | gcc | aac | tgt | gac | att | 849 |
|---|---|---|---|---|---|---|---|---|---|---|---|---|---|---|---|---|
| Leu | Ala | Tyr | Thr | Leu | Pro | Ser | Tyr | Asn | Ile | Ile | Ala | Asn | Cys | Asp | Ile | |
| 90 | | | | | 95 | | | | | 100 | | | | | 105 | |

| ttc | tat | act | tac | ctg | ccg | gct | ctg | acc | agt | acc | tgt | cac | gct | cag | gat | 897 |
|---|---|---|---|---|---|---|---|---|---|---|---|---|---|---|---|---|
| Phe | Tyr | Thr | Tyr | Leu | Pro | Ala | Leu | Thr | Ser | Thr | Cys | His | Ala | Gln | Asp | |
| | | | | 110 | | | | | 115 | | | | | 120 | | |

| caa | gcg | acc | act | gcc | ctt | cac | gag | ttc | acc | cat | gcg | cct | ggc | gtc | tac | 945 |
|---|---|---|---|---|---|---|---|---|---|---|---|---|---|---|---|---|
| Gln | Ala | Thr | Thr | Ala | Leu | His | Glu | Phe | Thr | His | Ala | Pro | Gly | Val | Tyr | |
| | | | 125 | | | | | 130 | | | | | 135 | | | |

| agc | cct | ggc | acg | gac | gac | ctg | gcg | tat | ggc | tac | cag | gct | gcg | atg | ggt | 993 |
|---|---|---|---|---|---|---|---|---|---|---|---|---|---|---|---|---|
| Ser | Pro | Gly | Thr | Asp | Asp | Leu | Ala | Tyr | Gly | Tyr | Gln | Ala | Ala | Met | Gly | |
| | | 140 | | | | | 145 | | | | | 150 | | | | |

| ctc | agc | agc | agc | cag | gct | gtc | atg | aac | gct | gac | acc | tac | gct | ctc | tat | 1041 |
|---|---|---|---|---|---|---|---|---|---|---|---|---|---|---|---|---|
| Leu | Ser | Ser | Ser | Gln | Ala | Val | Met | Asn | Ala | Asp | Thr | Tyr | Ala | Leu | Tyr | |
| 155 | | | | | 160 | | | | | 165 | | | | | | |

| gcg | aat | gcc | ata | tac | ctt | ggt | tgc | taa | | | | | | | | 1068 |
|---|---|---|---|---|---|---|---|---|---|---|---|---|---|---|---|---|
| Ala | Asn | Ala | Ile | Tyr | Leu | Gly | Cys | | | | | | | | | |
| 170 | | | | 175 | | | | | | | | | | | | |

<210> SEQ ID NO 3
<211> LENGTH: 355

<212> TYPE: PRT
<213> ORGANISM: Thermoascus aurantiacus

<400> SEQUENCE: 3

```
Met Arg Leu Val Ala Ser Leu Thr Ala Leu Val Ala Leu Ser Val
    -175             -170             -165
Pro Val Phe Pro Ala Ala Val Asn Val Lys Arg Ala Ser Ser Tyr
    -160             -155             -150
Leu Glu Ile Thr Leu Ser Gln Val Ser Asn Thr Leu Ile Lys Ala
    -145             -140             -135
Val Val Gln Asn Thr Gly Ser Asp Glu Leu Ser Phe Val His Leu
    -130             -125             -120
Asn Phe Phe Lys Asp Pro Ala Pro Val Lys Lys Val Ser Val Tyr
    -115             -110             -105
Arg Asp Gly Ser Glu Val Gln Phe Glu Gly Ile Leu Ser Arg Tyr Lys
    -100              -95              -90
Ser Thr Gly Leu Ser Arg Asp Ala Phe Thr Tyr Leu Ala Pro Gly Glu
     -85              -80              -75
Ser Val Glu Asp Val Phe Asp Ile Ala Ser Tyr Asp Leu Thr Ser
     -70              -65              -60
Gly Gly Pro Val Thr Ile Arg Thr Glu Gly Val Val Pro Tyr Ala Thr
-55              -50              -45              -40
Ala Asn Ser Thr Asp Ile Ala Gly Tyr Ile Ser Tyr Ser Asn Val
                 -35              -30              -25
Leu Thr Ile Asp Val Asp Gly Ala Ala Ala Thr Val Ser Lys Ala
                 -20              -15              -10
Ile Thr Pro Leu Asp Arg Arg Thr Arg Ile Ser Ser Cys Ser Gly Ser
                  -5              -1   1               5
Arg Gln Ser Ala Leu Thr Thr Ala Leu Arg Asn Ala Ala Ser Leu Ala
 10                  15                  20                  25
Asn Ala Ala Ala Asp Ala Ala Gln Ser Gly Ser Ala Ser Lys Phe Ser
                  30                  35                  40
Glu Tyr Phe Lys Thr Thr Ser Ser Thr Arg Gln Thr Val Ala Ala
                  45                  50                  55
Arg Leu Arg Ala Val Ala Arg Glu Ala Ser Ser Ser Ser Gly Ala
                  60                  65                  70
Thr Thr Tyr Tyr Cys Asp Asp Pro Tyr Gly Tyr Cys Ser Ser Asn Val
 75                  80                  85
Leu Ala Tyr Thr Leu Pro Ser Tyr Asn Ile Ile Ala Asn Cys Asp Ile
 90                  95                 100                 105
Phe Tyr Thr Tyr Leu Pro Ala Leu Thr Ser Thr Cys His Ala Gln Asp
                 110                 115                 120
Gln Ala Thr Thr Ala Leu His Glu Phe Thr His Ala Pro Gly Val Tyr
                 125                 130                 135
Ser Pro Gly Thr Asp Asp Leu Ala Tyr Gly Tyr Gln Ala Ala Met Gly
                 140                 145                 150
Leu Ser Ser Ser Gln Ala Val Met Asn Ala Asp Thr Tyr Ala Leu Tyr
                 155                 160                 165
Ala Asn Ala Ile Tyr Leu Gly Cys
170                 175
```

<210> SEQ ID NO 4
<211> LENGTH: 49
<212> TYPE: DNA
<213> ORGANISM: Artificial Sequence -continued

```
<220> FEATURE:
<223> OTHER INFORMATION: Synthetic Construct

<400> SEQUENCE: 4
aacgacggta cccggggatc ggatccatgc ggctcgttgc ttccctaac           49

<210> SEQ ID NO 5
<211> LENGTH: 48
<212> TYPE: DNA
<213> ORGANISM: Artificial Sequence
<220> FEATURE:
<223> OTHER INFORMATION: Artificial Construct

<400> SEQUENCE: 5
ctaattacat gatgcggccc ttaattaatt agcaaccaag gtatatgg            48

<210> SEQ ID NO 6
<211> LENGTH: 20
<212> TYPE: DNA
<213> ORGANISM: Artificial Sequence
<220> FEATURE:
<223> OTHER INFORMATION: Artificial Construct

<400> SEQUENCE: 6
taggagttta gtgaacttgc                                           20

<210> SEQ ID NO 7
<211> LENGTH: 18
<212> TYPE: DNA
<213> ORGANISM: Artificial Sequence
<220> FEATURE:
<223> OTHER INFORMATION: Artificial Construct

<400> SEQUENCE: 7
ttcgagcgtc ccaaaacc                                             18

<210> SEQ ID NO 8
<211> LENGTH: 1851
<212> TYPE: DNA
<213> ORGANISM: Penicillium oxalicum
<220> FEATURE:
<221> NAME/KEY: CDS
<222> LOCATION: (1)..(1851)
<220> FEATURE:
<221> NAME/KEY: misc_signal
<222> LOCATION: (1)..(63)

<400> SEQUENCE: 8 atg cgt ctc act cta tta tca ggt gta gcc ggc gtt ctc tgc gca gga    48
Met Arg Leu Thr Leu Leu Ser Gly Val Ala Gly Val Leu Cys Ala Gly
1               5                   10                  15 cag ctg acg gcg gcg cgt cct gat ccc aag ggt ggg aat ctg acg ccg    96
Gln Leu Thr Ala Ala Arg Pro Asp Pro Lys Gly Gly Asn Leu Thr Pro
            20                  25                  30 ttc atc cac aaa gag ggc gag cgg tcg ctc caa ggc atc ttg gac aat   144
Phe Ile His Lys Glu Gly Glu Arg Ser Leu Gln Gly Ile Leu Asp Asn
        35                  40                  45 ctc ggt ggg cga ggt aag aaa aca ccc ggc act gcc gca ggg ttg ttt   192
Leu Gly Gly Arg Gly Lys Lys Thr Pro Gly Thr Ala Ala Gly Leu Phe
    50                  55                  60 att gcc agt cca aac aca gag aat cca aac tat tat tat aca tgg act   240
Ile Ala Ser Pro Asn Thr Glu Asn Pro Asn Tyr Tyr Tyr Thr Trp Thr
65                  70                  75                  80 cgt gac tca gct ttg act gcc aag tgc ttg atc gac ctg ttc gaa gac   288
Arg Asp Ser Ala Leu Thr Ala Lys Cys Leu Ile Asp Leu Phe Glu Asp
```

-continued

```
                  85                      90                      95
tct cgg gca aag ttt cca att gac cgc aaa tac ttg gaa aca gga att     336
Ser Arg Ala Lys Phe Pro Ile Asp Arg Lys Tyr Leu Glu Thr Gly Ile
        100                     105                     110 cgg gac tac gtg tcg tcc caa gca atc ctc cag agt gtg tct aat cct     384
Arg Asp Tyr Val Ser Ser Gln Ala Ile Leu Gln Ser Val Ser Asn Pro
            115                     120                     125 tct gga acc ctg aag gat ggc tct ggt ctg ggt gaa ccc aag ttt gag     432
Ser Gly Thr Leu Lys Asp Gly Ser Gly Leu Gly Glu Pro Lys Phe Glu
    130                     135                     140 att gac ctg aat ccc ttt tcg ggt gcc tgg ggt cgg cct cag cgg gat     480
Ile Asp Leu Asn Pro Phe Ser Gly Ala Trp Gly Arg Pro Gln Arg Asp
145                     150                     155                 160 ggc cca gcg ctg cga gcg acc gct atg atc acc tac gcc aac tac ctg     528
Gly Pro Ala Leu Arg Ala Thr Ala Met Ile Thr Tyr Ala Asn Tyr Leu
                    165                     170                     175 ata tcc cat ggt cag aaa tcg gat gtg tca cag gtc atg tgg ccg att     576
Ile Ser His Gly Gln Lys Ser Asp Val Ser Gln Val Met Trp Pro Ile
                180                     185                     190 att gcc aat gat cta gca tat gtt ggt caa tac tgg aat aat acc gga     624
Ile Ala Asn Asp Leu Ala Tyr Val Gly Gln Tyr Trp Asn Asn Thr Gly
            195                     200                     205 ttt gac ctg tgg gaa gag gtg gat ggg tca agc ttt ttc acg att gcg     672
Phe Asp Leu Trp Glu Glu Val Asp Gly Ser Ser Phe Phe Thr Ile Ala
        210                     215                     220 gtc cag cac cga gcc ctt gtt gaa ggc tcg caa ctg gcg aaa aag ctc     720
Val Gln His Arg Ala Leu Val Glu Gly Ser Gln Leu Ala Lys Lys Leu
225                     230                     235                 240 ggc aag tcc tgc gat gcc tgt gat tct cag cct ccc cag ata ttg tgt     768
Gly Lys Ser Cys Asp Ala Cys Asp Ser Gln Pro Pro Gln Ile Leu Cys
                    245                     250                     255 ttc ctg cag agt ttc tgg aac gga aag tac atc acc tcc aac atc aac     816
Phe Leu Gln Ser Phe Trp Asn Gly Lys Tyr Ile Thr Ser Asn Ile Asn
                260                     265                     270 acg caa gca agc cgc tct ggt atc gac ctg gac tct gtc ctg gga agc     864
Thr Gln Ala Ser Arg Ser Gly Ile Asp Leu Asp Ser Val Leu Gly Ser
            275                     280                     285 att cat acc ttt gat ccc gaa gca gcc tgt gac gat gca act ttc cag     912
Ile His Thr Phe Asp Pro Glu Ala Ala Cys Asp Asp Ala Thr Phe Gln
        290                     295                     300 cct tgt tct gcc cgc gct ctg gcg aac cac aag gtc tat gtg gat tcc     960
Pro Cys Ser Ala Arg Ala Leu Ala Asn His Lys Val Tyr Val Asp Ser
305                     310                     315                 320 ttc cgc tct atc tac aag att aat gcg ggt ctt gca gag gga tcg gct    1008
Phe Arg Ser Ile Tyr Lys Ile Asn Ala Gly Leu Ala Glu Gly Ser Ala
                    325                     330                     335 gcc aac gtt ggc cgc tac ccc gag gat gtt tac caa gga ggc aat cca    1056
Ala Asn Val Gly Arg Tyr Pro Glu Asp Val Tyr Gln Gly Gly Asn Pro
                340                     345                     350 tgg tat ctc gcc acc cta ggc gca tct gaa ttg ctt tac gac gcc ttg    1104
Trp Tyr Leu Ala Thr Leu Gly Ala Ser Glu Leu Leu Tyr Asp Ala Leu
            355                     360                     365 tac cag tgg gac aga ctt ggc aaa ctt gaa gtc tcg gag acc tcg ttg    1152
Tyr Gln Trp Asp Arg Leu Gly Lys Leu Glu Val Ser Glu Thr Ser Leu
        370                     375                     380 tca ttc ttc aaa gac ttt gac gcg acc gtg aaa att ggc tcg tac tcg    1200
Ser Phe Phe Lys Asp Phe Asp Ala Thr Val Lys Ile Gly Ser Tyr Ser
385                     390                     395                 400 agg aac agc aag acc tac aag aaa ttg acc cag tcc atc aag tcg tac    1248
```

```
Arg Asn Ser Lys Thr Tyr Lys Lys Leu Thr Gln Ser Ile Lys Ser Tyr
            405                 410                 415 gcg gac ggg ttc atc cag tta gtg cag cag tac act cct tct aat gga        1296
Ala Asp Gly Phe Ile Gln Leu Val Gln Gln Tyr Thr Pro Ser Asn Gly
            420                 425                 430 tct ctg gcc gag caa tac gat cgc aat acg gct gct cct ctc tct gca        1344
Ser Leu Ala Glu Gln Tyr Asp Arg Asn Thr Ala Ala Pro Leu Ser Ala
            435                 440                 445 aac gat ctg act tgg tca ttt gcc tct ttc ttg acg gct acg caa cgc        1392
Asn Asp Leu Thr Trp Ser Phe Ala Ser Phe Leu Thr Ala Thr Gln Arg
            450                 455                 460 cgc gat gcc gtg gtt cct ccc tcc tgg ggc gca aag tcg gca aac aaa        1440
Arg Asp Ala Val Val Pro Pro Ser Trp Gly Ala Lys Ser Ala Asn Lys
465                 470                 475                 480 gtc cca acc act tgt tca gcc tcc cct gtt gtg ggt act tat aag gcg        1488
Val Pro Thr Thr Cys Ser Ala Ser Pro Val Val Gly Thr Tyr Lys Ala
            485                 490                 495 ccc acg gca act ttc tca tcc aag act aag tgc gtc ccc gct aaa gat        1536
Pro Thr Ala Thr Phe Ser Ser Lys Thr Lys Cys Val Pro Ala Lys Asp
            500                 505                 510 att gtg cct atc acg ttc tac ctg att gag aac act tac tat gga gag        1584
Ile Val Pro Ile Thr Phe Tyr Leu Ile Glu Asn Thr Tyr Tyr Gly Glu
            515                 520                 525 aac gtc ttc atg agt ggc aac att act gcg ctg ggt aac tgg gac gcc        1632
Asn Val Phe Met Ser Gly Asn Ile Thr Ala Leu Gly Asn Trp Asp Ala
530                 535                 540 aag aaa ggc ttc cca ctc acc gca aac ctc tac acg caa gat caa aac        1680
Lys Lys Gly Phe Pro Leu Thr Ala Asn Leu Tyr Thr Gln Asp Gln Asn
545                 550                 555                 560 ttg tgg ttc gcc agt gtc gag ttc atc cca gca ggc aca ccc ttt gag        1728
Leu Trp Phe Ala Ser Val Glu Phe Ile Pro Ala Gly Thr Pro Phe Glu
            565                 570                 575 tac aag tac tac aag gtc gag ccc aat ggc gat att act tgg gag aag        1776
Tyr Lys Tyr Tyr Lys Val Glu Pro Asn Gly Asp Ile Thr Trp Glu Lys
            580                 585                 590 ggt ccc aac cgg gtg ttc gtc gct ccc acg gga tgc cca gtt cag cct        1824
Gly Pro Asn Arg Val Phe Val Ala Pro Thr Gly Cys Pro Val Gln Pro
            595                 600                 605 cac tcc aac gac gtg tgg cag ttt tga                                    1851
His Ser Asn Asp Val Trp Gln Phe
            610                 615

<210> SEQ ID NO 9
<211> LENGTH: 616
<212> TYPE: PRT
<213> ORGANISM: Penicillium oxalicum

<400> SEQUENCE: 9

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Asn Leu Thr Pro
            20                  25                  30

Phe Ile His Lys Glu Gly Glu Arg Ser Leu Gln Gly Ile Leu Asp Asn
            35                  40                  45

Leu Gly Gly Arg Gly Lys Lys Thr Pro Gly Thr Ala Ala Gly Leu Phe
        50                  55                  60

Ile Ala Ser Pro Asn Thr Glu Asn Pro Asn Tyr Tyr Tyr Thr Trp Thr
65              70                  75                  80

Arg Asp Ser Ala Leu Thr Ala Lys Cys Leu Ile Asp Leu Phe Glu Asp
```

```
            85                  90                  95
Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
            115                 120                 125

Ser Gly Thr Leu Lys Asp Gly Ser Gly Leu Gly Glu Pro Lys Phe Glu
            130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
                180                 185                 190

Ile Ala Asn Asp Leu Ala Tyr Val Gly Gln Tyr Trp Asn Asn Thr Gly
                195                 200                 205

Phe Asp Leu Trp Glu Glu Val Asp Gly Ser Ser Phe Phe Thr Ile Ala
                210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
                245                 250                 255

Phe Leu Gln Ser Phe Trp Asn Gly Lys Tyr Ile Thr Ser Asn Ile Asn
                260                 265                 270

Thr Gln Ala Ser Arg Ser Gly Ile Asp Leu Asp Ser Val Leu Gly Ser
                275                 280                 285

Ile His Thr Phe Asp Pro Glu Ala Ala Cys Asp Ala Thr Phe Gln
                290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
                340                 345                 350

Trp Tyr Leu Ala Thr Leu Gly Ala Ser Glu Leu Leu Tyr Asp Ala Leu
                355                 360                 365

Tyr Gln Trp Asp Arg Leu Gly Lys Leu Glu Val Ser Glu Thr Ser Leu
                370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
                420                 425                 430

Ser Leu Ala Glu Gln Tyr Asp Arg Asn Thr Ala Ala Pro Leu Ser Ala
                435                 440                 445

Asn Asp Leu Thr Trp Ser Phe Ala Ser Phe Leu Thr Ala Thr Gln Arg
                450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
                500                 505                 510
```

```
Ile Val Pro Ile Thr Phe Tyr Leu Ile Glu Asn Thr Tyr Tyr Gly Glu
        515                 520                 525

Asn Val Phe Met Ser Gly Asn Ile Thr Ala Leu Gly Asn Trp Asp Ala
        530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
        595                 600                 605

His Ser Asn Asp Val Trp Gln Phe
    610                 615

<210> SEQ ID NO 10
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10 atg agg cgg gtg gtt gcc ctc ttc att gca att ttg atg ctt gga agc     48
Met Arg Arg Val Val Ala Leu Phe Ile Ala Ile Leu Met Leu Gly Ser
        -25                 -20                 -15 atc gtt gga gcg aac gtt aag agc gtt ggc gcg gcg gag ccg aag ccg     96
Ile Val Gly Ala Asn Val Lys Ser Val Gly Ala Ala Glu Pro Lys Pro
    -10                 -5              -1  1               5 ctc aac gtc ata ata gtc tgg cac cag cac cag ccc tac tac tac gac    144
Leu Asn Val Ile Ile Val Trp His Gln His Gln Pro Tyr Tyr Tyr Asp
                10                  15                  20 cct gtc cag gac gtc tac acc agg ccc tgg gtc agg ctc cac gcg gcg    192
Pro Val Gln Asp Val Tyr Thr Arg Pro Trp Val Arg Leu His Ala Ala
            25                  30                  35 aac aac tac tgg aag atg gcc cac tac ctg agc cag tac ccg gag gtt    240
Asn Asn Tyr Trp Lys Met Ala His Tyr Leu Ser Gln Tyr Pro Glu Val
        40                  45                  50 cac gcc acc att gac ctc tcg ggt tcg ctg ata gcc cag ctt gcc gac    288
His Ala Thr Ile Asp Leu Ser Gly Ser Leu Ile Ala Gln Leu Ala Asp
    55                  60                  65 tac atg aac ggc aag aag gac acc tac cag ata atc acc gag aag ata    336
Tyr Met Asn Gly Lys Lys Asp Thr Tyr Gln Ile Ile Thr Glu Lys Ile
70                  75                  80                  85 gcc aac ggg gaa ccc ctc acc gtc gac gag aag tgg ttc atg ctc cag    384
Ala Asn Gly Glu Pro Leu Thr Val Asp Glu Lys Trp Phe Met Leu Gln
                90                  95                  100 gca ccg gga ggg ttc ttc gac aac acc atc ccc tgg aac ggt gaa ccg    432
Ala Pro Gly Gly Phe Phe Asp Asn Thr Ile Pro Trp Asn Gly Glu Pro
            105                 110                 115 ata acc gac ccc aac ggc aac ccg ata agg gac ttc tgg gac cgc tac    480
Ile Thr Asp Pro Asn Gly Asn Pro Ile Arg Asp Phe Trp Asp Arg Tyr
        120                 125                 130
```

| | | |
|---|---|---|
| acg gag ctg aag aac aag atg ctc agc gca aag gcc aag tac gca aac<br>Thr Glu Leu Lys Asn Lys Met Leu Ser Ala Lys Ala Lys Tyr Ala Asn<br>135                    140                    145 | | 528 |
| ttc gtg act gag agc cag aag gtc gct gtg acg aac gag ttc aca gag<br>Phe Val Thr Glu Ser Gln Lys Val Ala Val Thr Asn Glu Phe Thr Glu<br>150                    155                    160                    165 | | 576 |
| cag gac tac ata gac cta gcg gtt ctc ttc aat ctc gct tgg att gac<br>Gln Asp Tyr Ile Asp Leu Ala Val Leu Phe Asn Leu Ala Trp Ile Asp<br>                  170                    175                    180 | | 624 |
| tac aat tac atc acg agc acg ccg gag ttc aag gcc ctc tac gac aag<br>Tyr Asn Tyr Ile Thr Ser Thr Pro Glu Phe Lys Ala Leu Tyr Asp Lys<br>                  185                    190                    195 | | 672 |
| gtt gac gag ggc ggc tat aca agg gcg gac gtc aaa acc gtt ctc gac<br>Val Asp Glu Gly Gly Tyr Thr Arg Ala Asp Val Lys Thr Val Leu Asp<br>200                    205                    210 | | 720 |
| gcc cag atc tgg ctt ctc aac cac acc ttc gag gag cac gag aag ata<br>Ala Gln Ile Trp Leu Leu Asn His Thr Phe Glu Glu His Glu Lys Ile<br>215                    220                    225 | | 768 |
| aac ctc ctc ctc gga aac ggc aac gtc gag gtc acg gtc gtt ccc tac<br>Asn Leu Leu Leu Gly Asn Gly Asn Val Glu Val Thr Val Val Pro Tyr<br>230                    235                    240                    245 | | 816 |
| gcc cac ccg ata ggc ccg ata ctc aac gac ttc ggc tgg gac agc gac<br>Ala His Pro Ile Gly Pro Ile Leu Asn Asp Phe Gly Trp Asp Ser Asp<br>                  250                    255                    260 | | 864 |
| ttc aac gac cag gtc aag aag gcc gac gaa ctg tac aag ccg tac ctc<br>Phe Asn Asp Gln Val Lys Lys Ala Asp Glu Leu Tyr Lys Pro Tyr Leu<br>                  265                    270                    275 | | 912 |
| ggc ggc ggc acc gcg gtt cca aaa ggc gga tgg gcg gct gag agc gcc<br>Gly Gly Gly Thr Ala Val Pro Lys Gly Gly Trp Ala Ala Glu Ser Ala<br>280                    285                    290 | | 960 |
| ctc aac gac aaa act ctg gag atc ctc gcc gag aac ggc tgg gag tgg<br>Leu Asn Asp Lys Thr Leu Glu Ile Leu Ala Glu Asn Gly Trp Glu Trp<br>295                    300                    305 | | 1008 |
| gtc atg acc gac cag atg gtt ctc gga aag ctc ggc att gag gga acc<br>Val Met Thr Asp Gln Met Val Leu Gly Lys Leu Gly Ile Glu Gly Thr<br>310                    315                    320                    325 | | 1056 |
| gtc gag aac tac cac aag ccc tgg gtg gcc gag ttc aac gga aag aag<br>Val Glu Asn Tyr His Lys Pro Trp Val Ala Glu Phe Asn Gly Lys Lys<br>                  330                    335                    340 | | 1104 |
| ata tac ctc ttc cca aga aat cac gat cta agt gac aga gtt ggc ttt<br>Ile Tyr Leu Phe Pro Arg Asn His Asp Leu Ser Asp Arg Val Gly Phe<br>                  345                    350                    355 | | 1152 |
| acc tac agc gga atg aac cag cag cag gcc gtt gag gac ttc gtc aac<br>Thr Tyr Ser Gly Met Asn Gln Gln Gln Ala Val Glu Asp Phe Val Asn<br>360                    365                    370 | | 1200 |
| gag ctc ctc aag ctc cag aag cag aac tac gat ggc tcg ctg gtt tac<br>Glu Leu Leu Lys Leu Gln Lys Gln Asn Tyr Asp Gly Ser Leu Val Tyr<br>375                    380                    385 | | 1248 |
| gtg gtc acg ctc gac ggc gag aac ccc gtg gag aac tac ccc tac gac<br>Val Val Thr Leu Asp Gly Glu Asn Pro Val Glu Asn Tyr Pro Tyr Asp<br>390                    395                    400                    405 | | 1296 |
| ggg gag ctc ttc ctc acc gaa ctc tac aag aag ctg acc gaa ctc cag<br>Gly Glu Leu Phe Leu Thr Glu Leu Tyr Lys Lys Leu Thr Glu Leu Gln<br>                  410                    415                    420 | | 1344 |
| gag cag ggt ctc ata aga acc ctc acc ccg agc gag tac atc cag ctc<br>Glu Gln Gly Leu Ile Arg Thr Leu Thr Pro Ser Glu Tyr Ile Gln Leu<br>                  425                    430                    435 | | 1392 |
| tac ggc gac aag gcc aac aag ctc aca cct cgg atg atg gag cgc ctt<br>Tyr Gly Asp Lys Ala Asn Lys Leu Thr Pro Arg Met Met Glu Arg Leu<br>440                    445                    450 | | 1440 |

```
gac ctc acc gga gac aac gtt aac gcc ctc ctc aag gcc cag agc ctc      1488
Asp Leu Thr Gly Asp Asn Val Asn Ala Leu Leu Lys Ala Gln Ser Leu
            455                 460                 465 ggc gaa ctc tac gac atg acc ggc gtt aag gag gag atg cag tgg ccc      1536
Gly Glu Leu Tyr Asp Met Thr Gly Val Lys Glu Glu Met Gln Trp Pro
470                 475                 480                 485 gag agc agc tgg ata gac gga acc ctc tcc acg tgg ata ggc gag ccc      1584
Glu Ser Ser Trp Ile Asp Gly Thr Leu Ser Thr Trp Ile Gly Glu Pro
                        490                 495                 500 cag gag aac tac ggc tgg tac tgg ctc tac atg gcc agg aag gcc ctt      1632
Gln Glu Asn Tyr Gly Trp Tyr Trp Leu Tyr Met Ala Arg Lys Ala Leu
            505                 510                 515 atg gag aac aag gat aaa atg agc cag gcg gac tgg gag aag gcc tac      1680
Met Glu Asn Lys Asp Lys Met Ser Gln Ala Asp Trp Glu Lys Ala Tyr
520                 525                 530 gag tac ctg ctc cgc gcc gag gca agc gac tgg ttc tgg tgg tac gga      1728
Glu Tyr Leu Leu Arg Ala Glu Ala Ser Asp Trp Phe Trp Trp Tyr Gly
                535                 540                 545 agc gac cag gac agc ggc cag gac tac acc ttc gac cgc tac ctg aag      1776
Ser Asp Gln Asp Ser Gly Gln Asp Tyr Thr Phe Asp Arg Tyr Leu Lys
550                 555                 560                 565 acc tac ctc tac gag atg tac aag ctg gca gga gtc gag ccg ccg agc      1824
Thr Tyr Leu Tyr Glu Met Tyr Lys Leu Ala Gly Val Glu Pro Pro Ser
                    570                 575                 580 tac ctc ttc ggc aac tac ttc ccg gac gga gag ccc tac acc acg agg      1872
Tyr Leu Phe Gly Asn Tyr Phe Pro Asp Gly Glu Pro Tyr Thr Thr Arg
                585                 590                 595 ggc ctg gtc gga ctc aag gac ggc gag atg aag aac ttc tcc agc atg      1920
Gly Leu Val Gly Leu Lys Asp Gly Glu Met Lys Asn Phe Ser Ser Met
            600                 605                 610 tcc ccg ctg gca aag ggc gtg agc gtc tat ttc gac ggc gag ggg ata      1968
Ser Pro Leu Ala Lys Gly Val Ser Val Tyr Phe Asp Gly Glu Gly Ile
            615                 620                 625 cac ttc ata gtg aaa ggg aac ctg gac agg ttc gag gtg agc atc tgg      2016
His Phe Ile Val Lys Gly Asn Leu Asp Arg Phe Glu Val Ser Ile Trp
630                 635                 640                 645 gag aag gat gag cgc gtt ggc aac acg ttc acc cgc ctc caa gag aag      2064
Glu Lys Asp Glu Arg Val Gly Asn Thr Phe Thr Arg Leu Gln Glu Lys
                    650                 655                 660 ccg gac gag ttg agc tat ttc atg ttc cca ttc tca agg gac agc gtt      2112
Pro Asp Glu Leu Ser Tyr Phe Met Phe Pro Phe Ser Arg Asp Ser Val
                665                 670                 675 ggt ctc ctc ata acc aag cac gtc gtg tac gag aac gga aag gcc gag      2160
Gly Leu Leu Ile Thr Lys His Val Val Tyr Glu Asn Gly Lys Ala Glu
            680                 685                 690 ata tac ggc gcc acc gac tac gag aag agc gag aag ctt ggg gaa gcc      2208
Ile Tyr Gly Ala Thr Asp Tyr Glu Lys Ser Glu Lys Leu Gly Glu Ala
            695                 700                 705 acc gtc aag aac acg agc gaa gga atc gaa gtc gtc ctt ccc ttt gac      2256
Thr Val Lys Asn Thr Ser Glu Gly Ile Glu Val Val Leu Pro Phe Asp
710                 715                 720                 725 tac ata gaa aac ccc tcc gac ttc tac ttc gct gtc tcg acg gtc aaa      2304
Tyr Ile Glu Asn Pro Ser Asp Phe Tyr Phe Ala Val Ser Thr Val Lys
                    730                 735                 740 gat gga gac ctt gag gtg ata agc act cct gtg gag ctc aag ctc ccg      2352
Asp Gly Asp Leu Glu Val Ile Ser Thr Pro Val Glu Leu Lys Leu Pro
                745                 750                 755 acc gag gtc aag gga gtc gtc ata gcc gat ata acc gac cca gaa ggc      2400
Thr Glu Val Lys Gly Val Val Ile Ala Asp Ile Thr Asp Pro Glu Gly
```

-continued

```
       760                 765                 770
gac gac cat ggg ccc gga aac tac act tat ccc acg gac aag gtc ttc      2448
Asp Asp His Gly Pro Gly Asn Tyr Thr Tyr Pro Thr Asp Lys Val Phe
        775                 780                 785 aag cca ggt gtt ttc gac ctc ctc cgc ttc agg atg ctc gaa cag acg      2496
Lys Pro Gly Val Phe Asp Leu Leu Arg Phe Arg Met Leu Glu Gln Thr
790                 795                 800                 805 gag agc tac gtc atg gag ttc tac ttc aag gac cta ggt ggt aac ccg      2544
Glu Ser Tyr Val Met Glu Phe Tyr Phe Lys Asp Leu Gly Gly Asn Pro
                810                 815                 820 tgg aac gga ccc aac ggc ttc agc ctc cag ata atc gag gtc tac ctc      2592
Trp Asn Gly Pro Asn Gly Phe Ser Leu Gln Ile Ile Glu Val Tyr Leu
            825                 830                 835 gac ttc aag gac ggt gga aac agt tcg gcc att aag atg ttc ccc gac      2640
Asp Phe Lys Asp Gly Gly Asn Ser Ser Ala Ile Lys Met Phe Pro Asp
        840                 845                 850 gga ccg gga gcc aac gtc aac ctc gac ccc gag cat cca tgg gac gtt      2688
Gly Pro Gly Ala Asn Val Asn Leu Asp Pro Glu His Pro Trp Asp Val
855                 860                 865 gcc ttc agg ata gcg ggc tgg gac tac gga aac ctc atc atc ctg ccg      2736
Ala Phe Arg Ile Ala Gly Trp Asp Tyr Gly Asn Leu Ile Ile Leu Pro
870                 875                 880                 885 aac gga acg gcc atc cag ggc gag atg cag att tcc gca gat ccg gtt      2784
Asn Gly Thr Ala Ile Gln Gly Glu Met Gln Ile Ser Ala Asp Pro Val
                890                 895                 900 aag aac gcc ata ata gtc aag gtt cca aag aag tac atc gcc ata aac      2832
Lys Asn Ala Ile Ile Val Lys Val Pro Lys Lys Tyr Ile Ala Ile Asn
            905                 910                 915 gag gac tac ggc ctc tgg gga gac gtc ctc gtc ggc tcg cag gac ggc      2880
Glu Asp Tyr Gly Leu Trp Gly Asp Val Leu Val Gly Ser Gln Asp Gly
        920                 925                 930 tac ggc ccg gac aag tgg aga acg gcg gca gtg gat gcg gag cag tgg      2928
Tyr Gly Pro Asp Lys Trp Arg Thr Ala Ala Val Asp Ala Glu Gln Trp
935                 940                 945 aag ctt gga ggt gcg gac ccg cag gca gtc ata aac ggc gtg gcc ccg      2976
Lys Leu Gly Gly Ala Asp Pro Gln Ala Val Ile Asn Gly Val Ala Pro
950                 955                 960                 965 cgc gtc att gat gag ctg gtt ccg cag ggc ttt gaa ccg acc cag gag      3024
Arg Val Ile Asp Glu Leu Val Pro Gln Gly Phe Glu Pro Thr Gln Glu
                970                 975                 980 gag cag ctg agc agc tac gat gca aac gac atg aag ctc gcc act gtc      3072
Glu Gln Leu Ser Ser Tyr Asp Ala Asn Asp Met Lys Leu Ala Thr Val
            985                 990                 995 aag gcg ctg cta ctc ctc aag cag ggc atc gtt gtg acc gac ccg          3117
Lys Ala Leu Leu Leu Leu Lys Gln Gly Ile Val Val Thr Asp Pro
        1000                1005                1010 gag gga gac gac cac ggg ccg gga acg tac acc tat ccg acg gac          3162
Glu Gly Asp Asp His Gly Pro Gly Thr Tyr Thr Tyr Pro Thr Asp
1015                1020                1025 aaa gtt ttc aag ccc ggt gtt ttc gac ctc ctc aag ttc aag gtg          3207
Lys Val Phe Lys Pro Gly Val Phe Asp Leu Leu Lys Phe Lys Val
                1030                1035                1040 acc gag gga agc gac gac tgg acg ctg gag ttc cac ttc aaa gac          3252
Thr Glu Gly Ser Asp Asp Trp Thr Leu Glu Phe His Phe Lys Asp
            1045                1050                1055 ctc ggt gga aac ccg tgg aac ggg ccg aac ggc ttc agc ctg cag          3297
Leu Gly Gly Asn Pro Trp Asn Gly Pro Asn Gly Phe Ser Leu Gln
        1060                1065                1070 ata atc gag gta tac ttc gac ttc aag gag ggc ggg aac gtc tcg          3342
```

```
Ile Ile Glu Val Tyr Phe Asp Phe Lys Glu Gly Gly Asn Val Ser
        1075              1080              1085 gcc att aag atg ttc ccg gat ggg ccc gga agc aac gtc cgt ctt    3387
Ala Ile Lys Met Phe Pro Asp Gly Pro Gly Ser Asn Val Arg Leu
        1090              1095              1100 gat cca aat cac cca tgg gac ctg gcg ctt agg ata gcc ggc tgg    3432
Asp Pro Asn His Pro Trp Asp Leu Ala Leu Arg Ile Ala Gly Trp
        1105              1110              1115 gac tac gga aac ctg ata att ctg ccc gac gga acc gcc tac caa    3477
Asp Tyr Gly Asn Leu Ile Ile Leu Pro Asp Gly Thr Ala Tyr Gln
        1120              1125              1130 ggc gag atg cag att tcc gca gat ccg gtt aag aac gcc ata ata    3522
Gly Glu Met Gln Ile Ser Ala Asp Pro Val Lys Asn Ala Ile Ile
        1135              1140              1145 gtc aag gtt cca aag aag tac ctg aac ata tcc gac tac gga ctc    3567
Val Lys Val Pro Lys Lys Tyr Leu Asn Ile Ser Asp Tyr Gly Leu
        1150              1155              1160 tac acc gcc gtc atc gtg ggt tcc caa gac ggg tac ggc ccg gac    3612
Tyr Thr Ala Val Ile Val Gly Ser Gln Asp Gly Tyr Gly Pro Asp
        1165              1170              1175 aag tgg agg ccc gtg gcc gct gag gcc gag cag tgg aag ctc gga    3657
Lys Trp Arg Pro Val Ala Ala Glu Ala Glu Gln Trp Lys Leu Gly
        1180              1185              1190 ggc gca gac ccc cag gcg gtc ata gac aac ctc gta cca agg gtc    3702
Gly Ala Asp Pro Gln Ala Val Ile Asp Asn Leu Val Pro Arg Val
        1195              1200              1205 gtt gat gaa ctc gtg ccg gag ggc ttc aag cca acg cag gag gag    3747
Val Asp Glu Leu Val Pro Glu Gly Phe Lys Pro Thr Gln Glu Glu
        1210              1215              1220 cag ctg agc agc tac gac ctt gag aag aag acc ctg gcg acg gtg    3792
Gln Leu Ser Ser Tyr Asp Leu Glu Lys Lys Thr Leu Ala Thr Val
        1225              1230              1235 ctc atg gta ccg ctc gtc aat ggg act ggc ggc gag gaa cca acg    3837
Leu Met Val Pro Leu Val Asn Gly Thr Gly Gly Glu Glu Pro Thr
        1240              1245              1250 ccg acg gag agc cca acg gaa acg acg aca acc aca ccc agc gaa    3882
Pro Thr Glu Ser Pro Thr Glu Thr Thr Thr Thr Thr Pro Ser Glu
        1255              1260              1265 aca acc acc aca act tca acg acc acc ggc cca agc acg acg acc    3927
Thr Thr Thr Thr Thr Ser Thr Thr Thr Gly Pro Ser Thr Thr Thr
        1270              1275              1280 acc agc aca ccc ggc gga gga atc tgc ggc cca ggc att ata gcg    3972
Thr Ser Thr Pro Gly Gly Gly Ile Cys Gly Pro Gly Ile Ile Ala
        1285              1290              1295 ggc ctg gcc ctg ata ccg ctc ctc ctc aag agg agg aac tga        4014
Gly Leu Ala Leu Ile Pro Leu Leu Leu Lys Arg Arg Asn
        1300              1305              1310

<210> SEQ ID NO 11
<211> LENGTH: 1337
<212> TYPE: PRT
<213> ORGANISM: Thermococcus hydrothermalis

<400> SEQUENCE: 11

Met Arg Arg Val Val Ala Leu Phe Ile Ala Ile Leu Met Leu Gly Ser
        -25              -20              -15

Ile Val Gly Ala Asn Val Lys Ser Val Gly Ala Ala Glu Pro Lys Pro
        -10              -5          -1  1              5

Leu Asn Val Ile Ile Val Trp His Gln His Gln Pro Tyr Tyr Tyr Asp
                10              15              20
```

-continued

Pro Val Gln Asp Val Tyr Thr Arg Pro Trp Val Arg Leu His Ala Ala
           25                  30                  35

Asn Asn Tyr Trp Lys Met Ala His Tyr Leu Ser Gln Tyr Pro Glu Val
       40                  45                  50

His Ala Thr Ile Asp Leu Ser Gly Ser Leu Ile Ala Gln Leu Ala Asp
 55                  60                  65

Tyr Met Asn Gly Lys Lys Asp Thr Tyr Gln Ile Ile Thr Glu Lys Ile
70                  75                  80                  85

Ala Asn Gly Glu Pro Leu Thr Val Asp Glu Lys Trp Phe Met Leu Gln
               90                  95                 100

Ala Pro Gly Gly Phe Phe Asp Asn Thr Ile Pro Trp Asn Gly Glu Pro
              105                 110                 115

Ile Thr Asp Pro Asn Gly Asn Pro Ile Arg Asp Phe Trp Asp Arg Tyr
          120                 125                 130

Thr Glu Leu Lys Asn Lys Met Leu Ser Ala Lys Ala Lys Tyr Ala Asn
          135                 140                 145

Phe Val Thr Glu Ser Gln Lys Val Ala Val Thr Asn Glu Phe Thr Glu
150                 155                 160                 165

Gln Asp Tyr Ile Asp Leu Ala Val Leu Phe Asn Leu Ala Trp Ile Asp
              170                 175                 180

Tyr Asn Tyr Ile Thr Ser Thr Pro Glu Phe Lys Ala Leu Tyr Asp Lys
              185                 190                 195

Val Asp Glu Gly Gly Tyr Thr Arg Ala Asp Val Lys Thr Val Leu Asp
              200                 205                 210

Ala Gln Ile Trp Leu Leu Asn His Thr Phe Glu His Glu Lys Ile
    215                 220                 225

Asn Leu Leu Leu Gly Asn Gly Asn Val Glu Val Thr Val Pro Tyr
230                 235                 240                 245

Ala His Pro Ile Gly Pro Ile Leu Asn Asp Phe Gly Trp Asp Ser Asp
              250                 255                 260

Phe Asn Asp Gln Val Lys Lys Ala Asp Glu Leu Tyr Lys Pro Tyr Leu
              265                 270                 275

Gly Gly Gly Thr Ala Val Pro Lys Gly Gly Trp Ala Ala Glu Ser Ala
              280                 285                 290

Leu Asn Asp Lys Thr Leu Glu Ile Leu Ala Glu Asn Gly Trp Glu Trp
              295                 300                 305

Val Met Thr Asp Gln Met Val Leu Gly Lys Leu Gly Ile Glu Gly Thr
310                 315                 320                 325

Val Glu Asn Tyr His Lys Pro Trp Val Ala Glu Phe Asn Gly Lys Lys
              330                 335                 340

Ile Tyr Leu Phe Pro Arg Asn His Asp Leu Ser Asp Arg Val Gly Phe
              345                 350                 355

Thr Tyr Ser Gly Met Asn Gln Gln Gln Ala Val Glu Asp Phe Val Asn
              360                 365                 370

Glu Leu Leu Lys Leu Gln Lys Gln Asn Tyr Asp Gly Ser Leu Val Tyr
              375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
              410                 415                 420

Glu Gln Gly Leu Ile Arg Thr Leu Thr Pro Ser Glu Tyr Ile Gln Leu
              425                 430                 435

```
Tyr Gly Asp Lys Ala Asn Lys Leu Thr Pro Arg Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
                505                 510                 515

Met Glu Asn Lys Asp Lys Met Ser Gln Ala Asp Trp Glu Lys Ala Tyr
                520                 525                 530

Glu Tyr Leu Leu Arg Ala Glu Ala Ser Asp Trp Phe Trp Trp Tyr Gly
        535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
                585                 590                 595

Gly Leu Val Gly Leu Lys Asp Gly Glu Met Lys Asn Phe Ser Ser Met
                600                 605                 610

Ser Pro Leu Ala Lys Gly Val Ser Val Tyr Phe Asp Gly Glu Gly Ile
                615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
                665                 670                 675

Gly Leu Leu Ile Thr Lys His Val Val Tyr Glu Asn Gly Lys Ala Glu
                680                 685                 690

Ile Tyr Gly Ala Thr Asp Tyr Glu Lys Ser Glu Lys Leu Gly Glu Ala
        695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
                745                 750                 755

Thr Glu Val Lys Gly Val Val Ile Ala Asp Ile Thr Asp Pro Glu Gly
                760                 765                 770

Asp Asp His Gly Pro Gly Asn Tyr Thr Tyr Pro Thr Asp Lys Val Phe
                775                 780                 785

Lys Pro Gly Val Phe Asp Leu Leu Arg Phe Arg Met Leu Glu Gln Thr
790                 795                 800                 805

Glu Ser Tyr Val Met Glu Phe Tyr Phe Lys Asp Leu Gly Gly Asn Pro
                810                 815                 820

Trp Asn Gly Pro Asn Gly Phe Ser Leu Gln Ile Ile Glu Val Tyr Leu
                825                 830                 835

Asp Phe Lys Asp Gly Asn Ser Ser Ala Ile Lys Met Phe Pro Asp
                840                 845                 850

Gly Pro Gly Ala Asn Val Asn Leu Asp Pro Glu His Pro Trp Asp Val
```

```
            855                 860                 865
Ala Phe Arg Ile Ala Gly Trp Asp Tyr Gly Asn Leu Ile Ile Leu Pro
870                 875                 880                 885

Asn Gly Thr Ala Ile Gln Gly Glu Met Gln Ile Ser Ala Asp Pro Val
                890                 895                 900

Lys Asn Ala Ile Ile Val Lys Val Pro Lys Lys Tyr Ile Ala Ile Asn
                905                 910                 915

Glu Asp Tyr Gly Leu Trp Gly Asp Val Leu Val Gly Ser Gln Asp Gly
            920                 925                 930

Tyr Gly Pro Asp Lys Trp Arg Thr Ala Ala Val Asp Ala Glu Gln Trp
            935                 940                 945

Lys Leu Gly Gly Ala Asp Pro Gln Ala Val Ile Asn Gly Val Ala Pro
950                 955                 960                 965

Arg Val Ile Asp Glu Leu Val Pro Gln Gly Phe Glu Pro Thr Gln Glu
                970                 975                 980

Glu Gln Leu Ser Ser Tyr Asp Ala Asn Asp Met Lys Leu Ala Thr Val
                985                 990                 995

Lys Ala Leu Leu Leu Leu Lys Gln Gly Ile Val Val Thr Asp Pro
            1000                1005                1010

Glu Gly Asp Asp His Gly Pro Gly Thr Tyr Thr Tyr Pro Thr Asp
        1015                1020                1025

Lys Val Phe Lys Pro Gly Val Phe Asp Leu Leu Lys Phe Lys Val
1030                1035                1040

Thr Glu Gly Ser Asp Asp Trp Thr Leu Glu Phe His Phe Lys Asp
1045                1050                1055

Leu Gly Gly Asn Pro Trp Asn Gly Pro Asn Gly Phe Ser Leu Gln
1060                1065                1070

Ile Ile Glu Val Tyr Phe Asp Phe Lys Glu Gly Gly Asn Val Ser
1075                1080                1085

Ala Ile Lys Met Phe Pro Asp Gly Pro Gly Ser Asn Val Arg Leu
1090                1095                1100

Asp Pro Asn His Pro Trp Asp Leu Ala Leu Arg Ile Ala Gly Trp
1105                1110                1115

Asp Tyr Gly Asn Leu Ile Ile Leu Pro Asp Gly Thr Ala Tyr Gln
1120                1125                1130

Gly Glu Met Gln Ile Ser Ala Asp Pro Val Lys Asn Ala Ile Ile
1135                1140                1145

Val Lys Val Pro Lys Lys Tyr Leu Asn Ile Ser Asp Tyr Gly Leu
1150                1155                1160

Tyr Thr Ala Val Ile Val Gly Ser Gln Asp Gly Tyr Gly Pro Asp
1165                1170                1175

Lys Trp Arg Pro Val Ala Ala Glu Ala Glu Gln Trp Lys Leu Gly
1180                1185                1190

Gly Ala Asp Pro Gln Ala Val Ile Asp Asn Leu Val Pro Arg Val
1195                1200                1205

Val Asp Glu Leu Val Pro Glu Gly Phe Lys Pro Thr Gln Glu Glu
1210                1215                1220

Gln Leu Ser Ser Tyr Asp Leu Glu Lys Lys Thr Leu Ala Thr Val
1225                1230                1235

Leu Met Val Pro Leu Val Asn Gly Thr Gly Gly Glu Glu Pro Thr
1240                1245                1250

Pro Thr Glu Ser Pro Thr Glu Thr Thr Thr Thr Thr Pro Ser Glu
1255                1260                1265
```

-continued

```
Thr Thr Thr  Thr Thr Ser Thr Thr  Thr Gly Pro Ser Ser  Thr Thr
1270             1275                  1280

Thr Ser Thr  Pro Gly Gly Gly Ile  Cys Gly Pro Gly Ile  Ile Ala
1285             1290                  1295

Gly Leu Ala  Leu Ile Pro Leu Leu  Leu Lys Arg Arg Asn
1300             1305                  1310

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

Met Lys Lys Pro Leu Gly Lys Ile Val Ala Ser Thr Ala Leu Leu Ile
        -25                 -20                 -15

Ser Val Ala Phe Ser Ser Ile Ala Ser Ala Glu Glu Pro Lys Pro
    -10                  -5             -1   1               5

Leu Asn Val Ile Ile Val Trp His Gln His Gln Pro Tyr Tyr Tyr Asp
                 10                  15                  20

Pro Ile Gln Asp Ile Tyr Thr Arg Pro Trp Val Arg Leu His Ala Ala
             25                  30                  35

Asn Asn Tyr Trp Lys Met Ala Asn Tyr Leu Ser Lys Tyr Pro Asp Val
         40                  45                  50

His Val Ala Ile Asp Leu Ser Gly Ser Leu Ile Ala Gln Leu Ala Asp
     55                  60                  65

Tyr Met Asn Gly Lys Lys Asp Thr Tyr Gln Ile Val Thr Glu Lys Ile
 70                  75                  80                  85

Ala Asn Gly Glu Pro Leu Thr Leu Glu Asp Lys Trp Phe Met Leu Gln
                 90                  95                 100

Ala Pro Gly Gly Phe Phe Asp His Thr Ile Pro Trp Asn Gly Glu Pro
             105                 110                 115

Val Ala Asp Glu Asn Gly Asn Pro Tyr Arg Glu Gln Trp Asp Arg Tyr
         120                 125                 130

Ala Glu Leu Lys Asp Lys Arg Asn Asn Ala Phe Lys Lys Tyr Ala Asn
     135                 140                 145

Leu Pro Leu Asn Glu Gln Lys Val Lys Ile Thr Ala Glu Phe Thr Glu
150                 155                 160                 165

Gln Asp Tyr Ile Asp Leu Ala Val Leu Phe Asn Leu Ala Trp Ile Asp
                 170                 175                 180

Tyr Asn Tyr Ile Ile Asn Thr Pro Glu Leu Lys Ala Leu Tyr Asp Lys
             185                 190                 195

Val Asp Val Gly Gly Tyr Thr Lys Glu Asp Val Ala Thr Val Leu Lys
         200                 205                 210

His Gln Met Trp Leu Leu Asn His Thr Phe Glu His Glu Lys Ile
     215                 220                 225

Asn Tyr Leu Leu Gly Asn Gly Asn Val Glu Val Thr Val Val Pro Tyr
230                 235                 240                 245

Ala His Pro Ile Gly Pro Leu Leu Asn Asp Phe Gly Trp Tyr Glu Asp
```

-continued

```
              250                 255                 260
Phe Asp Ala His Val Lys Lys Ala His Glu Leu Tyr Lys Lys Tyr Leu
            265                 270                 275
Gly Asp Asn Arg Val Glu Pro Gln Gly Gly Trp Ala Ala Glu Ser Ala
            280                 285                 290
Leu Asn Asp Lys Thr Leu Glu Ile Leu Thr Asn Asn Gly Trp Lys Trp
            295                 300                 305
Val Met Thr Asp Gln Met Val Leu Asp Ile Leu Gly Ile Pro Asn Thr
310                 315                 320                 325
Val Glu Asn Tyr Tyr Lys Pro Trp Val Ala Glu Phe Asn Gly Lys Lys
                330                 335                 340
Ile Tyr Leu Phe Pro Arg Asn His Asp Leu Ser Asp Arg Val Gly Phe
                345                 350                 355
Arg Tyr Ser Gly Met Asn Gln Tyr Gln Ala Val Glu Asp Phe Val Asn
                360                 365                 370
Glu Leu Leu Lys Val Gln Lys Glu Asn Tyr Asp Gly Ser Leu Val Tyr
            375                 380                 385
Val Val Thr Leu Asp Gly Glu Asn Pro Trp Glu His Tyr Pro Phe Asp
390                 395                 400                 405
Gly Lys Ile Phe Leu Glu Glu Leu Tyr Lys Lys Leu Thr Glu Leu Gln
                410                 415                 420
Lys Gln Gly Leu Ile Arg Thr Val Thr Pro Ser Glu Tyr Ile Gln Met
            425                 430                 435
Tyr Gly Asp Lys Ala Asn Lys Leu Thr Pro Arg Met Met Glu Arg Leu
            440                 445                 450
Asp Leu Thr Gly Asp Asn Val Asn Ala Leu Leu Lys Ala Gln Ser Leu
        455                 460                 465
Gly Glu Leu Tyr Asp Met Thr Gly Val Lys Glu Met Gln Trp Pro
470                 475                 480                 485
Glu Ser Ser Trp Ile Asp Gly Thr Leu Ser Thr Trp Ile Gly Glu Pro
                490                 495                 500
Gln Glu Asn Tyr Gly Trp Tyr Trp Leu Tyr Met Ala Arg Lys Ala Leu
            505                 510                 515
Met Glu Asn Lys Asp Lys Met Ser Gln Ala Asp Trp Glu Lys Ala Tyr
        520                 525                 530
Glu Tyr Leu Leu Arg Ala Glu Ala Ser Asp Trp Phe Trp Trp Tyr Gly
            535                 540                 545
Ser Asp Gln Asp Ser Gly Gln Asp Tyr Thr Phe Asp Arg Tyr Leu Lys
550                 555                 560                 565
Thr Tyr Leu Tyr Glu Met Tyr Lys Leu Ala Gly Val Glu Pro Pro Ser
                570                 575                 580
Tyr Leu Phe Gly Asn Tyr Phe Pro Asp Gly Glu Pro Tyr Thr Thr Arg
            585                 590                 595
Gly Leu Val Gly Leu Lys Asp Gly Glu Met Lys Asn Phe Ser Ser Met
            600                 605                 610
Ser Pro Leu Ala Lys Gly Val Ser Val Tyr Phe Asp Gly Glu Gly Ile
            615                 620                 625
His Phe Ile Val Lys Gly Asn Leu Asp Arg Phe Glu Val Ser Ile Trp
630                 635                 640                 645
Glu Lys Asp Glu Arg Val Gly Asn Thr Phe Thr Arg Leu Gln Glu Lys
                650                 655                 660
Pro Asp Glu Leu Ser Tyr Phe Met Phe Pro Phe Ser Arg Asp Ser Val
            665                 670                 675
```

```
Gly Leu Leu Ile Thr Lys His Val Tyr Glu Asn Gly Lys Ala Glu
            680                 685                 690

Ile Tyr Gly Ala Thr Asp Tyr Glu Lys Ser Glu Lys Leu Gly Glu Ala
    695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
                745                 750                 755

Thr Glu Val Lys Gly Val Val Ile Ala Asp Ile Thr Asp Pro Glu Gly
            760                 765                 770

Asp Asp His Gly Pro Gly Asn Tyr Thr
            775                 780

<210> SEQ ID NO 13
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 13

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240
```

```
Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 14
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: mature Penicillium oxalicum glucoamylase
      sequence

<400> SEQUENCE: 14

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175
```

```
Ala Tyr Val Gly Gln Tyr Trp Asn Asn Thr Gly Phe Asp Leu Trp Glu
                180                 185                 190

Glu Val Asp Gly Ser Ser Phe Phe Thr Ile Ala Val Gln His Arg Ala
            195                 200                 205

Leu Val Glu Gly Ser Gln Leu Ala Lys Lys Leu Gly Lys Ser Cys Asp
        210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
```

-continued

595

<210> SEQ ID NO 15
<211> LENGTH: 573
<212> TYPE: PRT
<213> ORGANISM: Gloeophyllum sepiarium

<400> SEQUENCE: 15

```
Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365
```

```
Thr Ser Leu Ala Phe Phe Gln Gln Phe Ser Ser Gly Val Thr Ala Gly
370                 375                 380

Thr Tyr Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
            405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
                435                 440                 445

Phe Glu Ala Arg Asn Asn Thr Gln Phe Ala Gly Trp Gly Ala Ala Gly
450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
            485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
                515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570
```

<210> SEQ ID NO 16
<211> LENGTH: 583
<212> TYPE: PRT
<213> ORGANISM: Rhizomucor pusillus

<400> SEQUENCE: 16

```
Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175
```

```
Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Thr Ala Thr Pro
        435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580
```

```
<210> SEQ ID NO 17
<211> LENGTH: 559
<212> TYPE: PRT
<213> ORGANISM: Gloephyllum trabeum
<220> FEATURE:
<221> NAME/KEY: SIGNAL
<222> LOCATION: (1)..(17)
<220> FEATURE:
<221> NAME/KEY: mat_peptide
<222> LOCATION: (18)..(576)

<400> SEQUENCE: 17

Gln Ser Val Asp Ser Tyr Val Gly Ser Glu Gly Pro Ile Ala Lys Ala
        -15                 -10                  -5

Gly Val Leu Ala Asn Ile Gly Pro Asn Gly Ser Lys Ala Ser Gly Ala
 -1   1               5                  10                  15

Ala Ala Gly Val Val Ala Ser Pro Ser Lys Ser Asp Pro Asp Tyr
                 20                  25                  30

Trp Tyr Thr Trp Thr Arg Asp Ser Ser Leu Val Phe Lys Ser Leu Ile
             35                  40                  45

Asp Gln Tyr Thr Thr Gly Ile Asp Ser Thr Ser Ser Leu Arg Ser Leu
         50                  55                  60

Ile Asp Ser Phe Val Ile Ala Glu Ala Asn Ile Gln Gln Val Ser Asn
 65                  70                  75

Pro Ser Gly Thr Leu Thr Thr Gly Gly Leu Gly Glu Pro Lys Phe Asn
 80                  85                  90                  95

Val Asp Glu Thr Ala Phe Thr Gly Ala Trp Gly Arg Pro Gln Arg Asp
                100                 105                 110

Gly Pro Ala Leu Arg Ala Thr Ala Leu Ile Thr Tyr Gly Asn Trp Leu
                115                 120                 125

Leu Ser Asn Gly Asn Thr Thr Trp Val Thr Ser Thr Leu Trp Pro Ile
                130                 135                 140

Ile Gln Asn Asp Leu Asn Tyr Val Val Gln Tyr Trp Asn Gln Thr Thr
                145                 150                 155

Phe Asp Leu Trp Glu Glu Val Asn Ser Ser Ser Phe Phe Thr Thr Ala
160                 165                 170                 175

Val Gln His Arg Ala Leu Arg Glu Gly Ala Ala Phe Ala Thr Lys Ile
                180                 185                 190

Gly Gln Thr Ser Ser Val Ser Tyr Thr Thr Gln Ala Ala Asn Leu
                195                 200                 205

Leu Cys Phe Leu Gln Ser Tyr Trp Asn Pro Thr Ser Gly Tyr Ile Thr
                210                 215                 220

Ala Asn Thr Gly Gly Gly Arg Ser Gly Lys Asp Ala Asn Thr Leu Leu
                225                 230                 235

Ala Ser Ile His Thr Tyr Asp Pro Ser Ala Gly Cys Asp Ala Thr Thr
240                 245                 250                 255

Phe Gln Pro Cys Ser Asp Lys Ala Leu Ser Asn Leu Lys Val Tyr Val
                260                 265                 270

Asp Ser Phe Arg Ser Val Tyr Ser Ile Asn Ser Gly Ile Ala Ser Asn
                275                 280                 285

Ala Ala Val Ala Thr Gly Arg Tyr Pro Glu Asp Ser Tyr Gln Gly Gly
                290                 295                 300

Asn Pro Trp Tyr Leu Thr Thr Phe Ala Val Ala Glu Gln Leu Tyr Asp
                305                 310                 315

Ala Leu Asn Val Trp Ala Ala Gln Gly Ser Leu Asn Val Thr Ser Ile
320                 325                 330                 335
```

Ser Leu Pro Phe Phe Gln Gln Phe Ser Ser Val Thr Ala Gly Thr
            340                 345                 350

Tyr Ala Ser Ser Thr Thr Tyr Thr Thr Leu Thr Ser Ala Ile Lys
        355                 360                 365

Ser Phe Ala Asp Gly Phe Val Ala Ile Asn Ala Gln Tyr Thr Pro Ser
    370                 375                 380

Asn Gly Gly Leu Ala Glu Gln Phe Ser Arg Ser Asn Gly Ala Pro Val
385                 390                 395

Ser Ala Val Asp Leu Thr Trp Ser Tyr Ala Ser Ala Leu Thr Ala Phe
400                 405                 410                 415

Glu Ala Arg Asn Asn Thr Gln Phe Ala Gly Trp Gly Ala Val Gly Leu
                420                 425                 430

Thr Val Pro Thr Ser Cys Ser Ser Asn Ser Gly Gly Gly Gly Ser
            435                 440                 445

Thr Val Ala Val Thr Phe Asn Val Asn Ala Gln Thr Val Trp Gly Glu
            450                 455                 460

Asn Ile Tyr Ile Thr Gly Ser Val Asp Ala Leu Ser Asn Trp Ser Pro
465                 470                 475

Asp Asn Ala Leu Leu Ser Ser Ala Asn Tyr Pro Thr Trp Ser Ile
480                 485                 490                 495

Thr Val Asn Leu Pro Ala Ser Thr Ala Ile Gln Tyr Lys Tyr Ile Arg
            500                 505                 510

Lys Asn Asn Gly Ala Val Thr Trp Glu Ser Asp Pro Asn Asn Ser Ile
            515                 520                 525

Thr Thr Pro Ala Ser Gly Ser Val Thr Glu Asn Asp Thr Trp Arg
            530                 535                 540

<210> SEQ ID NO 18
<211> LENGTH: 573
<212> TYPE: PRT
<213> ORGANISM: Pycnoporus sanguineus

<400> SEQUENCE: 18

Met Arg Phe Thr Leu Leu Ala Ser Leu Ile Gly Leu Ala Val Gly Ala
1               5                   10                  15

Phe Ala Gln Ser Ser Ala Val Asp Ala Tyr Val Ala Ser Glu Ser Pro
            20                  25                  30

Ile Ala Lys Gln Gly Val Leu Asn Asn Ile Gly Pro Asn Gly Ser Lys
        35                  40                  45

Ala His Gly Ala Lys Ala Gly Ile Val Val Ala Ser Pro Ser Thr Glu
    50                  55                  60

Asn Pro Asp Tyr Leu Tyr Thr Trp Thr Arg Asp Ser Ser Leu Val Phe
65                  70                  75                  80

Lys Leu Leu Ile Asp Gln Phe Thr Ser Gly Asp Asp Thr Ser Leu Arg
                85                  90                  95

Gly Leu Ile Asp Asp Phe Thr Ser Ala Glu Ala Ile Leu Gln Gln Val
            100                 105                 110

Ser Asn Pro Ser Gly Thr Val Ser Thr Gly Gly Leu Gly Glu Pro Lys
        115                 120                 125

Phe Asn Ile Asp Glu Thr Ala Phe Thr Gly Ala Trp Gly Arg Pro Gln
    130                 135                 140

Arg Asp Gly Pro Ala Leu Arg Ala Thr Ser Ile Ile Arg Tyr Ala Asn
145                 150                 155                 160

Trp Leu Leu Asp Asn Gly Asn Thr Thr Tyr Val Ser Asn Thr Leu Trp

```
                    165                 170                 175
Pro Val Ile Gln Leu Asp Leu Asp Tyr Val Ala Asp Asn Trp Asn Gln
                180                 185                 190

Ser Thr Phe Asp Leu Trp Glu Glu Val Asp Ser Ser Phe Phe Thr
            195                 200                 205

Thr Ala Val Gln His Arg Ala Leu Arg Glu Gly Ala Thr Phe Ala Ser
        210                 215                 220

Arg Ile Gly Gln Ser Ser Val Val Ser Gly Tyr Thr Thr Gln Ala Asp
225                 230                 235                 240

Asn Leu Leu Cys Phe Leu Gln Ser Tyr Trp Asn Pro Ser Gly Gly Tyr
                245                 250                 255

Val Thr Ala Asn Thr Gly Gly Arg Ser Gly Lys Asp Ser Asn Thr
            260                 265                 270

Val Leu Thr Ser Ile His Thr Phe Asp Pro Ala Ala Gly Cys Asp Ala
        275                 280                 285

Ala Thr Phe Gln Pro Cys Ser Asp Lys Ala Leu Ser Asn Leu Lys Val
        290                 295                 300

Tyr Val Asp Ala Phe Arg Ser Ile Tyr Thr Ile Asn Asn Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Tyr Val Trp Asp Gln Leu Gly Gly Leu Asn Val Thr
        355                 360                 365

Ser Thr Ser Leu Ala Phe Phe Gln Gln Phe Ala Ser Gly Leu Ser Thr
    370                 375                 380

Gly Thr Tyr Ser Ala Ser Ser Thr Tyr Ala Thr Leu Thr Ser Ala
385                 390                 395                 400

Ile Arg Ser Phe Ala Asp Gly Phe Leu Ala Ile Asn Ala Lys Tyr Thr
                405                 410                 415

Pro Ala Asp Gly Gly Leu Ala Glu Gln Tyr Ser Arg Asn Asp Gly Thr
            420                 425                 430

Pro Leu Ser Ala Val Asp Leu Thr Trp Ser Tyr Ala Ala Ala Leu Thr
        435                 440                 445

Ala Phe Ala Ala Arg Glu Gly Lys Thr Tyr Gly Ser Trp Gly Ala Ala
        450                 455                 460

Gly Leu Thr Val Pro Ala Ser Cys Ser Gly Gly Gly Ala Thr Val
465                 470                 475                 480

Ala Val Thr Phe Asn Val Gln Ala Thr Thr Val Phe Gly Glu Asn Ile
                485                 490                 495

Tyr Ile Thr Gly Ser Val Ala Ala Leu Gln Asn Trp Ser Pro Asp Asn
            500                 505                 510

Ala Leu Ile Leu Ser Ala Ala Asn Tyr Pro Thr Trp Ser Ile Thr Val
        515                 520                 525

Asn Leu Pro Ala Asn Thr Val Val Gln Tyr Lys Tyr Ile Arg Lys Phe
        530                 535                 540

Asn Gly Gln Val Thr Trp Glu Ser Asp Pro Asn Asn Gln Ile Thr Thr
545                 550                 555                 560

Pro Ser Gly Gly Ser Phe Thr Gln Asn Asp Val Trp Arg
                565                 570

<210> SEQ ID NO 19
```

-continued

```
<211> LENGTH: 618
<212> TYPE: PRT
<213> ORGANISM: Talaromyces emersonii

<400> SEQUENCE: 19

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
            20                  25                  30

Asp Ser Phe Leu Ala Thr Glu Thr Pro Ile Ala Leu Gln Gly Val Leu
        35                  40                  45

Asn Asn Ile Gly Pro Asn Gly Ala Asp Val Ala Gly Ala Ser Ala Gly
    50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
    210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
        275                 280                 285

Gly Gly Cys Asp Asp Ser Thr Phe Gln Pro Cys Ser Ala Arg Ala Leu
    290                 295                 300

Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro
                325                 330                 335

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
        355                 360                 365

Ser Ile Ser Ile Thr Asp Val Ser Leu Pro Phe Phe Gln Asp Ile Tyr
    370                 375                 380

Pro Ser Ala Ala Val Gly Thr Tyr Asn Ser Gly Ser Thr Thr Phe Asn
```

```
                385                 390                 395                 400
Asp Ile Ile Ser Ala Val Gln Thr Tyr Gly Asp Gly Tyr Leu Ser Ile
                    405                 410                 415
Val Glu Lys Tyr Thr Pro Ser Asp Gly Ser Leu Thr Glu Gln Phe Ser
                420                 425                 430
Arg Thr Asp Gly Thr Pro Leu Ser Ala Ser Ala Leu Thr Trp Ser Tyr
                435                 440                 445
Ala Ser Leu Leu Thr Ala Ser Ala Arg Arg Gln Ser Val Val Pro Ala
            450                 455                 460
Ser Trp Gly Glu Ser Ser Ala Ser Ser Val Pro Ala Val Cys Ser Ala
465                 470                 475                 480
Thr Ser Ala Thr Gly Pro Tyr Ser Thr Ala Thr Asn Thr Val Trp Pro
                    485                 490                 495
Ser Ser Gly Ser Gly Ser Ser Thr Thr Thr Ser Ser Ala Pro Cys Thr
                500                 505                 510
Thr Pro Thr Ser Val Ala Val Thr Phe Asp Glu Ile Val Ser Thr Ser
            515                 520                 525
Tyr Gly Glu Thr Ile Tyr Leu Ala Gly Ser Ile Pro Glu Leu Gly Asn
        530                 535                 540
Trp Ser Thr Ala Ser Ala Ile Pro Leu Arg Ala Asp Ala Tyr Thr Asn
545                 550                 555                 560
Ser Asn Pro Leu Trp Tyr Val Thr Val Asn Leu Pro Pro Gly Thr Ser
                    565                 570                 575
Phe Glu Tyr Lys Phe Lys Asn Gln Thr Asp Gly Thr Ile Val Trp
                580                 585                 590
Glu Asp Pro Asn Arg Ser Tyr Thr Val Pro Ala Tyr Cys Gly Gln
        595                 600                 605
Thr Thr Ala Ile Leu Asp Asp Ser Trp Gln
    610                 615

<210> SEQ ID NO 20
<211> LENGTH: 574
<212> TYPE: PRT
<213> ORGANISM: Trametes cingulata

<400> SEQUENCE: 20

Met Arg Phe Thr Leu Leu Thr Ser Leu Leu Gly Leu Ala Leu Gly Ala
1               5                   10                  15
Phe Ala Gln Ser Ser Ala Ala Asp Ala Tyr Val Ala Ser Glu Ser Pro
                20                  25                  30
Ile Ala Lys Ala Gly Val Leu Ala Asn Ile Gly Pro Ser Gly Ser Lys
            35                  40                  45
Ser Asn Gly Ala Lys Ala Gly Ile Val Ile Ala Ser Pro Ser Thr Ser
        50                  55                  60
Asn Pro Asn Tyr Leu Tyr Thr Trp Thr Arg Asp Ser Ser Leu Val Phe
65                  70                  75                  80
Lys Ala Leu Ile Asp Gln Phe Thr Thr Gly Glu Asp Thr Ser Leu Arg
                85                  90                  95
Thr Leu Ile Asp Glu Phe Thr Ser Ala Glu Ala Ile Leu Gln Gln Val
                100                 105                 110
Pro Asn Pro Ser Gly Thr Val Ser Thr Gly Gly Leu Gly Glu Pro Lys
            115                 120                 125
Phe Asn Ile Asp Glu Thr Ala Phe Thr Asp Ala Trp Gly Arg Pro Gln
        130                 135                 140
```

```
Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
            180                 185                 190

Ser Thr Phe Asp Leu Trp Glu Glu Ile Asn Ser Ser Phe Phe Thr
        195                 200                 205

Thr Ala Val Gln His Arg Ala Leu Arg Glu Gly Ala Thr Phe Ala Asn
    210                 215                 220

Arg Ile Gly Gln Thr Ser Val Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Arg Ser Gly Lys Asp Ala Asn Thr
            260                 265                 270

Val Leu Thr Ser Ile His Thr Phe Asp Pro Ala Ala Gly Cys Asp Ala
    275                 280                 285

Val Thr Phe Gln Pro Cys Ser Asp Lys Ala Leu Ser Asn Leu Lys Val
    290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Ile Val Trp Asn Lys Leu Gly Ala Leu Asn Val Thr
    355                 360                 365

Ser Thr Ser Leu Pro Phe Phe Gln Gln Phe Ser Ser Gly Val Thr Val
    370                 375                 380

Gly Thr Tyr Ala Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
        435                 440                 445

Ser Phe Ala Ala Arg Ser Gly Lys Thr Tyr Ala Ser Trp Gly Ala Ala
    450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
                485                 490                 495

Ile Tyr Ile Thr Gly Ser Val Pro Ala Leu Gln Asn Trp Ser Pro Asp
            500                 505                 510

Asn Ala Leu Ile Leu Ser Ala Ala Asn Tyr Pro Thr Trp Ser Ile Thr
        515                 520                 525

Val Asn Leu Pro Ala Ser Thr Thr Ile Glu Tyr Lys Tyr Ile Arg Lys
    530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
```

```
                565                 570

<210> SEQ ID NO 21
<211> LENGTH: 483
<212> TYPE: PRT
<213> ORGANISM: Bacillus licheniformis

<400> SEQUENCE: 21

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365
```

-continued

```
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
        435                 440                 445
Trp His Asp Ile Thr Gly Asn Arg Ser Glu Pro Val Val Ile Asn Ser
    450                 455                 460
Glu Gly Trp Gly Glu Phe His Val Asn Gly Gly Ser Val Ser Ile Tyr
465                 470                 475                 480
Val Gln Arg
```

<210> SEQ ID NO 22
<211> LENGTH: 25
<212> TYPE: DNA
<213> ORGANISM: Artificial Sequence
<220> FEATURE:
<223> OTHER INFORMATION: Sense Primer

<400> SEQUENCE: 22
atgcgtctca ctctattatc aggtg                                        25

<210> SEQ ID NO 23
<211> LENGTH: 39
<212> TYPE: DNA
<213> ORGANISM: Artificial Sequence
<220> FEATURE:
<223> OTHER INFORMATION: Primer F

<400> SEQUENCE: 23
acacaactgg ggatccacca tgcgtctcac tctattatc                         39

<210> SEQ ID NO 24
<211> LENGTH: 37
<212> TYPE: DNA
<213> ORGANISM: Artificial Sequence
<220> FEATURE:
<223> OTHER INFORMATION: Primer R

<400> SEQUENCE: 24
agatctcgag aagcttaaaa ctgccacacg tcgttgg                           37

<210> SEQ ID NO 25
<211> LENGTH: 18
<212> TYPE: DNA
<213> ORGANISM: Artificial Sequence
<220> FEATURE:
<223> OTHER INFORMATION: Primer K79V F

<400> SEQUENCE: 25
gcagtctttc caattgac                                                18

<210> SEQ ID NO 26
<211> LENGTH: 18
<212> TYPE: DNA
<213> ORGANISM: Artificial Sequence
<220> FEATURE:
<223> OTHER INFORMATION: Primer K79V R

```
<400> SEQUENCE: 26
aattggaaag actgcccg                                                        18

<210> SEQ ID NO 27
<211> LENGTH: 39
<212> TYPE: DNA
<213> ORGANISM: Artificial Sequence
<220> FEATURE:
<223> OTHER INFORMATION: Primer F-NP003940

<400> SEQUENCE: 27
acacaactgg ggatccacca tgcgtctcac tctattatc                                 39

<210> SEQ ID NO 28
<211> LENGTH: 37
<212> TYPE: DNA
<213> ORGANISM: Artificial Sequence
<220> FEATURE:
<223> OTHER INFORMATION: Primer R-NP003940

<400> SEQUENCE: 28
agatctcgag aagcttaaaa ctgccacacg tcgttgg                                   37
```

PROCESSES FOR PRODUCING ETHANOL AND YEAST

CROSS-REFERENCE TO RELATED APPLICATIONS

This application is a 35 U.S.C. 371 national application of PCT/US2015/021754, filed Mar. 20, 2015, which claims priority or the benefit under 35 U.S.C. 119 of Australian application no. 2014901009, filed Mar. 21, 2014; U.S. provisional application No. 62/021,276, filed Jul. 7, 2014; U.S. provisional application No. 62/078,198, filed Nov. 11, 2014; and U.S. provisional application No. 62/093,852, filed Dec. 18, 2014. The contents of these applications are fully incorporated herein by reference.

FIELD OF THE INVENTION

The present invention relates to processes, including a liquefaction step, for producing ethanol from starch-containing material using yeast for converting fermentable sugars into ethanol. The present invention also relates to a *Saccharomyces* strain having improved ability to ferment sugars to ethanol, to methods for the production of *Saccharomyces* strains having improved ability to ferment sugars to ethanol, and the use of *Saccharomyces* yeast strains having improved ability to ferment sugars to ethanol in the production of ethanol. The invention also relates to processes for recovering/extracting oil from the backend of an ethanol production process using a *Saccharomyces* strain of the invention. Finally the invention relates to compositions comprising a *Saccharomyces* yeast strain of the invention and naturally occurring and/or non-naturally occurring components.

REFERENCE TO A SEQUENCE LISTING

This application contains a Sequence Listing in computer readable form. The computer readable form is incorporated herein by reference.

BACKGROUND OF THE INVENTION

Production of ethanol from starch-containing material is well-known in the art. The production of ethanol as a bio-fuel has become a major industry, with in excess of 21 billion gallons of ethanol being produced worldwide in 2012.

The most commonly industrially used commercial process, often referred to as a "conventional process", includes liquefying gelatinized starch at high temperature (around 85° C.) using typically a bacterial alpha-amylase, followed by simultaneous saccharification and fermentation carried out anaerobically in the presence of a glucoamylase and a *Saccharomyces cerevisae* yeast.

Yeast which are used for production of ethanol for use as fuel, such as in the corn ethanol industry, require several characteristics to ensure cost effective production of the ethanol. These characteristics include ethanol tolerance, low by-product yield, rapid fermentation, and the ability to limit the amount of residual sugars remaining in the ferment. Such characteristics have a marked effect on the viability of the industrial process.

Yeast of the genus *Saccharomyces* exhibit many of the characteristics required for production of ethanol. In particular, strains of *Saccharomyces cerevisiae* are widely used for the production of ethanol in the fuel ethanol industry. Strains of *Saccharomyces cerevisiae* that are widely used in the fuel ethanol industry have the ability to produce high yields of ethanol under fermentation conditions found in, for example, the fermentation of corn mash. An example of such a strain is the yeast used in commercially available ethanol yeast product called Ethanol Red™.

Strains of *Saccharomyces cerevisiae* are used in the fuel ethanol industry to ferment sugars such as glucose, fructose, sucrose and maltose to produce ethanol via the glycolytic pathway. These sugars are obtained from sources such as corn and other grains, sugar juice, molasses, grape juice, fruit juices, and starchy root vegetables and may include the breakdown of cellulosic material into glucose.

Although strains of *Saccharomyces cerevisiae* currently used in the fuel ethanol industry are well suited to ethanol production, there is an increasing need for improvements in the efficiency of ethanol production owing to the increased demand for ethanol as a fuel, and the increased availability of starch in new strains of corn.

There is therefore a need for new strains of *Saccharomyces* capable of improving the efficiency of ethanol production in industrial scale fermentation. There is also a need for new strains of *Saccharomyces* that reduce the acetaldehyde level after fermentation compared to current commercial strains, such as ETHANOL RED™.

Further, despite significant improvement of ethanol production processes over the past decade there is still a desire and need for providing processes of producing ethanol from starch-containing material that can provide a higher ethanol yield.

SUMMARY OF THE INVENTION

The present invention relates to producing ethanol from starch-containing material using yeast.

In the first aspect the invention relates to processes for producing ethanol from starch-containing material comprising the steps of:

i) liquefying the starch-containing material at a temperature above the initial gelatinization temperature using an alpha-amylase;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851 or a derivative of *Saccharomyces* strain V14/004037 having defining characteristics of strain V14/004037.

According to the process of the invention the fermenting organism strain, especially *Saccharomyces cerevisiae* yeast, having properties that are about the same as that of *Saccharomyces cerevisiae* MBG4851 or a derivative of *Saccharomyces* strain V14/004037 (i.e., *Saccharomyces cerevisiae* MBG4851) having defining characteristics of strain V14/004037, has one or more, such as all, of the following properties and defining characteristics:

increases ethanol yield compared to Ethanol Red™ under the same process conditions;
produces reduced levels of lactic acid compared to Ethanol Red™ under the same process conditions;
produces reduced levels of glycerol compared to Ethanol Red™ under the same process conditions;
reduces the level of acetaldehyde in fermentation compared to Ethanol Red™ under the same process condition;

increases the oil yield compared to Ethanol Red™ under the same process conditions;

has faster fermentation kinetics compared to Ethanol Red™ under the same process conditions.

In an embodiment and in an aspect of the invention oil is recovered/extracted downstream from fermentation. The oil recovery/extraction may take place at the backend of the process of the invention, e.g., after ethanol recovery, such as from the thin stillage and/or syrup/evaporated centrate. Recovery may be done, e.g., by extraction, such as hexane extraction, or by using another oil recovery/extraction technology well-known in the art.

In an aspect the invention relates to processes for recovering/extracting oil from an ethanol production process of the invention comprising the steps of:

i) liquefying starch-containing material at a temperature above the initial gelatinization temperature using an alpha-amylase;
ii) saccharifying using a glucoamylase;
iii fermenting using a fermenting organism.
iv) recovering the fermentation product to form whole stillage;
v) separating the whole stillage into thin stillage and wet cake;
vi) optionally concentrating the thin stillage into syrup;

wherein oil is recovered/extracted downstream from fermentation step iii) and wherein the fermenting organism is Saccharomyces cerevisiae MBG4851 (deposited under Accession No. V14/004037 at National Measurement Institute, Victoria, Australia) or a fermenting organism strain having properties that are about the same as that of Saccharomyces cerevisiae MBG4851 or a derivative of Saccharomyces strain V14/004037 having defining characteristics of strain V14/004037.

In an embodiment a protease is added in saccharification and/or fermentation or SSF. As shown in Example 40 oil recovery/extraction is increased using MBG4851 and further increased when a protease, in particular a metallo protease, is present or added. Steps ii) and iii) are carried out either sequentially or simultaneously. In a preferred embodiment steps ii) and iii) are carried out simultaneously, i.e., simultaneous saccharification and fermentation (SSF).

According to the ethanol production process of the invention liquefaction in step i) is carried out by subjecting starch-containing material at a temperature above the initial gelatinization temperature, typically between 80-90° C., using an alpha-amylase. The pH in liquefaction is preferably between 4.5 and 6.0, such as between 4.8 and 5.8. Examples of alpha-amylase can be found below in the "Alpha-Amylase Present and/or Added During Liquefaction"-section. In an embodiment the alpha-amylase is a thermostable bacterial alpha-amylase. In a preferred embodiment the alpha-amylase is from the genus Bacillus, such as a strain of Bacillus stearothermophilus, in particular a variant of a Bacillus stearothermophilus alpha-amylase, such as the one shown in SEQ ID NO: 3 in WO 99/019467 or SEQ ID NO: 1 herein. Examples of suitable Bacillus stearothermophilus alpha-amylase variants can be found below in the "Thermostable Alpha-Amylase"-section and include one from the following group of Bacillus stearothermophilus alpha-amylase variants with the following mutations:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V;
I181*+G182*+N193F+V59A+E129V+K177L+R179E+Q254S+M284V; and
I181*+G182*+N193F+E129V+K177L+R179E+K220P+N224L+S242Q+Q254S (using SEQ ID NO: 1 for numbering).

Examples of other suitable Bacillus stearothermophilus alpha-amylases having increased thermostability compared to a reference alpha-amylase (Bacillus stearothermophilus alpha-amylase with the mutations I181*+G182*+N193F truncated to around 491 amino acids) at pH 4.5 and 5.5, 0.12 mM CaCl₂ can be found in WO 2011/082425 hereby incorporated by reference. (See also Example 1 below)

Liquefaction in step i) may be carried out using a combination of alpha-amylase and protease. The protease may be a protease having a thermostability value of more than 20% determined as Relative Activity at 80° C./70° C. Examples of suitable proteases are described below in the section "Protease Present and/or Added During Liquefaction".

The protease may be of fungal origin, such as of filamentous fungus origin. Specific examples of suitable fungal proteases are protease variants of metallo protease derived from a strain of the genus Thermoascus, preferably a strain of Thermoascus aurantiacus, especially the strain Thermoascus aurantiacus CGMCC No. 0670 disclosed as the mature part of SEQ ID NO. 2 disclosed in WO 2003/048353 or the mature part of SEQ ID NO: 1 in WO 2010/008841 or SEQ ID NO: 3 herein with the following mutations:

D79L+S87P+A112P+D142L:
D79L+S87P+D142L; or
A27K+D79L+Y82F+S87G+D104P+A112P+A126V+D142L.

Examples of other suitable protease variants can be found in WO 2011/072191 hereby incorporated by reference (See also Example 2 below).

Suitable proteases also include bacterial proteases. A suitable bacterial protease may be derived from a strain of Pyrococcus, preferably a strain of Pyrococcus furiosus. In a preferred embodiment the protease is the one shown in SEQ ID NO: 1 in U.S. Pat. No. 6,358,726 or SEQ ID NO: 13 herein.

In a preferred embodiment 0.5-50 micro gram Pyrococcus furiosus protease per gram DS, such as 1-5 micro gram Pyrococcus furiosus protease per gram DS, such as around 1.5 or 3 micro gram Pyrococcus furiosus protease per gram DS is present and/or added in liquefaction step i).

In an embodiment of the invention the alpha-amylase and/or the protease added in the liquefaction step i) is further combined with a glucoamylase. Thus, a glucoamylase may also be present and/or added during liquefaction step i). The glucoamylase is preferably thermostable. That means that the glucoamylase has a heat stability at 85° C., pH 5.3, of at least 20%, such as at least 30%, preferably at least 35% determined as described in Example 4 (heat stability). In an embodiment the glucoamylase present and/or added in liquefaction has a relative activity pH optimum at pH 5.0 of at least 90%, preferably at least 95%, preferably at least 97%. In an embodiment the glucoamylase has a pH stability at pH 5.0 of at least at least 80%, at least 85%, at least 90% determined as described in Example 4 (pH optimum).

A suitable glucoamylase present and/or added in liquefaction step i) may according to the invention be derived from a strain of the genus Penicillium, especially a strain of Penicillium oxalicum disclosed as SEQ ID NO: 2 in WO 2011/127802 or SEQ ID NOs: 9 or 14 herein. In a preferred embodiment the glucoamylase is a variant of the Penicillium oxalicum glucoamylase shown in SEQ ID NO: 2 in WO 2011/127802 having a K79V substitution (using the mature sequence shown in SEQ ID NO: 14 for numbering), such as a variant disclosed in WO 2013/053801. In a preferred embodiment the *Penicillium oxalicum* glucoamylase has a K79V substitution (using SEQ ID NO: 14 for numbering) and further one of the following:

P11F+T65A+Q327F;

P2N+P4S+P11F+T65A+Q327F (using SEQ ID NO: 14 for numbering).

Examples of other suitable *Penicillium oxalicum* glucoamylase variants can be found in WO 2013/053801 incorporated by reference (See also Example 15 below).

In an embodiment the glucoamylase, such as a *Penicillium oxalicum* glucoamylase variant, used in liquefaction has a thermostability determined as DSC Td at pH 4.0 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C. In an embodiment the glucoamylase, such as a *Penicillium oxalicum* glucoamylase variant has a thermostability determined as DSC Td at pH 4.0 as described in Example 15 in the range between 70° C. and 95° C., such as between 80° C. and 90° C.

In an embodiment the glucoamylase, such as a *Penicillium oxalicum* glucoamylase variant, used in liquefaction has a thermostability determined as DSC Td at pH 4.8 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C., such as at least 91° C. In an embodiment the glucoamylase, such as a *Penicillium oxalicum* glucoamylase variant has a thermostability determined as DSC Td at pH 4.8 as described in Example 15 in the range between 70° C. and 95° C., such as between 80° C. and 90° C.

In an embodiment the glucoamylase, such as a *Penicillium oxalicum* glucoamylase variant, used in liquefaction has a residual activity determined as described in Example 16 of at least 100% such as at least 105%, such as at least 110%, such as at least 115%, such as at least 120%, such as at least 125%. In an embodiment the glucoamylase, such as a *Penicillium oxalicum* glucoamylase variant has a thermostability determined as residual activity as described in Example 16 in the range between 100% and 130%.

Further, according to the process of the invention also a pullulanase may be present during liquefaction in combination with an alpha-amylase, a protease and/or a glucoamylase.

According to the process of the invention a glucoamylase may be present and/or added in saccharification and/or fermentation or simultaneous saccharification and fermentation. The glucoamylase may not be the same as the thermostable glucoamylase used in liquefaction.

In an embodiment the glucoamylase present and/or added in saccharification and/or fermentation is of fungal origin, such as of filamentous fungus origin. In a preferred embodiment the glucoamylase is derived from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*, such as *G. serpiarium* or *G. trabeum*, or a strain of the *Nigrofomes*.

In an embodiment the glucoamylase is derived from *Talaromyces emersonii*, such as the one shown in SEQ ID NO: 19 herein. In another embodiment the glucoamylase present and/or added in saccharification and/or fermentation is derived from *Gloeophyllum serpiarium*, such as the one shown in SEQ ID NO: 15 herein. In another embodiment the glucoamylase present and/or added in saccharification and/or fermentation is derived from *Gloeophyllum trabeum* such as the one shown in SEQ ID NO: 17 herein.

In an embodiment the glucoamylase is a variant of the *Gloeophyllum trabeum* glucoamylase disclosed in WO2014/177546 (hereby incorporated by reference), especially a variant having one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 17 herein for numbering).

In a preferred embodiment the glucoamylase is present and/or added in saccharification and/or fermentation in combination with an alpha-amylase and optionally a protease. The alpha-amylase may be of fungal or bacterial origin.

The alpha-amylase present and/or added in saccharification and/or fermentation in combination with a glucoamylase may be derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 16 herein.

In a preferred embodiment the alpha-amylase is derived from a strain of *Rhizomucor pusillus*, preferably with an *Aspergillus niger* glucoamylase linker and starch-binding domain (SBD), preferably the one disclosed as SEQ ID NO: 16 herein, preferably having one or more of the following substitutions: G128D, D143N, preferably G128D+D143N (using SEQ ID NO: 16 for numering).

In an embodiment a protease is present and/or added in saccharification and/or fermentation, or SSF. This results in increased ethanol yield. As described, e.g., in U.S. Pat. No. 5,231,017 (hereby incorporated by reference) the protease may, e.g., be an acid fungal protease. A protease may also be present and/or added in saccharification and/or fermentation or SSF, in accordance with a process of the invention, to improve the oil yield. As can be seen in Example 40 the oil yield is increased when adding a protease, e.g., Protease X used in Example 40. Other proteases may also be used. In an embodiment the protease is a metallo protease, such as one derived from a strain of the genus *Thermoascus*, such as a strain of *Thermoascus aurantiacus*. When using a yeast strain of the invention the oil yield is increased even more compared to a corresponding process using Ethanol Red™. This is described in Example 40. Commercially available protease products include Olexa™ from Novozymes A/S, Denmark.

In an embodiment the invention relates processes for producing ethanol from starch-containing material comprising the steps of:

i) liquefying the starch-containing material at a temperature above the initial gelatinization temperature using an alpha-amylase derived from *Bacillus stearothermophilus*;

ii) saccharifying using a glucoamylase;

iii) fermenting using a fermenting organism;

wherein the fermenting organism has one or more, such as all, of the following properties:

increases ethanol yield compared to Ethanol Red™ under the same process conditions;

produces reduced levels of lactic acid compared to Ethanol Red™ under the same process conditions;

produces reduced levels of glycerol compared to Ethanol Red™ under the same process conditions reduces the level of acetaldehyde in fermentation compared to Ethanol Red™ under the same process condition;

increases the oil yield compared to Ethanol Red™ under the same process conditions;

has faster fermentation kinetics compared to Ethanol Red™ under the same process conditions.

In an embodiment the fermenting organism is *Saccharomyces cerevisiae* MBG4851 (deposited under Accession No. V14/004037 at National Measurement Institute, Victoria, Australia).

In an embodiment the fermenting organism is a strain having properties that are about the same as that of *Saccharomyces cerevisiae* MBG4851 or a derivative of *Saccharomyces* strain V14/004037 having defining characteristics of strain V14/004037.

In an embodiment of the invention a cellulolytic composition is present and/or added in saccharification, fermentation or simultaneous saccharification and fermentation (SSF). Examples of such compositions can be found in the "Cellulolytic Composition present and/or added during Saccharification and/or Fermentation"-section below. In a preferred embodiment the cellulolytic composition is present and/or added together with a glucoamylase, such as one disclosed in the "Glucoamylase Present And/Or Added in Saccharification and/or Fermentation"-section below.

A second aspect provides a *Saccharomyces* yeast strain deposited under the Budapest Treaty and having NMI accession no. V14/004037 (*Saccharomyces cerevisiae* MBG4851) or a strain having properties that are about the same as that of *Saccharomyces cerevisiae* MBG4851, or a derivative of *Saccharomyces* strain V14/004037 having defining characteristics of strain V14/004037.

A third aspect provides a method of producing a *Saccharomyces* strain having defining characteristics of strain V14/004037, comprising:
(a) providing: (i) a first yeast strain; and (ii) a second yeast strain, wherein the second yeast strain is strain V14/004037 or a derivative of strain V14/004037;
(b) culturing the first yeast strain and the second yeast strain under conditions which permit combining of DNA between the first yeast strain and the second yeast strain;
(c) screening or selecting for a derivative of strain V14/004037;
(d) optionally repeating steps (b) and (c) with the screened or selected strain from step (c) as the first and/or second strain, until a derivative is obtained which exhibits the defining characteristics of strain V14/004037.

A fourth aspect provides a *Saccharomyces* strain produced by the method of the third aspect.

A fifth aspect provides a method of producing ethanol, comprising incubating a strain of the second or forth aspect with a substrate comprising a fermentable sugar under conditions which promote fermentation of the fermentable sugar to produce ethanol.

A sixth aspect provides use of a strain of the second or fourth aspect in the production of ethanol.

A seventh aspect provides a method of producing distiller's grain, comprising:
(a) incubating a *Saccharomyces* strain of the second or fourth aspect with a substrate comprising fermentable sugar under conditions which allow fermentation of the fermentable sugar to produce ethanol and distiller's grains;
(b) isolating the distiller's grains.

An eighth aspect provides distiller's grain produced by the method of the seventh aspect.

Ah ninth aspect provides use of a strain of the second or fourth aspect in the production of distiller's grains.

A tenth aspect provides use of a strain of the second or fourth aspect in the production of a *Saccharomyces* strain which exhibits one or more defining characteristics of strain V14/004037.

An eleventh aspect provides a composition comprising a *Saccharomyces* strain of the second or fourth aspect.

A twelfth aspect provides processes of using a *Saccharomyces* strain of the second or fourth aspect in a process of the first aspect.

In a thirteenth aspect the invention relates to the use of strain V14/004037 (*Saccharomyces cerevisiae* MBG4851) or a derivative of strain V14/004037 for reducing the level of acetaldehyde in fermentation compared to Ethanol Red™ under the same process condition.

Finally the invention also relates to compositions comprising a *Saccharomyces* yeast strain of the invention, e.g., MBG4851 or a derivative thereof, and naturally occurring and/or non-naturally occurring components.

DETAILED DESCRIPTION OF THE INVENTION

Processes of the Invention

Figure 1:
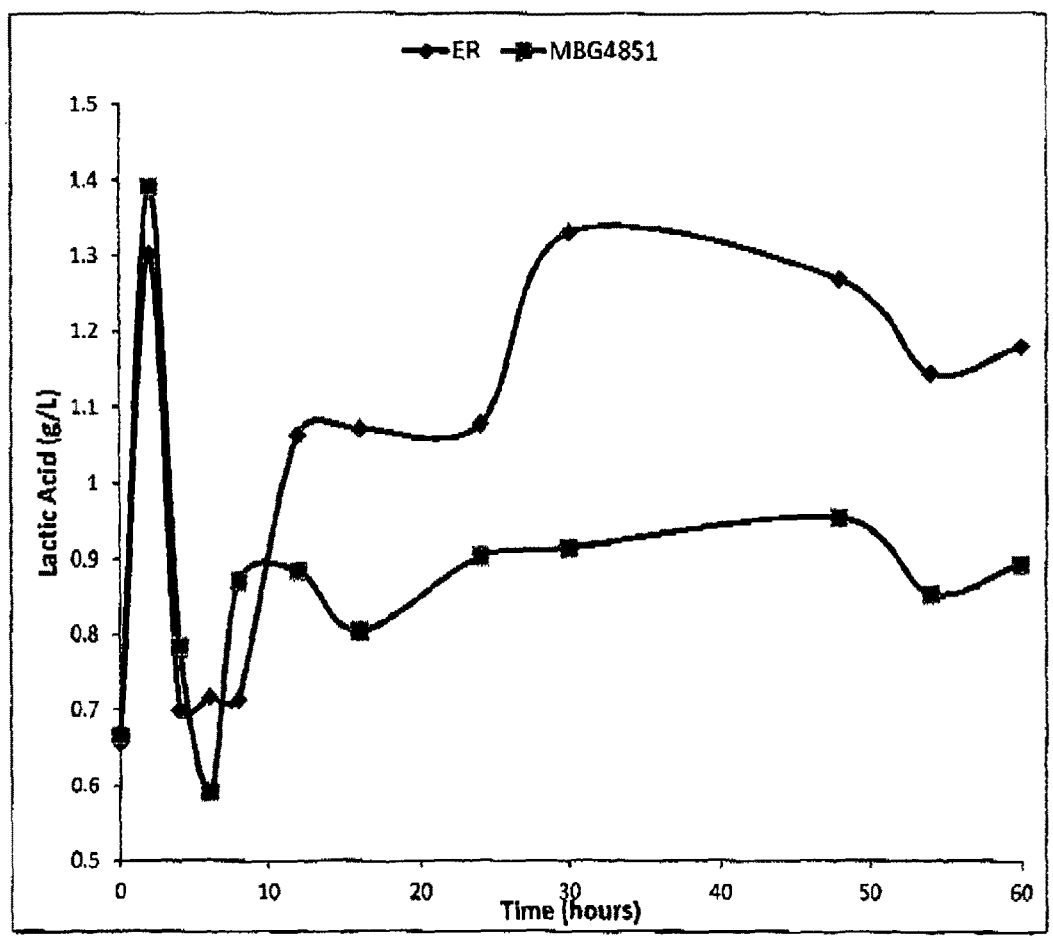
FIG. 1 shows lactic acid titers levels during 1 L corn mash fermentations, liquefied with Alpha-Amylase A.

In this aspect the present invention relates to producing ethanol from starch-containing material in a process including liquefaction, saccharification and fermentation. Fermentable sugars generated during saccharification are converted to ethanol during fermentation by yeast.

In the first aspect the invention relates to processes for producing ethanol from starch-containing material comprising the steps of:
i) liquefying the starch-containing material at a temperature above the initial gelatinization temperature using an alpha-amylase;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae*

MBG4851 or a derivative of *Saccharomyces* strain V14/004037 having defining characteristics of strain V14/004037

Steps ii) and iii) are carried out either sequentially or simultaneously (SSF). In a preferred embodiment steps ii) and iii) are carried out simultaneously (SSF).

Nitrogens-Source Added During Fermentation

Generally fermenting organisms such as yeast, including *Saccharomyces cerevisiae* yeast, require an adequate source of nitrogen for propagation and fermentation. Many sources of nitrogen can be used and such sources of nitrogen are well known in the art. According to the invention the nitrogen source may be organic, such as urea, DDGs, wet cake or corn mash, or inorganic, such as ammonia or ammonium hydroxide. In a preferred embodiment the nitrogen source is urea.

In an embodiment of the invention, less than 3,000 ppm, such as less than 2,000 ppm, such as less than 1,000 ppm, such as less than 800 ppm, such as less than 600 ppm, such as less than 500 ppm, such as less than 400 ppm, such as less than 300 ppm, such as less than 200 ppm, such as less than 100 ppm nitrogen source, especially urea, may be added in saccharification and/or fermentation or SSF.

In a preferred embodiment from 100 to 600 ppm nitrogen source, such as urea, may be added in saccharification and/or fermentation or simultaneous saccharification and fermentation (SSF).

In an embodiment of the invention no nitrogen source, such as urea, is added in saccharification and/or fermentation or SSF.

The inventors have surprisingly found that when using the *Saccharomyces* MBG4851 yeast there is a reduced need for adding a supplementing nitrogen source, such as urea, in fermentation or SSF compared to using the industry standard yeast Ethanol Red™ (ER). For instance, when the MBG4851 yeast was used in mash liquefied with the addition of 3 μg PfuS/g DS, no added urea is required to ferment to dryness. In addition, the MBG4851 yeast provided at least a 1% increase in ethanol yield over Ethanol Red™ yeast. This is described in the Examples below.

Reduced Lactic Acid Generated

The inventors also found that when using the *Saccharomyces* MBG4851 yeast in liquefied mash an approximately 15-20% reduction in lactic acid accumulation during fermentation was obtained. This would help reduce a number of problems that ethanol plants experience and would increase the ethanol yield. The working examples below show that fermentations of different alpha-amylase liquefied mashes give lower lactic acid at fermentation finish when using MBG4851 yeast compared to fermentations using the industry standard yeast Ethanol Red™ (ER).

Reduced Glycerol

The inventors have also surprisingly found that fermentation with MBG4851 yeast resulted in reduced glycerol levels compared to Ethanol Red™ (ER). For instance, the glycerol level was reduced by at least 10% when comparing MBG4851 to Ethanol Red™ (ER) after 54 hours fermentation of corn mash liquefied with alpha-amylase when between 0 to 3,000 ppm urea were present in fermentation (See Example 31). Generally the working examples below show that fermentations of mashes prepared with different alpha-amylases give lower glycerol levels at fermentation finish when using MBG4851 yeast compared to fermentations using the industry standard yeast Ethanol Red™ (ER).

Reduced Acetaldehyde Level

The inventors have surprisingly found that fermentation with MBG4851 yeast results in a reduced acetaldehyde level in fermentation compared to when fermenting with Ethanol Red™ (ER) at the same conditions. This enables reduction of added chemicals needed to mitigate high acetaldehyde levels. Example 39 below shows that reduced acetaldehyde accumulation is found in mash liquefied using alpha-amylase, glucoamylase and protease when using MBG4851 compared to Ethanol Red™ (ER). Specifically, Example 39 shows a 52% reduction in the acetaldehyde level when using MBG4851 compared to Ethanol Red™ (ER).

Increased Oil Yield

The inventors have surprisingly found that fermentation with MBG4851 yeast results in increased oil yield when compared to Ethanol Red™ (ER). When additionally a protease, such as a metallo protease derived from a strain of the genus *Thermoascus*, is added to fermentation the yield increases even more. Therefore, in an embodiment of the invention a protease is added in saccharification and/or fermentation or SSF. Example 40 shows that the oil yield during corn mash fermentation was increased by almost 20%. When a protease was added more than 45% increase was observed compared to fermentation using Ethanol Red™, i.e., no protease. If a protease was already present approximately 20% more oil could be obtained.

Liquefaction Step i)

According to processes of the invention liquefaction in step i) may be carried out by subjecting starch-containing material at a temperature above the initial gelatinization temperature to an alpha-amylase and optionally a protease, and/or a glucoamylase. Other enzymes such as a pullulanase and phytase may also be present and/or added in liquefaction.

Liquefaction step i) may be carried out for 0.5-5 hours, such as 1-3 hours, such as typically around 2 hours.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466.

According to the invention liquefaction is typically carried out at a temperature in the range from 70-100° C. In an embodiment the temperature in liquefaction is between 75-95° C., such as between 75-90° C., preferably between 80-90° C., such as 82-88° C., such as around 85° C.

According to the invention a jet-cooking step may be carried out prior to liquefaction in step i). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

The pH during liquefaction may be between 4-7, such as between pH 4.5-6.5, such as between pH 5.0-6.5, such as between pH 5.0-6.0, such as between pH 5.2-6.2, such as around 5.2, such as around 5.4, such as around 5.6, such as around 5.8.

In an embodiment, the process of the invention further comprises, prior to the step i), the steps of:

a) reducing the particle size of the starch-containing material, preferably by dry milling;

b) forming a slurry comprising the starch-containing material and water.

The starch-containing starting material, such as whole grains, may be reduced in particle size, e.g., by milling, in order to open up the structure, to increase surface area, and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. According to the present invention dry milling is preferred.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material.

The alpha-amylase, optionally a protease, optionally a glucoamylase may initially be added to the aqueous slurry to initiate liquefaction (thinning). In an embodiment only a portion of the enzymes (e.g., about ⅓) is added to the aqueous slurry, while the rest of the enzymes (e.g., about ⅔) are added during liquefaction step i).

A non-exhaustive list of examples of alpha-amylases can be found below in the "Alpha-Amylase Present and/or Added During Liquefaction"-section. In an embodiment the alpha-amylase is a bacterial alpha-amylase. Bacterial alpha-amylases are typically thermostable. In a preferred embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

In an embodiment the alpha-amylase has an improved stability compared to a reference alpha-amylase (*Bacillus stearothermophilus* alpha-amylase with the mutations I181*+G182*, optionally with a N193F substitution, truncated to around 491 amino acids, i.e., from 480-495 amino acids, (using SEQ ID NO: 1 herein for numbering) determined by incubating the reference alpha-amylase and variants at pH 4.5 and 5.5 and temperatures of 75° C. and 85° C. with 0.12 mM CaCl₂ followed by residual activity determination using the EnzChek® substrate (EnzChek® Ultra Amylase assay kit, E33651, Molecular Probes). This is described in Example 1.

Examples of suitable *Bacillus stearothermophilus* alpha-amylase variants can be found below in the "Thermostable Alpha-Amylase"-section and include one from the following group of *Bacillus stearothermophilus* alpha-amylase variants with the following mutations:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V;
I181*+G182*+N193F+V59A+E129V+K177L+R179E+Q254S+M284V; and
I181*+G182*+N193F+E129V+K177L+R179E+K220P+N224L+S242Q+Q254S (using SEQ ID NO: 1 for numbering).

Examples of other suitable *Bacillus stearothermophilus* alpha-amylases having increased thermostability compared to a reference alpha-amylase (*Bacillus stearothermophilus* alpha-amylase with the mutations I181*+G182*+N193F truncated to 491 amino acids) at pH 4.5 and 5.5, 0.12 mM CaCl₂ can be found in WO 2011/082425 hereby incorporated by reference. (See also Example 1 below)

According to processes of the invention, liquefaction in step i) may be carried out using a combination of alpha-amylase and protease. The protease may be a protease having a thermostability value of more than 20% determined as Relative Activity at 80° C./70° C. determined as described in Example 1 (Relative Activity). Examples of suitable proteases are described below in the section "Protease Present and/or Added During Liquefaction".

The protease may be of fungal origin, such as of filamentous fungus origin. Specific examples of suitable fungal proteases are protease variants of metallo protease derived from a strain of the genus *Thermoascus*, preferably a strain of *Thermoascus aurantiacus*, especially the strain *Thermoascus aurantiacus* CGMCC No. 0670 disclosed as the mature part of SEQ ID NO. 2 disclosed in WO 2003/048353 or the mature part of SEQ ID NO: 1 in WO 2010/008841 or SEQ ID NO: 3 herein with the following mutations:

D79L+S87P+A112P+D142L:
D79L+S87P+D142L; or
A27K+D79L+Y82F+S87G+D104P+A112P+A126V+D142L.

More examples of suitable variants of the *Thermoascus aurantiacus* protease can be found in WO 2011/072191 hereby incorporated by reference (See also Example 2 below).

Suitable proteases also include bacterial proteases. A suitable bacterial protease may be derived from a strain of *Pyrococcus*, preferably a strain of *Pyrococcus furiosus*. In a preferred embodiment the protease is the one shown in SEQ ID NO: 1 in U.S. Pat. No. 6,358,726 or SEQ ID NO: 13 herein.

In an embodiment of the invention the alpha-amylase and/or protease, added in the liquefaction step i), is/are further combined with a glucoamylase. Thus, a glucoamylase may also be present and/or added during liquefaction step i). The glucoamylase is preferably thermostable. This means that the glucoamylase has a heat stability at 85° C., pH 5.3, of at least 20%, such as at least 30%, preferably at least 35% determined as described in Example 4 (heat stability). In an embodiment the glucoamylase present and/or added in liquefaction has a relative activity pH optimum at pH 5.0 of at least 90%, preferably at least 95%, preferably at least 97%. In an embodiment the glucoamylase has a pH stability at pH 5.0 of at least at least 80%, at least 85%, at least 90% determined as described in Example 4 (pH stability).

A suitable glucoamylase present and/or added in liquefaction step i) may according to the invention be derived from a strain of the genus *Penicillium*, especially a strain of *Penicillium oxalicum* disclosed as SEQ ID NO: 2 in WO 2011/127802 or SEQ ID NOs: 9 or 14 herein. In a preferred embodiment the glucoamylase is a variant of the *Penicillium oxalicum* glucoamylase shown in SEQ ID NO: 2 in WO 2011/127802 having a K79V substitution (using the mature sequence shown in SEQ ID NO: 14 herein for numbering), such as a variant disclosed in WO 2013/053801. In a preferred embodiment the *Penicillium oxalicum* glucoamylase has a K79V substitution (using SEQ ID NO: 14 for numbering) and further one of the following:

P11F+T65A+Q327F;

P2N+P4S+P11F+T65A+Q327F (using SEQ ID NO: 14 for numbering).

Examples of other suitable *Penicillium oxalicum* glucoamylase variants can be found in WO 2013/053801 incorporated by reference (see also Examples 10-16 below, such as the *Penicillium oxalicum* glucoamylase variants in Table 15).

Further, according to the process of the invention also a pullulanase may be present during liquefaction in combination with an alpha-amylase, a protease and/or a glucoamylase.

Saccharification and Fermentation

A glucoamylase is present and/or added in saccharification step ii) and/or fermentation step iii) or simultaneous saccharification and fermentation (SSF). The glucoamylase added in saccharification step ii) and/or fermentation step iii) or simultaneous saccharification and fermentation (SSF) is typically different from the glucoamylase, optionally added in liquefaction step i). In a preferred embodiment the glucoamylase is added together with a fungal alpha-amylase. Examples of glucoamylases can be found in the "Glucoamylases Present and/or Added In Saccharification and/or Fermentation"-section below.

When doing sequential saccharification and fermentation, saccharification step ii) may be carried out at conditions well-known in the art. For instance, the saccharification step ii) may last up to from about 24 to about 72 hours. In an embodiment pre-saccharification is done. Pre-saccharification is typically done for 40-90 minutes at a temperature between 30-65° C., typically about 60° C. Pre-saccharification is in an embodiment followed by saccharification during fermentation in simultaneous saccharification and fermentation (SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. However, it is also contemplated to add the fermenting organism and enzyme(s) separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 4-5.

In an embodiment of the invention a cellulolytic composition is present and/or added in saccharification, fermentation or simultaneous saccharification and fermentation (SSF). Examples of such cellulolytic compositions can be found in the "Cellulolytic Composition present and/or added during Saccharification and/or Fermentation"-section below. The cellulolytic composition is present and/or added together with a glucoamylase, such as one disclosed in the "Glucoamylase Present And/Or Added in Saccharification and/or Fermentation"-section below.

Starch-Containing Materials

According to the invention any suitable starch-containing starting material may be used. The starting material is generally selected based on the desired fermentation product, here ethanol. Examples of starch-containing starting materials, suitable for use in processes of the present invention, include cereal, tubers or grains. Specifically the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

In a preferred embodiment the starch-containing starting material is oats.

Fermentation

Fermentation is carried out in a fermentation medium. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

*Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851 or defining characteristics of *Saccharomyces cerevisiae* MBG4851 is used in a process of the invention.

In an embodiment the fermenting organism strain has properties that are about the same as that of *Saccharomyces cerevisiae* MBG4851 as it provides an increase in ethanol yield compared to Ethanol Red™ (ER) under the same process conditions.

In an embodiment the fermenting organism strain has properties that are about the same as that of *Saccharomyces cerevisiae* MBG4851 as it provides an increase in ethanol yield compared to Ethanol Red™ (ER) under the same conditions where no urea is present and/or added in simultaneous saccharification and fermentation (SSF).

In an embodiment the fermenting organism strain having properties that are about the same as that of *Saccharomyces*

*cerevisiae* MBG4851, as it produces reduced levels of lactic acid compared to Ethanol Red™ under the same process conditions.

In an embodiment the fermenting organism strain having properties that are about the same as that of *Saccharomyces cerevisiae* MBG4851, as it produces reduced levels of glycerol compared to Ethanol Red™ under the same process conditions.

In an embodiment the fermenting organism strain having properties that are about the same as that of *Saccharomyces cerevisiae* MBG4851, reduces the level of acetaldehyde in fermentation compared to Ethanol Red™ under the same process condition.

In an embodiment the fermenting organism strain having properties that are about the same as that of *Saccharomyces cerevisiae* MBG4851, increases the oil yield compared to Ethanol Red™ under the same process conditions.

In an embodiment the fermenting organism strain having properties that are about the same as that of *Saccharomyces cerevisiae* MBG4851, as it has faster fermentation kinetics compared to Ethanol Red™ under the same process conditions.

In an embodiment the fermenting organism strain having properties that are about the same as that of *Saccharomyces cerevisiae* MBG4851 has one or more, such as all, of the following properties and defining characteristics:
  increases ethanol yield compared to Ethanol Red™ under the same process conditions;
  produces reduced levels of lactic acid compared to Ethanol Red™ under the same process conditions;
  produces reduced levels of glycerol compared to Ethanol Red™ under the same process conditions;
  reduces the level of acetaldehyde in fermentation compared to Ethanol Red™ under the same process condition;
  increases the oil yield compared to Ethanol Red™ under the same process conditions;
  has faster fermentation kinetics compared to Ethanol Red™ under the same process conditions.

In an embodiment of the invention the fermenting organism strain having properties that are about the same as that of *Saccharomyces cerevisiae* MBG4851 provides an ethanol yield boost over Ethanol Red™ (ER) of more than 1.0% at 0 ppm urea and at a Protease Pfu dose of 3 µg EP/gDS (added in liquefaction), such as more than 1.5% at 0 ppm urea and at a Pfu dose of 1.5 µg EP/gDS, such as more than 4.0% at 0 ppm urea and at a Protease Pfu dose of 0.0385 µg EP/gDS when determined using the process set-up and conditions used in Example 19.

In an embodiment of the invention the fermenting organism strain having properties that are about the same as that of *Saccharomyces cerevisiae* MBG4851 provides an ethanol yield boost of more than 1.0% at urea levels of 300 ppm, such as more than 3.0% at urea levels of 150 ppm, such as more than 10.0% at urea levels of 0 ppm over Ethanol Red™ when determined using the process set-up and conditions used in Example 21.

In an embodiment of the invention the fermenting organism strain having properties that are about the same as that of *Saccharomyces cerevisiae* MBG4851 provides a reduction in lactic acid in a 54 hours fermentation of more than 50% at urea levels of 0 ppm and at a Protease Pfu dose of 0.0385 µg/g DS (added in liquefaction), such as more than 50% at urea levels of 0 ppm and a Protease Pfu dose of 3 µg/gDS over Ethanol Red when determined using the process set-up and conditions used in Example 23.

In an embodiment of the invention the fermenting organism strain having properties that are about the same as that of *Saccharomyces cerevisiae* MBG4851 provides a reduction in glycerol levels in a 60 hours fermentation of more than 2.0% such as more than 3.0%, such as more than 4.0% over Ethanol Red™ (ER) when determined using the process set-up and conditions used in Example 34.

In an embodiment of the invention the fermenting organism strain having properties that are about the same as that of *Saccharomyces cerevisiae* MBG4851 provides a reduction in the acetaldehyde level, in a 54 hours fermentation, of more than 30%, such as more than 40%, such as more than 50% over Ethanol Red™ (ER) when determined using the process set-up and conditions used in Example 39.

In an embodiment of the invention the fermenting organism strain having properties that are about the same as that of *Saccharomyces cerevisiae* MBG4851 or defining characteristics thereof provides an increase in oil yield, after 64 hours fermentation, of more than 10%, such as more than 12%, such as more than 14%, such as more than 16%, such as more than 18%, such as more than 20%, such as between 10-20%, such as between 10-15%, such as between 15-20% over Ethanol Red™ (ER) when determined using the process set-up and conditions used in Example 40.

Recovery

Subsequent to fermentation, e.g., SSF, the ethanol may be separated from the fermentation medium. The slurry may be distilled to recover/extract the desired fermentation product (i.e., ethanol). Alternatively the desired fermentation product (i.e., ethanol) may be extracted from the fermentation medium by micro or membrane filtration techniques. The fermentation product (i.e., ethanol) may also be recovered by stripping or other method well known in the art.

In an embodiment the invention relates to processes of recovering/extracting oil from an ethanol production process of the invention comprising the steps of:
  i) liquefying starch-containing material at a temperature above the initial gelatinization temperature using an alpha-amylase;
  ii) saccharifying using a glucoamylase;
  iii fermenting using a fermenting organism.
  iv) recovering the fermentation product to form whole stillage;
  v) separating the whole stillage into thin stillage and wet cake;
  vi) optionally concentrating the thin stillage into syrup;
wherein oil is recovered/extracted downstream from fermentation step iii) and wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851 or a derivative of *Saccharomyces* strain V14/004037 having defining characteristics of strain V14/004037.

In a preferred embodiment the oil is recovered/extracted from the thin stillage. In a preferred embodiment the oil is recovered/extracted from the syrup/evaporated centrate.

In an embodiment protease is added in saccharification and/or fermentation or SSF.

In an embodiment the invention concerns processes of recovering/extracting oil from an ethanol production process comprising the steps of:
i) liquefying starch-containing material at a temperature above the initial gelatinization temperature using:
  *Bacillus stearothermophilus* alpha-amylase;
  optionally a *Pyrococcus furiosus* protease;

optionally *Penicillium oxalicum* glucoamylase;
ii) saccharifying using a glucoamylase;
iii) fermenting using a fermenting organism.
iv) recovering the fermentation product to form whole stillage;
v) separating the whole stillage into thin stillage and wet cake;
vi) optionally concentrating the thin stillage into syrup;
wherein oil is recovered/extracted downstream from fermentation step iii) and wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851 or a derivative of *Saccharomyces* strain V14/004037 having defining characteristics of strain V14/004037.

In an embodiment a protease is added in saccharification and/or fermentation or SSF.

Alpha-Amylase Present and/or Added in Liquefaction

According to the invention an alpha-amylase is present and/or added in liquefaction optionally together with a protease and/or glucoamylase, and/or optional pullulanase.

The alpha-amylase added in liquefaction step i) may be any alpha-amylase. Preferred are bacterial alpha-amylases, which typically are stable at temperature, used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 or SEQ ID NO: 21 herein (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 1 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids, e.g., so it lacks a functional starch binding domain (compared to SEQ ID NO: 3 in WO 99/19467) or SEQ ID NO: 1 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 1 herein. The bacterial alpha-amylase may also have a substitution in a position corresponding to S239 in the *Bacillus licheniformis* alpha-amylase shown in SEQ ID NO: 4 in WO 99/19467 or SEQ ID NO: 21 herein, or a S242 and/or E188P variant of the *Bacillus stearothermophilus* alpha-amylase of SEQ ID NO: 3 in WO 99/19467 or SEQ ID NO: 1 herein.

In an embodiment the variant is a S242A, E or Q variant, preferably a S242Q variant, of the *Bacillus stearothermophilus* alpha-amylase (using SEQ ID NO: 1 herein for numbering).

In an embodiment the variant is a position E188 variant, preferably E188P variant of the *Bacillus stearothermophilus* alpha-amylase (using SEQ ID NO: 1 herein for numbering).

The bacterial alpha-amylase may in an embodiment be a truncated *Bacillus* alpha-amylase. Especially the truncation is so that, e.g., the *Bacillus stearothermophilus* alpha-amylase shown in SEQ ID NO: 3 in WO 99/19467 or SEQ ID NO: 1 herein, is around 491 amino acids long, such as from 480 to 495 amino acids long, or so it lack a functional starch bind domain.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:
G48A+T49I+G107A+H156Y+A181T+N190F+I201F+
A209V+Q264S (using the *Bacillus licheniformis* numbering in SEQ ID NO: 4 of WO 99/19467) or SEQ ID NO: 21 herein. Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase may be a thermostable alpha-amylase, such as a thermostable bacterial alpha-amylase, preferably from *Bacillus stearothermophilus*. In an embodiment the alpha-amylase used according to the invention has a T½ (min) at pH 4.5, 85° C., 0.12 mM CaCl$_2$ of at least 10 determined as described in Example 1.

In an embodiment the thermostable alpha-amylase has a T½ (min) at pH 4.5, 85° C., 0.12 mM CaCl$_2$, of at least 15.

In an embodiment the thermostable alpha-amylase has a T½ (min) at pH 4.5, 85° C., 0.12 mM CaCl$_2$, of as at least 20.

In an embodiment the thermostable alpha-amylase has a T½ (min) at pH 4.5, 85° C., 0.12 mM CaCl$_2$, of as at least 25.

In an embodiment the thermostable alpha-amylase has a T½ (min) at pH 4.5, 85° C., 0.12 mM CaCl$_2$, of as at least 30.

In an embodiment the thermostable alpha-amylase has a T½ (min) at pH 4.5, 85° C., 0.12 mM CaCl$_2$, of as at least 40.

In an embodiment the thermostable alpha-amylase has a T½ (min) at pH 4.5, 85° C., 0.12 mM CaCl$_2$, of at least 50.

In an embodiment the thermostable alpha-amylase has a T½ (min) at pH 4.5, 85° C., 0.12 mM CaCl$_2$, of at least 60.

In an embodiment the thermostable alpha-amylase has a T½ (min) at pH 4.5, 85° C., 0.12 mM CaCl$_2$, between 10-70.

In an embodiment the thermostable alpha-amylase has a T½ (min) at pH 4.5, 85° C., 0.12 mM CaCl$_2$, between 15-70.

In an embodiment the thermostable alpha-amylase has a T½ (min) at pH 4.5, 85° C., 0.12 mM CaCl$_2$, between 20-70.

In an embodiment the thermostable alpha-amylase has a T½ (min) at pH 4.5, 85° C., 0.12 mM CaCl$_2$, between 25-70.

In an embodiment the thermostable alpha-amylase has a T½ (min) at pH 4.5, 85° C., 0.12 mM CaCl$_2$, between 30-70.

In an embodiment the thermostable alpha-amylase has a T½ (min) at pH 4.5, 85° C., 0.12 mM CaCl$_2$, between 40-70.

In an embodiment the thermostable alpha-amylase has a T½ (min) at pH 4.5, 85° C., 0.12 mM CaCl$_2$, between 50-70.

In an embodiment the thermostable alpha-amylase has a T½ (min) at pH 4.5, 85° C., 0.12 mM CaCl$_2$, between 60-70.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 1 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optional substitution N193F, further comprising mutations selected from below list:

V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+1270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91 L+M961+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+5242Q+Q254S+N376*+1377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A+Q89R+E129V+K177L+R179E+Q254S+M284V.
V59A+E129V+K177L+R179E+Q254S+M284V;

In a preferred embodiment the alpha-amylase is selected from the group of *Bacillus stearothermophilus* alpha-amylase variants:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V;
I181*+G182*+N193F+V59A+E129V+K177L+R179E+Q254S+M284V; and
I181*+G182*+N193F+E129V+K177L+R179E+K220P+N224L+S242Q+Q254S (using SEQ ID NO: 1 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 1 herein, or variants thereof, are truncated in the C-terminal and are typically around 491 amino acids long, such as from 480-495 amino acids long, or so that it lacks a functional starch binding domain.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 1 herein.

In an embodiment the bacterial alpha-amylase, e.g., Bacillus alpha-amylase, such as especially Bacillus stearothermophilus alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-a/g DS. In an embodiment the bacterial alpha-amylase, e.g., Bacillus alpha-amylase, such as especially Bacillus stearothermophilus alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

Protease Present and/or Added In Liquefaction

According to the invention a protease is optionally present and/or added in liquefaction together with the alpha-amylase, and an optional glucoamylase, and/or pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process of the invention as long as it fulfills the thermostability properties defined below.

In one embodiment the protease is of fungal origin.

The protease may be a variant of, e.g., a wild-type protease as long as the protease has the thermostability properties defined herein. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus Thermoascus, preferably a strain of Thermoascus aurantiacus, especially Thermoascus aurantiacus CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 3 herein further with mutations selected from below list:
S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein with the following mutations:
D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), or SEQ ID NO: 13 herein.

In another embodiment the thermostable protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Bio, Japan.

The *Pyrococcus furiosus* protease is a thermostable protease according to the invention. The commercial product *Pyrococcus furiosus* protease (Pfu S) was found to have a thermostability of 110% (80° C./70° C.) and 103% (90° C./70° C.) at pH 4.5 determined as described in Example 2.

In one embodiment a thermostable protease used in a process of the invention has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C. In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2.

In an embodiment the protease may have a thermostability for above 90, such as above 100 at 85° C. as determined using the Zein-BCA assay as disclosed in Example 3.

In an embodiment the protease has a themostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay.

Glucoamylase Present and/or Added in Liquefaction Step i)

According to the invention a glucoamylase may optionally be present and/or added in liquefaction step i). In a preferred embodiment the glucoamylase is added together with or separately from the alpha-amylase and/or the protease and/or pullulanase.

In an embodiment the glucoamylase has a Relative Activity heat stability at 85° C. of at least 20%, at least 30%, preferably at least 35% determined as described in Example 4 (heat stability).

In an embodiment the glucoamylase has a relative activity pH optimum at pH 5.0 of at least 90%, preferably at least 95%, preferably at least 97%, such as 100% determined as described in Example 4 (pH optimum).

In an embodiment the glucoamylase has a pH stability at pH 5.0 of at least at least 80%, at least 85%, at least 90% determined as described in Example 4 (pH stability).

In an embodiment the glucoamylase, such as a *Penicillium oxalicum* glucoamylase variant, used in liquefaction has a thermostability determined as DSC Td at pH 4.0 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C. In an embodiment the glucoamylase, such as a *Penicillium oxalicum* glucoamylase variant has a thermostability determined as DSC Td at pH 4.0 as described in Example 15 in the range between 70° C. and 95° C., such as between 80° C. and 90° C.

In an embodiment the glucoamylase, such as a *Penicillium oxalicum* glucoamylase variant, used in liquefaction has a thermostability determined as DSC Td at pH 4.8 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C., such as at least 91° C. In an embodiment the glucoamylase, such as a *Penicillium oxalicum* glucoamylase variant has a thermostability determined as DSC Td at pH 4.8 as described in Example 15 in the range between 70° C. and 95° C., such as between 80° C. and 90° C.

In an embodiment the glucoamylase, such as a *Penicillium oxalicum* glucoamylase variant, used in liquefaction has a residual activity determined as described in Example 16 of at least 100% such as at least 105%, such as at least 110%, such as at least 115%, such as at least 120%, such as at least 125%. In an embodiment the glucoamylase, such as a *Penicillium oxalicum* glucoamylase variant has a thermostability determined as residual activity as described in Example 16 in the range between 100% and 130%.

In a specific and preferred embodiment the glucoamylase, preferably of fungal origin, preferably a filamentous fungi, is from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 9 or 14 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

In a preferred embodiment the glucoamylase is a variant of the *Penicillium oxalicum* glucoamylase disclosed as SEQ ID NO: 2 in WO 2011/127802 and shown in SEQ ID NO: 9 and 14 herein, having a K79V substitution (using the mature sequence shown in SEQ ID NO: 14 herein for numbering). The K79V glucoamylase variant has reduced sensitivity to protease degradation relative to the parent as disclosed in WO 2013/036526 (which are hereby incorporated by reference).

In an embodiment the glucoamylase is derived from *Penicillium oxalicum*.

In an embodiment the glucoamylase is a variant of the *Penicillium oxalicum* glucoamylase disclosed as SEQ ID NO: 2 in WO 2011/127802 and shown in SEQ ID NO: 9 and 14 herein. In a preferred embodiment the *Penicillium oxalicum* glucoamylase is the one disclosed as SEQ ID NO: 2 in WO 2011/127802 and shown in SEQ ID NO: 9 and 14 herein having Val (V) in position 79 (using SEQ ID NO: 14 herein for numbering).

Contemplated *Penicillium oxalicum* glucoamylase variants are disclosed in WO 2013/053801 which is hereby incorporated by reference.

In an embodiment these variants have reduced sensitivity to protease degradation.

In an embodiment these variant have improved thermostability compared to the parent.

More specifically, in an embodiment the glucoamylase has a K79V substitution (using SEQ ID NO: 14 herein for numbering), corresponding to the PE001 variant, and further comprises at least one of the following substitutions or combination of substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11 D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or

P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+V79A+Q327F+E501V+Y504T; or
P2N+P4S+P11F+T65A+V79G+Q327F+E501V+Y504T; or
P2N+P4S+P11F+T65A+V79I+Q327F+E501V+Y504T; or
P2N+P4S+P11F+T65A+V79L+Q327F+E501V+Y504T; or
P2N+P4S+P11F+T65A+V79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the *Penicillium oxalicum* glucoamylase variant has a K79V substitution (using SEQ ID NO: 14 herein for numbering), corresponding to the PE001 variant, and further comprises one of the following mutations:

P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The glucoamylase may be added in amounts from 0.1-100 micrograms EP/g, such as 0.5-50 micrograms EP/g, such as 1-25 micrograms EP/g, such as 2-12 micrograms EP/g DS.

Pullulanase Present and/or Added in Liquefaction Step i)

Optionally a pullulanase may be present and/or added during liquefaction step i) together with an alpha-amylase, and/or protease and/or glucoamylase. As mentioned above a glucoamylase glucoamylase may also be present and/or added during liquefaction step i).

The pullulanase may be present and/or added in liquefaction step i) and/or saccharification step ii) or simultaneous saccharification and fermentation (SSF).

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO92/02614.

In an embodiment the pullulanase is a family GH57 pullulanase. In an embodiment the pullulanase includes an X47 domain as disclosed in U.S. 61/289,040 published as WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown in SEQ ID NO: 11 truncated at site X4 right after the X47 domain (i.e., amino acids 1-782 in SEQ ID NOS: 11 and 12 herein). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO 2011/087836 (which is hereby incorporated by reference) and disclosed in SEQ ID NO: 12 herein.

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (DuPont-Danisco, USA), and AMANO 8 (Amano, Japan).

Glucoamylase Present and/or Added in Saccharification and/or Fermentation

The glucoamylase present and/or added in saccharification, fermentation or simultaneous saccharification and fermentation (SSF) may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem.

(1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti*, *Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulate* (SEQ ID NO: 20), *Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), such as SEQ ID NO: 18 herein, or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 2 in WO 2011/068803 or SEQ ID NO: 15 herein (i.e. *Gloeophyllum sepiarium* glucoamylase). In a preferred embodiment the glucoamylase is SEQ ID NO: 17 herein (i.e., *Gloeophyllum trabeum* glucoamylase discloses as SEQ ID NO: 3 in WO2014/177546). In an embodiment the glucoamylase is derived from a strain of the genus *Nigrofomes*, in particular a strain of *Nigrofomes* sp. disclosed in WO 2012/064351 (SEQ ID NO: 2) (all references hereby incorporated by reference).

Contemplated are also glucoamylases which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 15, 17, 18 or 19 herein, respectively, preferably SEQ ID NO: 15 herein or SEQ ID NO: 17 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Glucoamylases may in an embodiment be added to the saccharification and/or fermentation in an amount of 1-1,000 µg EP/g DS, preferably 10-500 µg/gDS, especially between 25-250 µg/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 7 and *Trametes cingulata* glucoamylase disclosed as SEQ ID NO: 2 in WO 06/069289 and SEQ ID NO: 20 herein.

In an embodiment the glucoamylase is a blend_comprising *Talaromyces emersonii* glucoamylase disclosed in WO 99/28448, *Trametes cingulata* glucoamylase disclosed as SEQ ID NO: 2 in WO 06/69289 and SEQ ID NO: 20 herein, and *Rhizomucor pusillus* alpha-amylase with *Aspergillus niger* glucoamylase linker and SBD disclosed as V039 in Table 5 in WO 2006/069290 or SEQ ID NO: 16 herein.

In an embodiment the glucoamylase is a blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290 or SEQ ID NO: 16 herein.

In an embodiment the glucoamylase is a blend comprising *Gloeophyllum sepiarium* glucoamylase shown as SEQ ID NO: 2 in WO 2011/068803 and *Rhizomucor pusillus* with an *Aspergillus niger* glucoamylase linker and starch-binding domain (SBD), disclosed SEQ ID NO: 3 in WO 2013/006756 with the following substitutions: G128D+D143N.

In an embodiment the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290 or SEQ ID NO: 16 herein.

In an embodiment the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering or SEQ ID NO: 16 herein).

In a preferred embodiment the glucoamylase blend comprises *Gloeophyllum sepiarium* glucoamylase (e.g., SEQ ID NO: 2 in WO 2011/068803 or SEQ ID NO: 15 herein) and *Rhizomucor pusillus* alpha-amylase.

In a preferred embodiment the glucoamylase blend comprises *Gloeophyllum sepiarium* glucoamylase shown as SEQ ID NO: 2 in WO 2011/068803 or SEQ ID NO: 15 herein and *Rhizomucor pusillus* with an *Aspergillus niger* glucoamylase linker and starch-binding domain (SBD), disclosed SEQ ID NO: 3 in WO 2013/006756 and SEQ ID NO: 16 herein with the following substitutions: G128D+D143N.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE™ and AMG™ E (from Novozymes A/S); OPTIDEX™ 300, GC480, GC417 (from DuPont-Danisco); AMIGASE™ and AMIGASE™ PLUS (from DSM); G-ZYME™ G900, G-ZYME™ and G990 ZR (from DuPont-Danisco).

Cellulolytic Composition Present and/or Added During Saccharification and/or Fermentation According to the invention a cellulolytic composition may be present in saccharification, fermentation or simultaneous saccharification and fermentation (SSF).

The cellulolytic composition comprises a beta-glucosidase, a cellobiohydrolase and an endoglucanase.

Examples of suitable cellulolytic composition can be found in WO 2008/151079 and WO 2013/028928 which are incorporated by reference.

In preferred embodiments the cellulolytic composition is derived from a strain of *Trichoderma, Humicola,* or *Chrysosporium.*

In an embodiment the cellulolytic composition is derived from a strain of *Trichoderma reesei, Humicola insolens* and/or *Chrysosporium lucknowense.*

In an embodiment the cellulolytic composition comprises a beta-glucosidase, preferably one derived from a strain of the genus *Aspergillus,* such as *Aspergillus oryzae,* such as the one disclosed in WO 2002/095014 or the fusion protein having beta-glucosidase activity disclosed in WO 2008/057637, or *Aspergillus fumigatus,* such as one disclosed in WO 2005/047499 or an *Aspergillus fumigatus* beta-glucosidase variant disclosed in WO 2012/044915 (Novozymes), such as one with the following substitutions: F100D, S283G, N456E, F512Y; or a strain of the genus a strain *Penicillium,* such as a strain of the *Penicillium brasilianum* disclosed in WO 2007/019442, or a strain of the genus *Trichoderma,* such as a strain of *Trichoderma reesei.*

In an embodiment the cellulolytic composition comprises a GH61 polypeptide having cellulolytic enhancing activity such as one derived from the genus *Thermoascus,* such as a strain of *Thermoascus aurantiacus,* such as the one described in WO 2005/074656 as SEQ ID NO: 2; or one derived from the genus *Thielavia,* such as a strain of *Thielavia terrestris,* such as the one described in WO 2005/074647 as SEQ ID NO: 7 and SEQ ID NO: 8; or one derived from a strain of *Aspergillus,* such as a strain of *Aspergillus fumigatus,* such as the one described in WO 2010/138754 as SEQ ID NO: 1 and SEQ ID NO: 2; or one derived from a strain derived from *Penicillium,* such as a strain of *Penicillium emersonii,* such as the one disclosed in WO 2011/041397.

In an embodiment the cellulolytic composition comprises a cellobiohydrolase I (CBH I), such as one derived from a strain of the genus *Aspergillus,* such as a strain of *Aspergillus fumigatus,* such as the Cel7a CBHI disclosed in SEQ ID NO: 2 in WO 2011/057140, or a strain of the genus *Trichoderma,* such as a strain of *Trichoderma reesei.*

In an embodiment the cellulolytic composition comprises a cellobiohydrolase II (CBH II, such as one derived from a strain of the genus *Aspergillus,* such as a strain of *Aspergillus fumigatus;* or a strain of the genus *Trichoderma,* such as *Trichoderma reesei,* or a strain of the genus *Thielavia,* such as a strain of *Thielavia terrestris,* such as cellobiohydrolase II CEL6A from *Thielavia terrestris.*

In an embodiment the cellulolytic composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499).

In an embodiment the cellulolytic composition is a *Trichoderma reesei* cellulolytic enzyme composition further comprising *Penicillium emersonii* GH61A polypeptide having cellulolytic enhancing activity disclosed in WO 2011/041397 and *Aspergillus fumigatus* beta-glucosidase (SEQ ID NO: 2 of WO 2005/047499) or a variant thereof with the following substitutions F100D, S283G, N456E, F512Y.

In a preferred embodiment the cellulolytic composition comprising one or more of the following components:
  (i) an *Aspergillus fumigatus* cellobiohydrolase I;
  (ii) an *Aspergillus fumigatus* cellobiohydrolase II;
  (iii) an *Aspergillus fumigatus* beta-glucosidase or variant thereof; and
  (iv) a *Penicillium* sp. GH61 polypeptide having cellulolytic enhancing activity; or homologs thereof.

In an preferred embodiment the cellulolytic composition is derived from *Trichoderma reesei* comprising GH61A polypeptide having cellulolytic enhancing activity derived from a strain of *Penicillium emersonii* (SEQ ID NO: 2 in WO 2011/041397, *Aspergillus fumigatus* beta-glucosidase (SEQ ID NO: 2 in WO 2005/047499) variant with the following substitutions: F100D, S283G, N456E, F512Y) disclosed in WO 2012/044915; *Aspergillus fumigatus* Cel7A CBH1 disclosed as SEQ ID NO: 6 in WO2011/057140 and *Aspergillus fumigatus* CBH II disclosed as SEQ ID NO: 18 in WO 2011/057140.

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Examples of Preferred Processes of the Invention

In a preferred embodiment the invention relates processes for producing ethanol from starch-containing material comprising the steps of:
i) liquefying the starch-containing material at a temperature above the initial gelatinization temperature using an alpha-amylase derived from *Bacillus stearothermophilus;*
ii) saccharifying using a glucoamylase;
iii) fermenting using a fermenting organism;
wherein the fermenting organism is *Saccharomyces cerevisiae* MBG4851 (deposited under Accession No. V14/

004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In an embodiment a protease is added in saccharification and/or fermentation or SSF.

In a preferred embodiment the invention relates processes for producing ethanol from starch-containing material comprising the steps of:
i) liquefying the starch-containing material at a temperature above the initial gelatinization temperature using:
an alpha-amylase derived from *Bacillus stearothermophilus* comprising a double deletion at positions I181+G182, and optionally a N193F substitution; (using SEQ ID NO: 1 for numbering);
ii) saccharifying using a glucoamylase derived from a strain of *Gloephyllum*, such as *Gloephyllum serpiarium* or *Gloephyllum trabeum*;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature above the initial gelatinization temperature using:
an alpha-amylase derived from *Bacillus stearothermophilus*;
a protease having a thermostability value of more than 20% determined as Relative Activity at 80° C./70° C., preferably derived from *Pyrococcus furiosus* and/or *Thermoascus aurantiacus*; and
optionally a *Penicillium oxalicum* glucoamylase;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature above the initial gelatinization temperature using:
an alpha-amylase, preferably derived from *Bacillus stearothermophilus*, comprising a double deletion at positions I181+G182, and optionally a N193F substitution (using SEQ ID NO: 1 for numbering) and having a T½ (min) at pH 4.5, 85° C., 0.12 mM CaCl₂ of at least 10;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature between 80-90° C.:
an alpha-amylase, preferably derived from *Bacillus stearothermophilus*, having a T½ (min) at pH 4.5, 85° C., 0.12 mM CaCl₂ of at least 10;
a protease, preferably derived from *Pyrococcus furiosus* and/or *Thermoascus aurantiacus*, having a thermostability value of more than 20% determined as Relative Activity at 80° C./70° C.;
optionally a *Penicillium oxalicum* glucoamylase
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature above the initial gelatinization temperature using:
an alpha-amylase derived from *Bacillus stearothermophilus* having a double deletion at positions I181+G182, and optional substitution N193F; and optionally further one of the following set of substitutions:
E129V+K177L+R179E;
V59A+Q89R+E129V+K177L+R179E+H208Y+K220P+N224L+Q254S:
V59A+Q89R+E129V+K177L+R179E+Q254S+M284V;
V59A+E129V+K177L+R179E+Q254S+M284V;
E129V+K177L+R179E+K220P+N224L+S242Q+Q254S
(using SEQ ID NO: 1 herein for numbering);
ii) saccharifying using a glucoamylase, such as one from a strain of *Gloephyllum*, such as a strain of *Gloeophyllum serpiarium*;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature above the initial gelatinization temperature using:
an alpha-amylase derived from *Bacillus stearothermophilus* having a double deletion at positions I181+G182, and optional substitution N193F, and optionally further one of the following set of substitutions:
E129V+K177L+R179E;
V59A+Q89R+E129V+K177L+R179E+H208Y+K220P+N224L+Q254S:
V59A+Q89R+E129V+K177L+R179E+Q254S+M284V;
V59A+E129V+K177L+R179E+Q254S+M284V;
E129V+K177L+R179E+K220P+N224L+S242Q+Q254S
(using SEQ ID NO: 1 herein for numbering).
a protease having a thermostability value of more than 20% determined as Relative Activity at 80° C./70° C., preferably derived from *Pyrococcus furiosus* and/or *Thermoascus aurantiacus*; and optionally a *Penicillium oxalicum* glucoamylase shown in SEQ ID NO: 14 having substitutions selected from the group of:

K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+Y504T; or
K79V+P11F+T65A+Q327W+E501V+Y504T (using SEQ ID NO: 14 for numbering);

ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:

i) liquefying the starch-containing material at a temperature between 80-90° C. using:

an alpha-amylase derived from *Bacillus stearothermophilus* having a double deletion at positions I181+G182, and optional substitution N193F, and further optionally one of the following set of substitutions:

E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V;
E129V+K177L+R179E+K220P+N224L+S242Q+Q254S
(using SEQ ID NO: 1 herein for numbering), a protease having a thermostability value of more than 20% determined as Relative Activity at 80° C./70° C., preferably derived from *Pyrococcus furiosus* and/or *Thermoascus aurantiacus*;

a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+Y504T; or
K79V+P11F+T65A+Q327W+E501V+Y504T (using SEQ ID NO: 14 for numbering);

ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:

i) liquefying the starch-containing material at a temperature above the initial gelatinization temperature using:

an alpha-amylase derived from *Bacillus stearothermophilus* having a double deletion at positions I181+G182, and optional substitution N193F;

a protease having a thermostability value of more than 20% determined as Relative Activity at 80° C./70° C., preferably derived from *Pyrococcus furiosus* and/or *Thermoascus aurantiacus*; and optionally a pullulanase;

a *Penicillium oxalicum* glucoamylase having a K79V substitution (using SEQ ID NO: 14 for numbering);

ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:

i) liquefying the starch-containing material at a temperature above the initial gelatinization temperature using:

an alpha-amylase, preferably derived from *Bacillus stearothermophilus*, having a T % (min) at pH 4.5, 85° C., 0.12 mM $CaCl_2$ of at least 10;

between 0.5 and 10 micro grams *Pyrococcus furiosus* protease per g DS;

ii) saccharifying using a glucoamylase selected from the group of glucoamylase derived from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*, such as *G. serpiarium* or *G. trabeum*, or a strain of the *Nigrofomes*;

iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:

i) liquefying the starch-containing material at a temperature between 80-90° C. using;

an alpha-amylase, preferably derived from *Bacillus stearothermophilus* having a double deletion at positions I181+G182, and optional substitution N193F and having a T½ (min) at pH 4.5, 85° C., 0.12 mM $CaCl_2$ of at least 10;

between 0.5 and 10 micro grams *Pyrococcus furiosus* protease per g DS;

optionally a pullulanase;

a *Penicillium oxalicum* glucoamylase;

ii) saccharifying using a glucoamylase;

iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature a temperature between 80-90° C. using;
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V
E129V+K177L+R179E+K220P+N224L+S242Q+Q254S (using SEQ ID NO: 1 herein for numbering);
between 0.5 and 10 micro grams *Pyrococcus furiosus* protease per g DS; and
optionally a pullulanase;
a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature between 80-90° C. using:
an alpha-amylase derived from *Bacillus stearothermophilus* having a double deletion I181+G182 and optional substitution N193F; and further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V
E129V+K177L+R179E+K220P+N224L+S242Q+Q254S (using SEQ ID NO: 1 herein for numbering).
a protease having a thermostability value of more than 20% determined as Relative Activity at 80° C./70° C., preferably derived from *Pyrococcus furiosus* and/or *Thermoascus aurantiacus*; and
optionally a pullulanase;
a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase selected from the group of glucoamylase derived from a strain of *Aspergillus*; or a strain of *Trichoderma*; a strain of *Talaromyces*, a strain of *Pycnoporus*; a strain of *Gloeophyllum*; and a strain of the *Nigrofomes*;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates processes for producing ethanol from starch-containing material comprising the steps of:
i) liquefying the starch-containing material at a temperature between 80-90° C. at a pH between 5.0 and 6.5 using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V
E129V+K177L+R179E+K220P+N224L+S242Q+Q254S (using SEQ ID NO: 1 herein for numbering).
a protease derived from *Pyrococcus furiosus*, preferably the one shown in SEQ ID NO: 13 herein;
a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase;
iii) fermenting using a fermenting organism; wherein the fermenting organism is *Saccharomyces cerevisiae* MBG4851 (deposited under Accession No. V14/

004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the process of the invention comprises the steps of:

i) liquefying the starch-containing material at a temperature between 80-90° C. at a pH between 5.0 and 6.5 using:
  an alpha-amylase derived from *Bacillus stearothermophilus* having a double deletion I181+G182, and optional substitution N193F; and optionally further one of the following set of substitutions:
  E129V+K177L+R179E;
  V59A+Q89R+E129V+K177L+R179E+H208Y+ K220P+N224L+Q254S;
  V59A+Q89R+E129V+K177L+R179E+Q254S+ M284V;
  V59A+E129V+K177L+R179E+Q254S+M284V
  E129V+K177L+R179E+K220P+N224L+S242Q+ Q254S (using SEQ ID NO: 1 herein for numbering).
  a protease derived from *Pyrococcus furiosus*, preferably the one shown in SEQ ID NO: 13 herein present and/or added in a dosage of 1-5 micro gram protease per gram DS, such as around 1.5 or 3 micro gram protease per gram DS;
  a *Penicillium oxalicum* glucoamylase shown in SEQ ID NO: 14 having substitutions selected from the group of:
  K79V;
  K79V+P11F+T65A+Q327F; or
  K79V+P2N+P4S+P11F+T65A+Q327F; or
  K79V+P11F+D26C+K33C+T65A+Q327F; or
  K79V+P2N+P4S+P11F+T65A+Q327W+E501V+ Y504T; or
  K79V+P2N+P4S+P11F+T65A+Q327F+E501V+ Y504T; or
  K79V+P11F+T65A+Q327W+E501V+Y504T (using SEQ ID NO: 14 for numbering);
ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having defining characteristics of strain V14/004037.

In a preferred embodiment the invention relates to processes for producing ethanol from starch-containing material comprising the steps of:
i) liquefying the starch-containing material at a temperature above the initial gelatinization temperature using an alpha-amylase derived from *Bacillus stearothermophilus*;
ii) saccharifying using a glucoamylase;
iii) fermenting using a fermenting organism;
wherein the fermenting organism has one or more, such as all, of the following properties and defining characteristics:
  increases ethanol yield compared to Ethanol Red™ under the same process conditions;
  produces reduced levels of lactic acid compared to Ethanol Red™ under the same process conditions;
  produces reduced levels of glycerol compared to Ethanol Red™ under the same process conditions;
  reduces the level of acetaldehyde in fermentation compared to Ethanol Red™ under the same process condition;
  increases the oil yield compared to Ethanol Red™ under the same process conditions;
  has faster fermentation kinetics compared to Ethanol Red™ under the same process conditions.

In an embodiment the invention relates to processes of recovering/extracting oil from an ethanol production process of the invention comprising the steps of:

In a preferred embodiment the invention relates processes for producing ethanol from starch-containing material comprising the steps of:
i) liquefying the starch-containing material at a temperature a temperature between 80-90° C. using;
  an alpha-amylase derived from *Bacillus stearothermophilus*, optionally having a double deletion I181+G182, and optional substitution N193F, and optionally further one of the following set of substitutions:
  E129V+K177L+R179E;
  V59A+Q89R+E129V+K177L+R179E+H208Y+K220P+ N224L+Q254S;
  V59A+Q89R+E129V+K177L+R179E+Q254S+M284V:
  V59A+E129V+K177L+R179E+Q254S+M284V
  E129V+K177L+R179E+K220P+N224L+S242Q+Q254S (using SEQ ID NO: 1 herein for numbering);
  optionally a *Pyrococcus furiosus* protease; and
  optionally a *Penicillium oxalicum* glucoamylase, optionally having the sequence shown in SEQ ID NO: 14 having substitutions selected from the group of:
  K79V;
  K79V+P11F+T65A+Q327F; or
  K79V+P2N+P4S+P11F+T65A+Q327F; or
  K79V+P11F+D26C+K33C+T65A+Q327F; or
  K79V+P2N+P4S+P11F+T65A+Q327W+E501V+ Y504T; or
  K79V+P2N+P4S+P11F+T65A+Q327F+E501V+Y504T; or
  K79V+P11F+T65A+Q327W+E501V+Y504T (using SEQ ID NO: 14 for numbering);
ii) saccharifying using a glucoamylase;
iii) fermenting using a fermenting organism;
iv) recovering the fermentation product to form whole stillage;
v) separating the whole stillage into thin stillage and wet cake;
vi) optionally concentrating the thin stillage into syrup;
wherein oil is recovered/extracted downstream from fermentation step iii) and wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851 or a derivative of *Saccharomyces* strain V14/004037 having defining characteristics of strain V14/004037.

In an embodiment the fermenting organism is a non-recombinant *Saccharomyces* strain, preferably non-recombinant *Saccharomyces cerevisiae* strain. In a preferred embodiment the fermenting organism is a non-recombinant *Saccharomyces* strain, preferably non-recombinant *Saccharomyces cerevisiae* strain produced using the method described and concerned in U.S. Pat. No. 8,257,959-BB.

Use of Strain V14/004037 (*Saccharomyces cerevisiae* MBG4851) or a Derivative of Strain V14/004037

Strain V14/004037 (*Saccharomyces cerevisiae* MBG4851) or a derivative of strain V14/004037 may according to the invention be used for increasing the ethanol yield in fermentation.

Strain V14/004037 (*Saccharomyces cerevisiae* MBG4851) or a derivative of strain V14/004037 may according to the invention be used to produce reduced levels of lactic acid compared to Ethanol Red™ under the same process conditions.

Strain V14/004037 (*Saccharomyces cerevisiae* MBG4851) or a derivative of strain V14/004037 may according to the invention be used to produce reduced levels of glycerol compared to Ethanol Red™ under the same process conditions;

Strain V14/004037 (*Saccharomyces cerevisiae* MBG4851) or a derivative of strain V14/004037 may according to the invention be used for reducing the level of acetaldehyde in fermentation.

In an embodiment the invention relates to the use of strain V14/004037 (*Saccharomyces cerevisiae* MBG4851) or a derivative of strain V14/004037 for reducing the level of acetaldehyde in fermentation compared to Ethanol Red™ under the same process condition.

The liquefied mash to be fermented has been subjected to alpha-amylase and from 0.5-50 micro gram protease per gram DS, such as 1-5 micro gram protease per gram DS, such as around 1.5 or 3 micro gram protease per gram DS.

The protease may be a bacterial protease. The protease may be derived from a strain of the bacterium *Pyrococcus*, such as a strain of *Pyrococcus furiosus* (pfu protease), such as or SEQ ID NO: 13 herein. The protease may be the one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 13 herein.

The alpha-amylase used for liquefying may be of bacterial origin, such as from the genus *Bacillus*, such as a strain of *Bacillus stearothermophilus*, in particular a variant of a *Bacillus stearothermophilus* alpha-amylase, such as the one shown in SEQ ID NO: 1 herein. In a preferred embodiment the *Bacillus stearothermophilus* alpha-amylase variant is selected from the group with the following mutations:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A+Q89R+E129V+K177L+R179E+Q254S+M284V;

I181*+G182*+N193F+V59A+E129V+K177L+R179E+Q254S+M284V; and

I181*+G182*+N193F+E129V+K177L+R179E+K220P+N224L+S242Q+Q254S (using SEQ ID NO: 1 for numbering).

The liquefied mash, to be fermented, has in an embodiment been subjected to alpha-amylase, glucoamylase and from 0.5-50 micro gram protease per gram DS, such as 1-5 micro gram protease per gram DS such as around 1.5 or 3 micro gram protease per gram DS.

The glucoamylase may be derived from a strain of the genus *Penicillium*, especially a strain of *Penicillium oxalicum* disclosed in SEQ ID NOs: 9 or 14 herein.

The glucoamylase may be a variant of the *Penicillium oxalicum* glucoamylase having a K79V substitution (using the mature sequence shown in SEQ ID NO: 14 for numbering).

In a preferred embodiment the *Penicillium oxalicum* glucoamylase has a K79V substitution (using SEQ ID NO: 14 for numbering) and further one of the following:

P11F+T65A+Q327F;

P2N+P4S+P11F+T65A+Q327F (using SEQ ID NO: 14 for numbering).

Yeast of the Invention

The invention relates in one embodiment to a strain of *Saccharomyces cerevisiae* deposited under the Budapest Treaty at the National Measurement Institute (NMI) having deposit accession no. V14/004037.

The majority of the world's fuel ethanol is produced by industrial scale fermentation of starch-based sugars, in substrates such as corn mash. During industrial scale fermentation, the yeast encounter various physiological challenges including variable concentrations of sugars, high concentrations of yeast metabolites such as ethanol, glycerol, organic acids, osmotic stress, as well as potential competition from contaminating microbes such as wild yeasts and bacteria. As a consequence, many *Saccharomyces* strains are not suitable for use in industrial fermentation. The most widely used commercially available industrial strain of *Saccharomyces* (i.e. for industrial scale fermentation) is the *Saccharomyces cerevisiae* strain used, for example, in the product Ethanol Red. This strain is well suited to industrial ethanol production, however improved strains of *Saccharomyces cerevisiae* are needed.

WO 2011/035392 describes strain NMI V09/024011, which is a strain of *Saccharomyces cerevisiae* which produces higher levels of ethanol from corn mash than strains of *Saccharomyces cerevisiae* used in the fuel ethanol industry such as Ethanol Red™. However, a limitation of strain NMI V09/024011 is that its fermentation kinetics are slower than those of Ethanol Red. Also, the higher levels of ethanol that V09/024011 produces relative to Ethanol Red were only found when corn mash has been heavily supplemented with exogenous sugar sources such as dextrin. Under such conditions, mash fermentations need to be run for extended periods, beyond what are normally encountered in the industrial process. As such, high concentration sugar supplementation is not necessarily of industrial relevance and may not be encountered at scale. The inventors have now produced strain no. V14/004037 which is capable of producing even higher ethanol yields from endogenously occurring corn sugar consumed under the conditions encountered in industrial scale fermentation, such as those encountered during fermentation of corn mash, than V09/024011 or commercially available industrial *Saccharomyces cerevisiae* strains used in the ethanol industry. Strain no. V14/004037 also exhibits faster fermentation kinetics than strain no. V09/024011. As described herein, the levels of ethanol produced by strain no. V14/004037 under the conditions encountered during industrial fermentation of corn mash are greater than that of the commercially available industrial yeast strains such as Ethanol Red, and that of strain V09/024011. Thus, strain no. V14/004037 has the necessary characteristics for industrial production of ethanol from substrates such as corn mash.

Strain no. V14/004037 is a non-recombinant *Saccharomyces cerevisiae* strain developed by breeding which:

(a) produces a higher titre of ethanol at 50 hrs fermentation than strains V09/024011 and Ethanol Red, under the same conditions in a corn mash fermentation;

(b) produces a higher amount of ethanol than V09/024011 at 20 h, under the same conditions in a corn mash fermentation;

(c) produces less glycerol than Ethanol Red and V09/024011 under the same conditions in a corn mash fermentation.
(d) leaves less glucose remaining following fermentation than Ethanol Red and V09/024011 under the same conditions in a corn mash fermentation;
(e) leaves less maltose remaining following fermentation than Ethanol Red and V09/024011 under the same conditions in a corn mash fermentation.

As used herein, a defining characteristics of strain no. V14/004037 is any one or more of the following characteristics:
  (a) produces ethanol in an amount in the range from 13.0 to 14.0% w/v at 32° C. in 44 hours in a corn mash fermentation;
  (b) produces glycerol in an amount in the range from 1.300 to 1.400% w/v at 32° C. in 44 hours in a corn mash fermentation;
  (c) produces a ratio of % w/v ethanol produced to % w/v glycerol produced following fermentation of corn mash at 32° C. for 50 hours in the range from 9 to 11;
  (d) produces a ratio of % w/v ethanol produced to % w/v glucose remaining following fermentation of corn mash at 32° C. for 50 hours in the range from 100 to 900, 200 to 850, 300 to 850, 400 to 850;
  (e) produces a ratio of % w/v ethanol produced to % w/v maltose remaining following fermentation of corn mash at 32° C. for 50 hours in the range from 30 to 50.

Typically, the ethanol produced from fermentation of corn mash is produced from fermentation of sugars that are endogenous to the corn mash. Sugars that are endogenous to the corn mash are sugars that are derived from the corn rather than sugars that are added from an exogenous source.

Strain V14/004037 is also capable of growth in media in which xylose is the sole carbon source. In this regard, strain V14/004037 produces about a 7-fold increase in biomass when grown under the conditions specified in Test T1. As a consequence, strain V14/004037 can be readily distinguished from:
  (a) naturally occurring strains of Saccharomyces;
  (b) contaminating strains of Saccharomyces that do not utilize xylose; and
  (c) other strains used in the ethanol industry that do not have the ethanol producing capabilities of strain V14/004037 and/or do not exhibit about a 7-fold increase in biomass in Test T1.

As current wild type and industrial strains of Saccharomyces are not capable of growth on xylose at the rate at which strain V14/004037 grows on xylose, strain V14/004037 is readily differentiated from current wild type strains of Saccharomyces and strains of Saccharomyces that are used in the ethanol industry prior to the present invention such as Ethanol Red.

The invention also relates to a derivative of Saccharomyces strain V14/004037. As used herein, a "derivative of strain V14/004037" is a strain derived from strain V14/004037, including through mutagenesis, recombinant DNA technology, mating, cell fusion, or cytoduction between yeast strains. The strain derived from strain V14/004037 may be a direct progeny (i.e. the product of a mating between strain V14/004037 and another strain or itself), or a distant progeny resulting from an initial mating between V14/004037 and another strain or itself, followed by a large number of subsequent matings.

In one embodiment, a derivative of strain V14/004037 is a hybrid strain produced by culturing a first yeast strain with strain V14/004037 under conditions which permit combining of DNA between the first yeast strain and strain V14/004037.

In one embodiment, a derivative of strain V14/004037 may be prepared by:
  (a) culturing a first yeast strain with a second yeast strain, wherein the second yeast strain is strain V14/004037 or a derivative of strain V14/004037, under conditions which permit combining of DNA between the first yeast strain and the second yeast strain; and
  (b) isolating hybrid strains; and
  (c) optionally repeating steps (a) and (b) using a hybrid strain isolated in step (b) as the first yeast strain and/or the derivative of strain V14/004037.

In one embodiment, the derivative of strain V14/004037 exhibits one or more defining characteristic of strain V14/004037. Derivatives of Saccharomyces which exhibit one or more defining characteristics of strain V14/004037 are produced using strain V14/004037. In this regard, strain V14/004037 forms the basis for preparing other strains having defining characteristics of strain V14/004037. For example, strains of Saccharomyces which exhibit one or more defining characteristics of strain V14/004037 can be derived from strain V14/004037 using methods such as classical mating, cell fusion, or cytoduction between yeast strains, mutagenesis or recombinant DNA technology.

In one embodiment, a derivative of strain V14/004037 which exhibits one or more defining characteristics of strain V14/004037 may be produced by:
  (a) culturing a first yeast strain with a second yeast strain, wherein the second yeast strain is strain V14/004037 or a derivative of strain V14/004037, under conditions which permit combining of DNA between the first yeast strain and the second yeast strain;
  (b) screening or selecting for a derivative of strain V14/004037, such as screening or selecting for a derivative with increased ethanol production in corn mash compared to the first strain, and/or screening or selecting for a hybrid which produces less glycerol in corn mash compared to the first strain;
  (c) optionally repeating steps (a) and (b) with the screened or selected strain as the first yeast strain and/or the second yeast strain, until a derivative of strain V14/004037 is obtained which exhibits one or more defining characteristics of strain V14/004037.

The first yeast strain may be any strain of yeast if the DNA of the strain can be combined with the second yeast strain using methods such as classical mating, cell fusion or cytoduction. Typically, the first yeast strain is a Saccharomyces strain. More typically, the first yeast strain is a Saccharomyces cerevisiae strain. Saccharomyces cerevisiae is as defined by Kurtzman (2003) FEMS Yeast Research vol 4 pp. 233-245. The first yeast strain may have desired properties which are sought to be combined with the defining characteristics of strain V14/004037. The first yeast strain may be, for example, any Saccharomyces cerevisiae strain, such as for example Ethanol Red, V09/024011. It will also be appreciated that the first yeast strain may be strain V14/004037 or a strain which exhibits one or more defining characteristics of strain V14/004037.

The first and second yeast strains are cultured under conditions which permit combining of DNA between the yeast strains. As used herein, "combining of DNA" between yeast strains refers to combining of all or a part of the genome of the yeast strains. Combining of DNA between yeast strains may be by any method suitable for combining DNA of at least two yeast cells, and may include, for example, mating methods which comprise sporulation of the yeast strains to produce haploid cells and subsequent hybridising of compatible haploid cells; cytoduction; or cell fusion such as protoplast fusion.

In one embodiment, culturing the first yeast strain with the second yeast, under conditions which permit combining of DNA between the first yeast strain and the second yeast strain, comprises:
(i) sporulating the first yeast strain and the second yeast strain;
(ii) germinating and hybridizing spores produced by the first yeast strain with spores produced by the second yeast strain.

In one embodiment, the method of producing a derivative of strain V14/004037 which exhibits one or more defining characteristics of strain V14/004037, comprises:
(a) providing: (i) a first yeast strain; and (ii) a second yeast strain, wherein the second yeast strain is strain V14/004037 or a derivative of strain V14/004037;
(b) sporulating the first yeast strain and the second yeast strain;
(c) germinating and hybridising the spores of the first yeast strain with germinated spores of the second yeast strain;
(d) screening or selecting for a derivative of strain V14/004037, such as screening or selecting for a derivative with increased ethanol production in corn mash compared to the first strain, and/or screening or selecting for a hybrid which produces less glycerol in corn mash compared to the first strain;
(e) optionally repeating steps (b) to (d) with the screened or selected strain as the first and/or second yeast strain.

Methods for sporulating, germinating and hybridising yeast strains, and in particular, Saccharomyces strains, are known in the art and are described in, for example, Ausubel, F. M. et al., (1997) Current Protocols in Molecular Biology, Volume 2, pages 13.2.1 to 13.2.5 (John Willey & Sons Inc); Chapter 7, "Sporulation and Hybridisation of yeast" by R. R. Fowell, in "The Yeasts" vol 1, A. H. Rose and J. S. Harrison (Eds), 1969, Academic Press.

In one embodiment, the yeast strains may be cultured under conditions which permit cell fusion. Methods for the generation of intraspecific or interspecific hybrids using cell fusion techniques are described in, for example, Spencer et al. (1990) in, Yeast Technology, Spencer J F T and Spencer D M (Eds), Springer Verlag, New York.

In another embodiment, the yeast strains may be cultured under conditions which permit cytoduction. Methods for cytoduction are described in, for example, Inge-Vechymov et al. (1986) Genetika 22: 2625-2636; Johnston (1990) in, Yeast technology, Spencer J F T and Spencer D M (Eds), Springer Verlag, New York.

In one embodiment, screening or selecting for derivatives of strain V14/004037 comprises screening or selecting for a derivative with increased ethanol production in corn mash compared to the first strain, and/or screening or selecting for a hybrid which produces less glycerol in corn mash compared to the first strain.

In another embodiment, the yeast cells may be screened or selected for strains which have one or more of the following characteristics:
(a) produces an amount of ethanol that is in the range from an amount higher than that produced by strain Ethanol Red to the amount produced by strain V14/004037, under the same conditions in a corn mash fermentation;
(b) produces an amount of glycerol that is in the range from an amount that is less than the amount produced by Ethanol Red to the amount produced by strain V14/004037, under the same conditions in a corn mash fermentation
(c) produces a ratio of ethanol to glycerol that is in the range from a ratio higher than the ratio of ethanol to glycerol of Ethanol Red to a ratio that is about the same as the ratio of ethanol to glycerol of strain V14/004037, under the same conditions in a corn mash fermentation.
(d) produces a ratio of ethanol to glucose that is in the range from a ratio higher than the ratio of ethanol to glucose of Ethanol Red to a ratio that is about the same as the ratio of ethanol to glucose of strain V14/004037 under the same conditions in a corn mash fermentation;
(e) produces a ratio of ethanol to maltose that is in the range from a ratio higher than the ratio of ethanol to maltose of Ethanol Red to a ratio that is about the same as the ratio of ethanol to maltose of strain V14/004037 under the same conditions in a corn mash fermentation.

Methods for determining the amount of ethanol and glycerol produced by a strain are known in the art. For example, methods for testing for determining the amount of ethanol and glycerol produced by a strain during fermentation of corn mash are described in, for example, WO 2011/035392. Once the amount of ethanol and glycerol produced are known, the ratio of ethanol/glycerol can be readily determined. Accordingly, strains can be readily screened for production levels of ethanol and/or glycerol using known methods.

In one embodiment, a derivative of strain V14/004037 which exhibits one or more defining characteristics of strain V14/004037 may be a mutant of strain V14/004037. Methods for producing mutants of Saccharomyces yeast, and specifically mutants of Saccharomyces cerevisiae, are known in the art and described in, for example, Lawrence C. W. (1991) Methods in Enzymology, 194: 273-281.

In another embodiment, a derivative of strain V14/004037 which exhibits one or more defining characteristics of strain V14/004037 may be a recombinant derivative of strain V14/004037. A recombinant derivative of strain V14/004037 is a strain produced by introducing into strain V14/004037 a nucleic acid using recombinant DNA technology. Methods for the introduction of nucleic acid into Saccharomyces yeast cells, and in particular strains of Saccharomyces, are known in the art and are described in, for example, Ausubel, F. M. et al. (1997), Current Protocols in Molecular Biology, Volume 2, pages 13.7.1 to 13.7.7, published by John Wiley & Sons Inc.

The invention also relates to methods for the production of ethanol using the strain described herein. In one form, strain V14/004037 or a derivative strain which exhibits the defining characteristics of strain V14/004037 is incubated with a substrate comprising fermentable sugars under conditions that allow fermentation of the fermentable sugars. The fermentable sugars may be one or more of glucose, galactose, maltose, fructose and sucrose. Typically, the fermentable sugar is glucose. While strain V14/004037 is well suited to fermentation in corn mash, it is envisaged the strain may also be suitable for other fermentation processes. Accordingly, the source of the fermentable sugar in the substrate may be, for example, hydrolysed starch, hydrolysed cellulose, molasses, cane juice, grape juice, fruit juice, glucose, maltodextrins, raw sugar juice, galactose, sucrose, or any other forms of fermentable sugars. In one form, the source of fermentable sugar in the substrate is hydrolysed starch. Typically, the starch is obtained from a substrate such as corn mash. In preparing the substrate, the grain is typically ground and mixed with water and hydrolytic enzyme(s) under conditions which result in hydrolysis of the starch and release of fermentable sugars such as glucose. Typical enzymes for hydrolysis of the starch include a-amylase, amyloglucosidase, pullulanase, b-amylase, glucoamylase, or mixtures thereof. Enzymes suitable for hydrolysis are available from, for example, Novozymes or Genencor Inc. In one form, substrate is provided in the form of corn mash. Corn mash is typically produced by: (a) grinding corn to form a meal; (b) mixing the meal with water; and (c) hydrolyzing the starch in the corn meal. Methods for preparation of corn mash are known in the art and described in, for example, Thomas, K. C. et al., (2001) Journal of Applied Microbiology, volume 90, pages 819-828. Methods for the preparation of other starch-based substrates including sorghum, starch streams and combinations thereof are also known in the art and described in, for example, Kwiatkowski J. R. et al. (2003) Industrial Crops and Products 23: 288-296 and Bothast R. J. and Schlicher M. A. (2005) Applied Microbial Biotechnology 67: 19-25

The fermentation is carried out at a temperature which permits fermentation of the fermentable sugars. Typically, the temperature at which the fermentation is carried out is from 25-34° C.

The fermentation results in an alcoholic mash comprising ethanol and residual sugars in solution, and a particulate portion comprising residual solids including yeast. Ethanol is isolated from the mash using methods know in the art such as distillation or filtration.

Methods for fermentation and distillation are known in the art and are described in, for example, Kwiatkowski J. R. et al. (2003) Industrial Crops and Products 23: 288-296 and Bothast R. J. and Schlicher M. A. (2005) Applied Microbial Biotechnology 67: 19-25

The invention further relates to a method of producing distiller's grain. Distiller's grains may be produced from the residual solids produced in the fermentation using methods known in the art and described in, for example, U.S. Pat. No. 7,572,353. Because *Saccharomyces* strain V14/004037 reduces the level of residual sugars remaining following fermentation, the distiller's grain which results from fermentation using strain V14/004037 has a lowered glucose content and is therefore more stable and less prone to charring, caramelisation or contamination with unwanted microorganisms.

Furthermore, lower glycerol content in distillers grains is a process advantage because less time is required for drying the distiller's grains. In addition, less glycerol in the distiller's grains results in improved flowability, and further results in distiller's grains which has a higher nutrient content (e.g. higher protein).

As used herein, the singular forms "a", "an" and "the" include plural reference unless the context clearly indicates otherwise. Thus, for example, a reference to "a cell" includes a plurality of such cells. Unless defined otherwise, all technical and scientific terms used herein have the same meaning as commonly understood by one of ordinary skill in the art.

As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Test T1

Step 1: Yeast strains are streaked onto 2% w/v D-glucose 1% bacteriological peptone and 0.5% yeast extract medium solidified with 2% agar using standard microbiological techniques.

Step 2: After incubation for 72 hours at 30° C., yeast cells are taken from plates using a sterile microbiological loop and inoculated to an $OD_{600}$ (Optical Density at 600 nm) of between 0.1 and 0.2 units ($OD_{600}$ at $T_0$) in 50 ml of broth containing xylose (5% w/v), Difco Yeast Nitrogen Base w/o amino acids (0.67%), citric acid (0.3%) and trisodium citrate (0.7%) in distilled water in a 250 ml Erlenmeyer flask. An $OD_{600}$ of 0.1 unit is equal to approximately $9 \times 10^5$ yeast cells/mL. D-(+)-Xylose, minimum 99% can be obtained from Sigma-Aldrich.

Step 3: Cultures are incubated at 30 deg Celsius with shaking at 220 rpm (10 cm orbital diameter) for 48 hours.

Step 4: After 48 hours incubation, $OD_{600}$ of culture is measured ($OD_{600}$ at $T_{48}$).

Step 5: The fold increase in biomass is determined by the equation:

$$OD_{600} \text{ at } T_{48}/OD_{600} \text{ at } T_0.$$

Composition of the Invention

In this aspect the invention relates to a formulated *Saccharomyces* yeast composition comprising a yeast strain of the invention and a naturally occurring and/or a nonenaturally occurring component.

As mentioned above a *Saccharomyces* yeast strain, in particular *Saccharomyces cerevisiae* yeast strain, of the invention, may according to the invention may be in any viable form, including crumbled, dry, including active dry and instant, compressed, cream (liquid) form etc. In a preferred embodiment the *Saccharomyces cerevisiae* yeast strain of the invention is dry yeast, such as active dry yeast or instant yeast. In a preferred embodiment the *Saccharomyces cerevisiae* yeast strain of the invention is crumbled yeast. In a preferred embodiment the *Saccharomyces cerevisiae* yeast strain is compressed yeast. In an embodiment the *Saccharomyces cerevisiae* yeast strain of the invention is cream yeast.

In an embodiment the invention relates to a composition comprising a *Saccharomyces* yeast of the invention, in particular *Saccharmyces* MBG4851 and one or more of the component selected from the group consisting of: surfactants, emulsifiers, gums, swelling agent, and antioxidants and other processing aids.

Surfactant

According to the invention the composition may comprise a *Saccharomyces* yeast of the invention, in particular *Saccharmyces* MBG4851 and any suitable surfactants. In an embodiment the surfactant(s) is/are an anionic surfactant, cationic surfactant, and/or nonionic surfactant.

Emulsifier

According to the invention the composition may comprise a *Saccharomyces* yeast of the invention, in particular *Saccharmyces* MBG4851 and any suitable emulsifier. In an embodiment the emulsifier is a fatty-acid ester of sorbitan. In an embodiment the emulsifier is selected from the group of sorbitan monostearate (SMS), citric acid esters of monodiglycerides, polyglycerolester, fatty acid esters of propylene glycol.

In an embodiment the composition of the invention comprises a *Saccharomyces* yeast of the invention, in particular *Saccharmyces* MBG4851, and Olindronal SMS, Olindronal SK, or Olindronal SPL including composition concerned in European Patent No. 1,724,336 (hereby incorporated by reference). These products are commercially available from Bussetti, Austria, for active dry yeast.

Gum

According to the invention the composition may comprise a *Saccharomyces* yeast of the invention, in particular *Saccharmyces* MBG4851 and any suitable gum. In an embodiment the gum is selected from the group of carob, guar, tragacanth, arabic, xanthan and acacia gum, in particular for cream, compressed and dry yeast.

Swelling Agents

According to the invention the composition may comprise a *Saccharomyces* yeast of the invention, in particular *Saccharmyces* MBG4851 and any suitable swelling agent. In an embodiment the swelling agent is methyl cellulose or carboxymethyl cellulose.

Antioxidant

According to the invention the composition may comprise a *Saccharomyces* yeast of the invention, in particular *Saccharmyces* MBG4851, and any suitable anti-oxidant. In an embodiment the antioxidant is butylated hydroxyanisol (BHA) and/or butylated hydroxytoluene (BHT), or ascorbic acid (vitamin C), particular for active dry yeast.

As used herein, the singular forms "a", "an" and "the" include plural reference unless the context clearly indicates otherwise. Thus, for example, a reference to "a cell" includes a plurality of such cells. Unless defined otherwise, all technical and scientific terms used herein have the same meaning as commonly understood by one of ordinary skill in the art.

As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Various references are cited herein, the disclosures of which are incorporated by reference in their entireties.

Materials & Methods

Materials:

Alpha-Amylase A ("AAA"): *Bacillus stearothermophilus* alpha-amylase with the mutations I181*+G182*+N193F truncated to 491 amino acids (using SEQ ID NO: 1 herein for numbering)

Alpha-Amylase F: Commercial alpha-amylase sold under the trade name Fuelzyme™ by Verinium, USA.

Alpha-Amylase 369 ("AA369"): *Bacillus stearothermophilus* alpha-amylase with the mutations: I181*+G182*+N193F+V59A+Q89R+E129V+K177L+R179E+Q254S+M284V truncated to 491 amino acids (using SEQ ID NO: 1 herein for numbering);

*Penicillium oxalicum* glucoamylase variant PE498 ("PoAMG498"): *Penicillium oxalicum* glucoamylase variant having the following mutations: K79V+P2N+P4S+P11F+T65A+Q327F (using SEQ ID NO: 14 herein for numbering):

Protease Pfu ("PFU"): Protease derived from *Pyrococcus furiosus* shown in SEQ ID NO: 13 herein.

Protease X: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353.

Glucoamylase SA ("GSA") comprises a blend comprising *Talaromyces emersonii* glucoamylase disclosed in WO99/28448 (SEQ ID NO: 19 herein), *Trametes cingulata* glucoamylase disclosed as SEQ ID NO: 2 in WO 06/69289 and SEQ ID NO: 20 herein, and *Rhizomucor pusillus* alpha-amylase with *Aspergillus niger* glucoamylase linker and SBD disclosed as SEQ ID NO: 16 herein with the following substitutions: G128D+D143N (activity ratio AGU:AGU:FAU(F): approx. 30:7:1).

Cellulase VD ("CVD"): Cellulolytic composition derived from *Trichoderma reesei* comprising GH61A polypeptide having cellulolytic enhancing activity derived from a strain of *Penicillium emersonii* (SEQ ID NO: 2 in WO 2011/041397), *Aspergillus fumigatus* beta-glucosidase variant (SEQ ID NO: 2 in WO 2005/047499 with the following substitutions: F100D, S283G, N456E, F512Y) disclosed in WO 2012/044915; *Aspergillus fumigatus* Cel7A CBH1 disclosed as SEQ ID NO: 6 in WO2011/057140 and *Aspergillus fumigatus* CBH II disclosed as SEQ ID NO: 18 in WO 2011/057140.

Yeast:

ETHANOL RED™ ("ER"): *Saccharomyces cerevisiae* yeast available from Fermentis/Lesaffre, USA.

MBG4851: *Saccharomyces cerevisiae* yeast (non-recombinant) deposited by Microbiogen Pty Ltd, Unit E2, Lane Cove Business Park, 16 Mars Road, Lane Cove, NSW 2066, Australia under the terms of the Budapest Treaty with the National Measurement Institute, Victoria, Australia) and given the following accession number:

| Deposit | Accession Number | Date of Deposit |
|---|---|---|
| MBG4851 | V14/004037 | Feb. 17, 2014 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention.

Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

Methods

Identity:

The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLO- SUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Protease Assays

AZCL-Casein Assay

A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

Glucoamylase activity (AGU) Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |

| -continued | |
|---|---|
| Color reaction: | |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

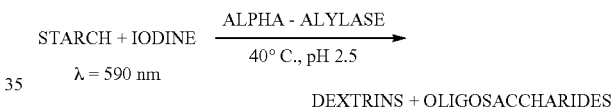

blue/violet t=23 sec. decoloration

Standard Conditions/Reaction Conditions:

| Substrate: | Soluble starch, approx. 0.17 g/L |
|---|---|
| Buffer: | Citrate, approx. 0.03M |
| Iodine (I2): | 0.03 g/L |
| CaCl2: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Alpha-Amylase Activity (KNU-A)

Alpha amylase activity is measured in KNU(A) Kilo Novozymes Units (A), relative to an enzyme standard of a declared strength.

Alpha amylase in samples and α-glucosidase in the reagent kit hydrolyze the substrate (4,6-ethylidene($G_7$)-p-nitrophenyl($G_1$)-α,D-maltoheptaoside (ethylidene-$G_7$PNP) to glucose and the yellow-colored p-nitrophenol.

The rate of formation of p-nitrophenol can be observed by Konelab 30. This is an expression of the reaction rate and thereby the enzyme activity.

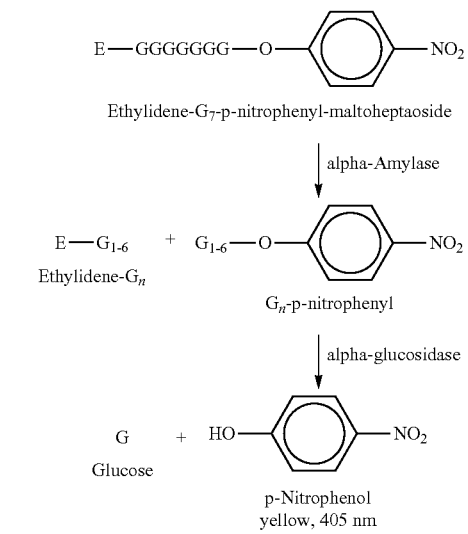

The enzyme is an alpha-amylase with the enzyme classification number EC 3.2.1.1.

| Parameter | Reaction conditions |
| --- | --- |
| Temperature | 37° C. |
| pH | 7.00 (at 37° C.) |
| Substrate conc. | Ethylidene-$G_7$PNP, R2: 1.86 mM |
| Enzyme conc. (conc. of high/low standard in reaction mixture) | 1.35-4.07 KNU(A)/L |
| Reaction time | 2 min |
| Interval kinetic measuring time | 7/18 sec. |
| Wave length | 405 nm |
| Conc. of reagents/chemicals critical for the analysis | α-glucosidase, R1: ≥3.39 kU/L |

A folder EB-SM-5091.02-D on determining KNU-A activity is available upon request to Novozymes A/S, Denmark, which folder is hereby included by reference.

Alpha-Amylase Activity KNU(S)

BS-amylase in samples and the enzyme alpha-glucosidase in the reagent kit hydrolyze substrate (4,6-ethylidene(G7)-p-nitrophenyl(G1)-alpha-D-maltoheptaoside (ethylidene-G7PNP)) to glucose and the yellow-colored p-nitrophenol.

The rate of formation of p-nitrophenol can be observed by Konelab 30. This is an expression of the reaction rate and thereby the enzyme activity.

Reaction Conditions

| Reaction: | |
| --- | --- |
| pH | 7.15 |
| Temperature | 37° C. |
| Reaction Time | 180 sec |
| Detection | |
| Wavelength | 405 nm |
| Measuring Time | 120 sec |

Unit Definition

*Bacillus stearothermophilus* amylase (BS-amylase) activity is measured in KNU(S), Kilo Novo Units (sterarothermophilus), relative to an enzyme standard of a declared strength.

This analytical method is described in more details in EB-SM-0221.02 (incorporated by reference) available from Novozymes A/S, Denmark, on request.

Determination of FAU(F)

FAU(F) Fungal Alpha-Amylase Units (Fungamyl) is measured relative to an enzyme standard of a declared strength.

| Reaction conditions | |
| --- | --- |
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1 numbering)) and alpha-amylase variants thereof was determined by incubating the reference alpha-amylase and variants at pH 4.5 and 5.5 and temperatures of 75° C. and 85° C. with 0.12 mM CaCl$_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM CaCl$_2$, pH 5.0). Twenty microliters enzyme sample was transferred to 48-well PCR MTP and 180 microliters stability buffer (150 mM acetate, 150 mM MES, 0.01% Triton X100, 0.12 mM CaCl$_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM CaCl$_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T½ (min)=T(min)*LN (0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Preparation of Protease Variants and Test of Thermostability
Strains and Plasmids

*E. coli* DH12S (available from Gibco BRL) was used for yeast plasmid rescue. pJTP000 is a *S. cerevisiae* and *E. coli* shuttle vector under the control of TPI promoter, constructed from pJC039 described in WO 01/92502, in which the *Thermoascus aurantiacus* M35 protease gene (WO 03048353) has been inserted.

*Saccharomyces cerevisiae* YNG318 competent cells: MATa Dpep4[cir+] ura3-52, leu2-D2, his 4-539 was used for protease variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar (2%) and $H_2O$ (approx. 761 ml) is autoclaved together, and the separately sterilized SC-glucose solution is added to the agar solution.

YPD: Bacto peptone 20 g/l, yeast extract 10 g/l, 20% glucose 100 ml/l.

YPD+Zn: YPD+0.25 mM $ZnSO_4$.

PEG/LiAc solution: 40% PEG4000 50 ml, 5 M Lithium Acetate 1 ml.

96 well Zein micro titre plate:

Each well contains 200 microL of 0.05-0.1% of zein (Sigma), 0.25 mM $ZnSO_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "*Current protocols in Molecular Biology*", John Wiley and Sons, 1995; Harwood, C. R. and Cutting, S. M. (Eds.).

Yeast Transformation

Yeast transformation was performed using the lithium acetate method. 0.5 microL of vector (digested by restriction endonucleases) and 1 microL of PCR fragments is mixed. The DNA mixture, 100 microL of YNG318 competent cells, and 10 microL of YEAST MAKER carrier DNA (Clontech) is added to a 12 ml polypropylene tube (Falcon 2059). Add 0.6 ml PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The *Thermoascus* M35 protease gene was amplified with the primer pair Prot F (SEQ ID NO: 4) and Prot R (SEQ ID NO: 5). The resulting PCR fragments were introduced into *S. cerevisiae* YNG318 together with the pJC039 vector (described in WO 2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 6) and AM35 (SEQ ID NO:7) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL $H_2O$ | 1 | 94° C. 2 min |
| 2 beads puRe Taq Ready-To-Go PCR (Amersham Biosciences) | 2 | 94° C. 30 sec |
|  | 3 | 55° C. 30 sec |
| 0.5 micro L X 2 100 pmole/microL of primers | 4 | 72° C. 90 sec |
| 0.5 microL template DNA | 2-4 | 25 cycles |
|  | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex. 60° C. and 65° C., 70° C. and 75° C., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml of 12.5% azo-casein in ethanol in 96 ml of 20 mM sodium acetate, pH 4.5, containing 0.01% triton-100 and 0.25 mM ZnSO₄) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglucosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al. (2001), Appl. Environ. Microbiol. 67, 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH4)2SO4 in small aliquots (corresponding to approx. 2.0-2.2 M (NH4)2SO4 not taking the volume increase into account when adding the compound).
3. After the final addition of (NH4)2SO4, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 ml 50 mM Na-acetate pH 4.0.
6. Filter the sample by vacuum suction using a 0.22 μm PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. # PRAK 11/08).
2. With stirring, 250 microL of substrate solution is transferred to a 1.5 ml Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

Results

TABLE 2

Relative activity of protease variants. Numbering of substitution(s) starts from N-terminal of the mature peptide in amino acids 1 to 177 of SEQ ID NO: 3.

| Variant | Substitution(s) | Relative activity 65° C./60° C. |
|---|---|---|
| WT | none | 31% |
| JTP004 | S87P | 45% |
| JTP005 | A112P | 43% |
| JTP008 | R2P | 71% |
| JTP009 | D79K | 69% |
| JTP010 | D79L | 75% |
| JTP011 | D79M | 73% |
| JTP012 | D79L/S87P | 86% |
| JTP013 | D79L/S87P/A112P | 90% |
| JTP014 | D79L/S87P/A112P | 88% |
| JTP016 | A73C | 52% |
| JTP019 | A126V | 69% |
| JTP021 | M152R | 59% |

TABLE 3

Relative activity of protease variants. Numbering of substitution(s) starts from N-terminal of the mature peptide in amino acids 1 to 177 of SEQ ID NO: 3.

| Variant | Substitution(s) and/ or deletion (S) | 70° C./ 65° C. | 75° C./ 65° C. | 75° C./ 70° C. |
|---|---|---|---|---|
| WT | none | 59% | 17% | |
| JTP036 | D79L/S87P/D142L | 73% | 73% | |
| JTP040 | T54R/D79L/S87P | | 71% | |
| JTP042 | Q53K/D79L/S87P/I173V | | 108% | |
| JTP043 | Q53R/D79L/S87P | | 80% | |
| JTP045 | S41R/D79L/S87P | | 82% | |
| JTP046 | D79L/S87P/Q158W | | 96% | |
| JTP047 | D79L/S87P/S157K | | 85% | |
| JTP048 | D79L/S87P/D104R | | 88% | |
| JTP050 | D79L/S87P/A112P/D142L | | 88% | |
| JTP051 | S41R/D79L/S87P/A112P/D142L | | | 102% |
| JTP052 | D79L/S87P/A112P/D142L/S157K | | | 111% |
| JTP053 | S41R/D79L/S87P/A112P/D142L/S157K | | | 113% |
| JTP054 | ΔS5/D79L/S87P | | | 92% |
| JTP055 | ΔG8/D79L/S87P | | | 95% |
| JTP059 | C6R/D79L/S87P | | | 92% |
| JTP061 | T46R/D79L/S87P | | | 111% |
| JTP063 | S49R/D79L/S87P | | | 94% |
| JTP064 | D79L/S87P/N88R | | | 92% |
| JTP068 | D79L/S87P/T114P | | | 99% |
| JTP069 | D79L/S87P/S115R | | | 103% |
| JTP071 | D79L/S87P/T116V | | | 105% |
| JTP072 | N26R/D79L/S87P | | 92% | |
| JTP077 | A27K/D79L/S87P/A112P/D142L | | | 106% |
| JTP078 | A27V/D79L/S87P/A112P/D142L | | | 100% |
| JTP079 | A27G/D79L/S87P/A112P/D142L | | | 104% |

TABLE 4

Relative activity of protease variants. Numbering of substitution(s) starts from N-terminal of the mature peptide in amino acids 1 to 177 of SEQ ID NO: 3.

| Variant | Substitution(s) and/or deletion(s) | Relative activity 75° C./65° C. | Remaining activity 80° C. | Remaining activity 84° C. |
|---|---|---|---|---|
| JTP082 | ΔS5/D79L/S87P/A112P/D142L | 129% | | 53% |
| JTP083 | T46R/D79L/S87P/A112P/D142L | 126% | | |
| JTP088 | Y43F/D79L/S87P/A112P/D142L | 119% | | |
| JTP090 | D79L/S87P/A112P/T124L/D142L | 141% | | |
| JTP091 | D79L/S87P/A112P/T124V/D142L | 154% | 43% | |
| JTP092 | ΔS5/N26R/D79L/S87P/A112P/D142L | | 60% | |
| JTP095 | N26R/T46R/D79L/S87P/A112P/D142L | | 62% | |
| JTP096 | T46R/D79L/S87P/T116V/D142L | | 67% | |
| JTP099 | D79L/P81R/S87P/A112P/D142L | | 80% | |
| JTP101 | A27K/D79L/S87P/A112P/T124V/D142L | | 81% | |
| JTP116 | D79L/Y82F/S87P/A112P/T124V/D142L | | 59% | |
| JTP117 | D79L/Y82F/S87P/A112P/T124V/D142L | | 94% | |
| JTP127 | D79L/S87P/A112P/T124V/A126V/D142L | | 53% | |

TABLE 5

Relative activity of protease variants. Numbering of substitution(s) starts from N-terminal of the mature peptide in amino acids 1 to 177 of SEQ ID NO: 3.

| Variant | Substitutions | Relative activity 75° C./70° C. | Relative activity 80° C./70° C. | Relative activity 85° C./70° C. |
|---|---|---|---|---|
| JTP050 | D79L S87P A112P D142L | 55% | 23% | 9% |
| JTP134 | D79L Y82F S87P A112P D142L | | 40% | |
| JTP135 | S38T D79L S87P A112P A126V D142L | | 62% | |
| JTP136 | D79L Y82F S87P A112P A126V D142L | | 59% | |
| JTP137 | A27K D79L S87P A112P A126V D142L | | 54% | |
| JTP140 | D79L S87P N98C A112P G135C D142L | 81% | | |
| JTP141 | D79L S87P A112P D142L T141C M161C | 68% | | |
| JTP143 | S36P D79L S87P A112P D142L | 69% | | |
| JTP144 | A37P D79L S87P A112P D142L | 57% | | |
| JTP145 | S49P D79L S87P A112P D142L | 82% | 59% | |
| JTP146 | S50P D79L S87P A112P D142L | 83% | 63% | |
| JTP148 | D79L S87P D104P A112P D142L | 76% | 64% | |
| JTP161 | D79L Y82F S87P A112P D142L | | 30% | 12% |
| JTP180 | S70V D79L Y82F S87G Y97W A112P D142L | | 52% | |
| JTP181 | D79L Y82F S87G Y97W D104P A112P D142L | | 45% | |
| JTP187 | S70V D79L Y82F S87G A112P D142L | | 45% | |
| JTP188 | D79L Y82F S87G D104P A112P D142L | | 43% | |
| JTP189 | D79L Y82F S87G A112P A126V D142L | | 46% | |
| JTP193 | Y82F S87G S70V D79L D104P A112P D142L | | 15% | |
| JTP194 | Y82F S87G D79L D104P A112P A126V D142L | | 22% | |
| JTP196 | A27K D79L Y82F S87G D104P A112P A126V D142L | | 18% | |
| JTP196 | A27K D79L Y82F S87G D104P A112P A126V D142L | 102% | 55% | |
| JTP210 | A27K Y82F S87G D104P A112P A126V D142L | 107% | 36% | |
| JTP211 | A27K D79L Y82F D104P A112P A126V D142L | 94% | 44% | |
| JTP213 | A27K Y82F D104P A112P A126V D142L | 103% | 37% | |

Example 3

Temperature Profile of Selected Variants Using Purified Enzymes

Selected variants showing good thermo-stability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:
1) Mix 10 ul of 10 ug/ml enzyme solutions and 100 ul of 0.025% zein solution in a micro titer plate (MTP).
2) Incubate at various temperatures for 60 min.
3) Add 10 ul of 100% trichloroacetic acid (TCA) solution.
4) Centrifuge MTP at 3500 rpm for 5 min.
5) Take out 15 ul to a new MTP containing 100 ul of BCA assay solution (Pierce Cat#:23225, BCA Protein Assay Kit).
6) Incubate for 30 min. at 60° C.
7) Measure A562.

The results are shown in Table 6. All of the tested variants showed an improved thermo-stability as compared to the wt protease.

TABLE 6

Zein-BCA assay

Sample incubated 60 min at indicated temperatures (° C.) (μg/ml Bovine serum albumin equivalent peptide released)

| WT/Variant | 60° C. | 70° C. | 75° C. | 80° C. | 85° C. | 90° C. | 95° C. |
|---|---|---|---|---|---|---|---|
| WT | 94 | 103 | 107 | 93 | 58 | 38 | |
| JTP050 | 86 | 101 | 107 | 107 | 104 | 63 | 36 |
| JTP077 | 82 | 94 | 104 | 105 | 99 | 56 | 31 |
| JTP188 | 71 | 83 | 86 | 93 | 100 | 75 | 53 |
| JTP196 | 87 | 99 | 103 | 106 | 117 | 90 | 38 |

Example 4

Characterization of *Penicillium oxalicum* Glucoamylase

The *Penicillium oxalicum* glucoamylase is disclosed in SEQ ID NO: 9 herein.

Substrate.
Substrate: 1% soluble starch (Sigma S-9765) in deionized water
Reaction buffer: 0.1 M Acetate buffer at pH 5.3
Glucose concentration determination kit: Wako glucose assay kit (LabAssay glucose, WAKO, Cat#298-65701).
Reaction Condition.

20 microL soluble starch and 50 microL acetate buffer at pH 5.3 were mixed. 30 microL enzyme solution (50 micro g enzyme protein/ml) was added to a final volume of 100 microL followed by incubation at 37° C. for 15 min.

The glucose concentration was determined by Wako kits.
All the work carried out in parallel.
Temperature Optimum.

To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 7.

TABLE 7

| | Temperature optimum | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat Stability.

To assess the heat stability of the *Penicillium oxalicum* glucoamylase the Reaction condition assay was modified in that the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 8.

TABLE 8

| | Heat stability | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH Optimum.

To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 9.

TABLE 9

| | pH optimum | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH Stability.

To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 10.

TABLE 10

| pH stability | | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Thermostability of Protease Pfu.

The thermostability of the *Pyrococcus furiosus* protease (Pfu S) purchased from Takara Bio Inc, (Japan) was tested using the same methods as in Example 2. It was found that the thermostability (Relative Activity) was 110% at (80° C./70° C.) and 103% (90° C./70° C.) at pH 4.5.

Example 6

Cloning of *Penicillium oxalicum* Strain Glucoamylase Gene
Preparation of *Penicillium oxalicum* Strain cDNA.

The cDNA was synthesized by following the instruction of 3' Rapid Amplification of cDNA End System (Invitrogen Corp., Carlsbad, Calif., USA).

Cloning of *Penicillium oxalicum* Strain Glucoamylase Gene.

The *Penicillium oxalicum* glucoamylase gene was cloned using the oligonucleotide primer shown below designed to amplify the glucoamylase gene from 5' end.

```
                                 (SEQ ID NO: 22)
Sense primer:
5'-ATGCGTCTCACTCTATTATCAGGTG-3'
```

The full length gene was amplified by PCR with Sense primer and AUAP (supplied by 3' Rapid Amplification of cDNA End System) by using Platinum HIFI Taq DNA polymerase (Invitrogen Corp., Carlsbad, Calif., USA). The amplification reaction was composed of 5 µl of 10×PCR buffer, 2 µl of 25 mM MgCl$_2$, 1 µl of 10 mM dNTP, 1 µl of 10 uM Sense primer, 1 µl of 10 uM AUAP, 2 µl of the first strand cDNA, 0.5 µl of HIFI Taq, and 37.5 µl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° C. for 40 secs, 68° C. for 2 min; final extension at 68° C. for 10 mins.

The obtained PCR fragment was cloned into pGEM-T vector (Promega Corporation, Madison, Wis., USA) using a pGEM-T Vector System (Promega Corporation, Madison, Wis., USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen and Zellkulturen GmbH (DSMZ) on Nov. 23, 2009, and assigned accession number as DSM 23123.

Example 7

Expression of Cloned *Penicillium oxalicum* Glucoamylase

The *Penicillium oxalicum* glucoamylase gene was re-cloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                                  (SEQ ID NO: 23)
5' ACACAACTGGGGATCCACCATGCGTCTCACTCTATTATC Primer R:
                                  (SEQ ID NO: 24)
5' AGATCTCGAGAAGCTTAAAACTGCCACACGTCGTTGG
```

A PCR reaction was performed with plasmid AMG 1 in order to amplify the full-length gene. The PCR reaction was composed of 40 µg of the plasmid AMG 1 DNA, 1 µl of each primer (100 µM); 12.5 µl of 2× Extensor Hi-Fidelity master mix (Extensor Hi-Fidelity Master Mix, ABgene, United Kingdom), and 9.5 µl of PCR-grade water. The PCR reaction was performed using a DYAD PCR machine (Bio-Rad Laboratories, Inc., Hercules, Calif., USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (GE Healthcare, United Kingdom) according to manufacturer's instructions. DNA corresponding to the *Penicillium oxalicum* glucoamylase gene was cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

A 2 µl volume of the ligation mixture was used to transform 25 µl of Fusion Blue *E. coli* cells (included in the IN-FUSION™ Dry-Down PCR Cloning Kit). After a heat shock at 42° C. for 45 sec, and chilling on ice, 250 µl of SOC medium was added, and the cells were incubated at 37° C.

at 225 rpm for 90 min before being plated out on LB agar plates containing 50 μg of ampicillin per ml, and cultivated overnight at 37° C. Selected colonies were inoculated in 3 ml of LB medium supplemented with 50 μg of ampicillin per ml and incubated at 37° C. at 225 rpm overnight. Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ XYZ1471-4.

Protoplasts of *Aspergillus niger* MBin118 were prepared as described in WO 95/02043. One hundred μl of protoplast suspension were mixed with 2.5 μg of the XYZ1471-4 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys. Acta 133:51-56) (1M) plates supplemented with 10 mM acetamide and 15 mM CsCl and added as a top layer on COVE sucrose (1M) plates supplemented with 10 mM acetamide and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation.

The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifugated and the supernatant was filtrated using 0.2 μm membrane filters.

Alpha-Cyclodextrin Affinity Gel.

Ten grams of Epoxy-activated Sepharose 6B (GE Healthcare, Chalfont St. Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of Glucoamylase from Culture Broth.

Culture broth from fermentation of *A. niger* MBin118 harboring the glucoamylase gene was filtrated through a 0.22 μm PES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found.

Example 8

Construction and Expression of a Site-Directed Variant of *Penicillium oxalicum* Glucoamylase Two PCR reactions were performed with plasmid XYZ1471-4, described in Example 7, using primers K79V F and K79VR shown below, which were designed to substitute lysine K at position 79 from the mature sequence to valine (V) and primers F-NP003940 and R-NP003940 shown below, which were designed based on the known sequence and added tags for direct cloning by IN-FUSION™ strategy.

```
Primer K79V F 18 mer
                                        (SEQ ID NO: 25)
GCAGTCTTTCCAATTGAC Primer K79V R 18 mer
                                        (SEQ ID NO: 26)
AATTGGAAAGACTGCCCG Primer F-NP003940:
                                        (SEQ ID NO: 27)
5' ACACAACTGGGGATCCACCATGCGTCTCACTCTATTATC Primer R-NP003940:
                                        (SEQ ID NO: 28)
5' AGATCTCGAGAAGCTTAAAACTGCCACACGTCGTTGG
```

The PCR was performed using a PTC-200 DNA Engine under the conditions described below.

| PCR reaction system: | | Conditions: |
|---|---|---|
| 48.5 micro L H2O | 1 | 94° C. 2 min |
| 2 beads puRe Taq Ready-To-Go PCR | 2 | 94° C. 30 sec |
| Beads (Amersham Biosciences) | 3 | 55° C. 30 sec |
| 0.5 micro L X 2100 pmole/micro L Primers | 4 | 72° C. 90 sec |
| (K79V F + Primer R-NP003940, K79V R + | 2-4 | 25 cycles |
| Primer F-NP003940) | 5 | 72° C. 10 min |
| 0.5 micro L Template DNA | | |

DNA fragments were recovered from agarose gel by the Qiagen gel extraction Kit according to the manufacturer's instruction. The resulting purified two fragments were cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

The ligation mixture was used to transform *E. coli* DH5α cells (TOYOBO). Selected colonies were inoculated in 3 ml of LB medium supplemented with 50 μg of ampicillin per ml and incubated at 37° C. at 225 rpm overnight. Plasmid DNA from the selected colonies was purified using Qiagen plasmid mini kit (Qiagen) according to the manufacturer's instructions. The sequence of *Penicillium oxalicum* glucoamylase site-directed variant gene sequence was verified before heterologous expression and one of the plasmids was selected for further expression, and was named pPoPE001.

Protoplasts of *Aspergillus niger* MBin118 were prepared as described in WO 95/02043. One hundred μl of protoplast suspension were mixed with 2.5 μg of the pPoPE001 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 1% agarose L (Nippon Gene) in COVE sucrose (Cove, 1996, Biochim. Biophys. Acta 133:51-56) supplemented with 10 mM acetamide and 15 mM CsCl and added as a top layer on COVE sucrose plates supplemented with 10 mM acetamide and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE gel in order to identify the best transformants based on the ability to produce large amount of the glucoamylase.

Example 9

Purification of Site-Directed Po AMG Variant PE001

The selected transformant of the variant and the strain expressing the wild type *Penicillium oxalicum* glucoamylase described in Example 6 was cultivated in 100 ml of YP-2% maltose medium and the culture was filtrated through a 0.22 μm PES filter, and applied on a alpha-cyclodextrin affinity gel column previously equilibrated in 50 mM NaOAc, 150 mM NaCl, pH 4.5 buffer. Unbound materials was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase samples were then dialyzed against 20 mM NaOAc, pH 5.0.

Example 10

Characterization of PE001 Protease Stability

40 μl enzyme solutions (1 mg/ml) in 50 mM sodium acetate buffer, pH 4.5, were mixed with 1/10 volume of 1 mg/ml protease solutions such as aspergillopepsin I described in Biochem J. 1975 April; 147(1):45-53, or the commercially available product from Sigma and aorsin described in Biochemical journal [0264-6021] Ichishima yr: 2003 vol: 371 iss: Pt 2 pg: 541 and incubated at 4 or 32° C. overnight. As a control experiment, H$_2$O was added to the sample instead of proteases. The samples were loaded on SDS-PAGE to see if the glucoamylases are cleaved by proteases.

In SDS-PAGE, PE001 only showed one band corresponding to the intact molecule, while the wild type glucoamylase was degraded by proteases and showed a band at lower molecular size at 60 kCa.

TABLE 11

The result of SDS-PAGE after protease treatment

| Protease | Wild type glucoamylase | | | | PE001 | | | | control |
|---|---|---|---|---|---|---|---|---|---|
| | aspergillopepsin I | | aorsin | | aspergillopepsin I | | aorsin | | |
| Incubation temperature (° C.) | 4 | 32 | 4 | 32 | 4 | 32 | 4 | 32 | 4 |
| intact glucoamylase (ca. 70 kDa) | 100% | 90% | 40% | 10% | 100% | 100% | 100% | 100% | 100% |
| cleaved glucoamylase (ca. 60 kDa) | N.D. | 10% | 60% | 90% | N.D. | N.D. | N.D | N.D. | N.D. |

N.D.: not detected.

Example 11

Less Cleavage During Cultivation

*Aspergillus* transformant of the variant and the wild type *Penicillium oxalicum* glucoamylase were cultivated in 6-well MT plates containing 4× diluted YP-2% maltose medium supplemented with 10 mM sodium acetate buffer, pH4.5, at 32° C. for 1 week.

The culture supernatants were loaded on SDS-PAGE.

TABLE 12

The result of SDS-PAGE of the culture supernatants

| | Wild type glucoamylase | PE001 |
|---|---|---|
| intact glucoamylase(ca. 70 kDa) | 90% | 100% |
| cleaved glucoamylase (ca. 60 kDa) | 10% | N.D. |

N.D.: not detected.

The wild type glucoamylase was cleaved by host proteases during fermentation, while the variant yielded only intact molecule.

Example 12

Glucoamylase Activity of Variant Compared to Parent

The glucoamylase activity measures as AGU as described above was checked for the purified enzymes of the wild type *Penicillium oxalicum* and the variant glucoamylase.

The Glucoamylase Unit (AGU) was defined as the amount of enzyme, which hydrolyzes 1 micromole maltose per minute under the standard conditions (37° C., pH 4.3, substrate: maltose 100 mM, buffer: acetate 0.1 M, reaction time 6 minutes).

TABLE 13

| Relative specific activity | AGU/mg |
|---|---|
| *Penicillium oxalicum* wt | 100% |
| *Penicillium oxalicum* PE001 (SEQ ID NO: 14 + K79V substitution) | 102% |

Example 13

Purification of Glucoamylase Variants Having Increased Thermostability

The variants showing increased thermostability may be constructed and expressed similar to the procedure described in Example 8. All variants were derived from the PE001. After expression in YPM medium, variants comprising the T65A or Q327F substitution was micropurified as follows:

Mycelium was removed by filtration through a 0.22 μm filter. 50 μl column material (alpha-cyclodextrin coupled to Mini-Leak divinylsulfone-activated agarose medium according to manufacturer's recommendations) was added to the wells of a filter plate (Whatman, Unifilter 800 μl, 25-30 μm MBPP). The column material was equilibrated with binding buffer (200 mM sodium acetate pH 4.5) by two times addition of 200 μl buffer, vigorous shaking for 10 min (Heidolph, Titramax 101, 1000 rpm) and removal of buffer by vacuum (Whatman, UniVac 3). Subsequently, 400 μl culture supernatant and 100 μl binding buffer was added and the plate incubated 30 min with vigorous shaking. Unbound material was removed by vacuum and the binding step was repeated. Normally 4 wells were used per variant. Three washing steps were then performed with 200 μl buffer of decreasing ionic strength added (50/10/5 mM sodium acetate, pH 4.5), shaking for 15 min and removal of buffer by vacuum. Elution of the bound AMG was achieved by two times addition of 100 μl elution buffer (250 mM sodium acetate, 0.1% alpha-cyclodextrin, pH 6.0), shaking for 15 min and collection of eluted material in a microtiter plate by vacuum. Pooled eluates were concentrated and buffer changed to 50 mM sodium acetate pH 4.5 using centrifugal filter units with 10 kDa cut-off (Millipore Microcon Ultracel YM-10). Micropurified samples were stored at −18° C. until testing of thermostability.

Example 14

Protein Thermal Unfolding Analysis (TSA, Thermal Shift Assay).

Protein thermal unfolding of the T65A and Q327F variants, was monitored using Sypro Orange (In-vitrogen, S-6650) and was performed using a real-time PCR instrument (Applied Biosystems; Step-One-Plus).

In a 96-well plate, 25 microliter micropurified sample in 50 mM Acetate pH4.5 at approx. 100 microgram/ml was mixed (5:1) with Sypro Orange (resulting conc.=5×; stock solution from supplier=5000×). The plate was sealed with an optical PCR seal. The PCR instrument was set at a scan-rate of 76° C. pr. hr, starting at 25° C. and finishing at 96° C.

Protein thermal unfolding of the E501V+Y504T variant, was monitored using Sypro Orange (In-vitrogen, S-6650) and was performed using a real-time PCR instrument (Applied Biosystems; Step-One-Plus).

In a 96-well plate, 15 microliter purified sample in 50 mM Acetate pH4.5 at approx. 50 microgram/ml was mixed (1:1) with Sypro Orange (resulting conc.=5×; stock solution from supplier=5000×) with or without 200 ppm Acarbose (Sigma A8980). The plate was sealed with an optical PCR seal. The PCR instrument was set at a scan-rate of 76 degrees C. pr. hr, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (ref.: Gregory et al; *J Biomol Screen* 2009 14: 700.)

TABLE 14a

| Sample | Tm (Deg. Celsius) +/− 0.4 |
| --- | --- |
| PO-AMG (PE001) | 80.3 |
| Variant Q327F | 82.3 |
| Variant T65A | 81.9 |

TABLE 14b

| Sample | Tm (Deg. Celsius) +/− 0.4 | |
| --- | --- | --- |
| Acarbose: | − | + |
| PO-AMG (PE001) | 79.5 | 86.9 |
| Variant E501V Y504T | 79.5 | 95.2 |

Example 15

Thermostability Analysis by Differential Scanning Calorimetry (DSC)

Additional site specific variants having substitutions and/or deletions at specific positions were constructed basically as described in Example 8 and purified as described in Example 11.

The thermostability of the purified Po-AMG PE001 derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 15 below.

TABLE 15

| Po-AMG name | Mutations | DSC Td (° C.) @ pH 4.0 | DSC Td (° C.) @ pH 4.8 |
| --- | --- | --- | --- |
| PE001 (SEQ ID NO: 14 + K79V) | | 82.1 | 83.4 |
| GA167 | E501V Y504T | 82.1 | |
| GA481 | T65A K161S | 84.1 | 86.0 |
| GA487 | T65A Q405T | 83.2 | |
| GA490 | T65A Q327W | 87.3 | |
| GA491 | T65A Q327F | 87.7 | |
| GA492 | T65A Q327Y | 87.3 | |
| GA493 | P11F T65A Q327F | 87.8 | 88.5 |
| GA497 | R1K D3W K5Q G7V N8S T10K P11S T65A Q327F | 87.8 | 88.0 |
| GA498 | P2N P4S P11F T65A Q327F | 88.3 | 88.4 |
| GA003 | P11F D26C K33C T65A Q327F | 83.3 | 84.0 |
| GA009 | P2N P4S P11F T65A Q327W E501V Y504T | 88.8 | |
| GA002 | R1E D3N P4G G6R G7A N8A T10D P11D T65A Q327F | 87.5 | 88.2 |
| GA005 | P11F T65A Q327W | 87.4 | 88.0 |

TABLE 15-continued

| Po-AMG name | Mutations | DSC Td (° C.) @ pH 4.0 | DSC Td (° C.) @ pH 4.8 |
|---|---|---|---|
| GA008 | P2N P4S P11F T65A Q327F E501V Y504T | 89.4 | 90.2 |
| GA010 | P11F T65A Q327W E501V Y504T | | 89.7 |
| GA507 | T65A Q327F E501V Y504T | | 89.3 |
| GA513 | T65A S105P Q327W | | 87.0 |
| GA514 | T65A S105P Q327F | | 87.4 |
| GA515 | T65A Q327W S364P | | 87.8 |
| GA516 | T65A Q327F S364P | | 88.0 |
| GA517 | T65A S103N Q327F | | 88.9 |
| GA022 | P2N P4S P11F K34Y T65A Q327F | | 89.7 |
| GA023 | P2N P4S P11F T65A Q327F D445N V447S | | 89.9 |
| GA032 | P2N P4S P11F T65A I172V Q327F | | 88.7 |
| GA049 | P2N P4S P11F T65A Q327F N502* | | 88.4 |
| GA055 | P2N P4S P11F T65A Q327F N502T P563S K571E | | 88.0 |
| GA057 | P2N P4S P11F R31S K33V T65A Q327F N564D K571S | | 89.5 |
| GA058 | P2N P4S P11F T65A Q327F S377T | | 88.6 |
| GA064 | P2N P4S P11F T65A V325T Q327W | | 88.0 |
| GA068 | P2N P4S P11F T65A Q327F D445N V447S E501V Y504T | | 90.2 |
| GA069 | P2N P4S P11F T65A I172V Q327F E501V Y504T | | 90.2 |
| GA073 | P2N P4S P11F T65A Q327F S377T E501V Y504T | | 90.1 |
| GA074 | P2N P4S P11F D26N K34Y T65A Q327F | | 89.1 |
| GA076 | P2N P4S P11F T65A Q327F I375A E501V Y504T | | 90.2 |
| GA079 | P2N P4S P11F T65A K218A K221D Q327F E501V Y504T | | 90.9 |
| GA085 | P2N P4S P11F T65A S103N Q327F E501V Y504T | | 91.3 |
| GA086 | P2N P4S T10D T65A Q327F E501V Y504T | | 90.4 |
| GA088 | P2N P4S F12Y T65A Q327F E501V Y504T | | 90.4 |
| GA097 | K5A P11F T65A Q327F E501V Y504T | | 90.0 |
| GA101 | P2N P4S T10E E18N T65A Q327F E501V Y504T | | 89.9 |
| GA102 | P2N T10E E18N T65A Q327F E501V Y504T | | 89.8 |
| GA084 | P2N P4S P11F T65A Q327F E501V Y504T T568N | | 90.5 |
| GA108 | P2N P4S P11F T65A Q327F E501V Y504T K524T G526A | | 88.6 |
| GA126 | P2N P4S P11F K34Y T65A Q327F D445N V447S E501V Y504T | | 91.8 |
| GA129 | P2N P4S P11F R31S K33V T65A Q327F D445N V447S E501V Y504T | | 91.7 |
| GA087 | P2N P4S P11F D26N K34Y T65A Q327F E501V Y504T | | 89.8 |
| GA091 | P2N P4S P11F T65A F80* Q327F E501V Y504T | | 89.9 |
| GA100 | P2N P4S P11F T65A K112S Q327F E501V Y504T | | 89.8 |
| GA107 | P2N P4S P11F T65A Q327F E501V Y504T T516P K524T G526A | | 90.3 |
| GA110 | P2N P4S P11F T65A Q327F E501V N502T Y504* | | 90.6 |

Example 16

Thermostability Analysis by Thermo-Stress Test and pNPG Assay

Starting from one of the identified substitution variants from Example 15, identified as GA008, additional variants were tested by a thermo-stress assay in which the supernatant from growth cultures were assayed for glucoamylase (AMG) activity after a heat shock at 83° C. for 5 min. After the heat-shock the residual activity of the variant was measured as well as in a non-stressed sample.

Description of Po-AMG pNPG Activity Assay:

The *Penicillium oxalicum* glucoamylase pNPG activity assay is a spectrometric endpoint assay where the samples are split in two and measured thermo-stressed and non-thermo-stressed. The data output is therefore a measurement of residual activity in the stressed samples.

Growth:

A sterile micro titer plate (MTP) was added 200 μL rich growth media (FT X-14 without Dowfax) to each well. The strains of interest were inoculated in triplicates directly from frozen stocks to the MTP. Benchmark was inoculated in 20 wells. Non-inoculated wells with media were used as assay blanks. The MTP was placed in a plastic box containing wet tissue to prevent evaporation from the wells during incubation. The plastic box was placed at 34° C. for 4 days.

Assay:

50 μL supernatant was transferred to 50 μL 0.5 M NaAc pH 4.8 to obtain correct sample pH.

50 μL dilution was transferred to a PCR plate and thermo-stressed at 83° C. for 5 minutes in a PCR machine. The remaining half of the dilution was kept at RT.

20 μL of both stressed and unstressed samples was transferred to a standard MTP. 20 μL pNPG-substrate was added to start the reaction. The plate was incubated at RT for 1 hour.

The reaction was stopped and the colour developed by adding 50 μL 0.5M $Na_2CO_3$. The yellow colour was measured on a plate reader (Molecular Devices) at 405 nm.

Buffers:

0.5 M NaAc pH 4.8

0.25 M NaAc pH 4.8

Substrate, 6 mM pNPG:

15 mg 4-nitrophenyl D-glucopyranoside in 10 mL 0.25 NaAc pH 4.8

Stop/Developing Solution:

0.5 M $Na_2CO_3$

Data Treatment:

In Excel the raw Abs405 data from both stressed and unstressed samples were blank subtracted with their respective blanks. The residual activity (% res. act.=($Abs_{unstressed}$−($Abs_{unstressed}$−$Abs_{stressed}$))/$Abs_{unstressed}$*100%) was calculated and plotted relative to benchmark, Po-amg0008.

TABLE 16

| Po-AMG name | Mutations | % residual activity |
|---|---|---|
| GA008 | P2N P4S P11F T65A Q327F E501V Y504T | 100 |
| GA085 | P2N P4S P11F T65A S103N Q327F E501V Y504T | 127 |
| GA097 | K5A P11F T65A Q327F E501V Y504T | 106 |
| GA107 | P2N P4S P11F T65A Q327F E501V Y504T T516P K524T G526A | 109 |
| GA130 | P2N P4S P11F T65A V79A Q327F E501V Y504T | 111 |
| GA131 | P2N P4S P11F T65A V79G Q327F E501V Y504T | 112 |
| GA132 | P2N P4S P11F T65A V79I Q327F E501V Y504T | 101 |
| GA133 | P2N P4S P11F T65A V79L Q327F E501V Y504T | 102 |
| GA134 | P2N P4S P11F T65A V79S Q327F E501V Y504T | 104 |
| GA150 | P2N P4S P11F T65A L72V Q327F E501V Y504T | 101 |
| GA155 | S255N Q327F E501V Y504T | 105 |

TABLE 17

| Po-AMG name | Mutations | % residual activity |
|---|---|---|
| GA008 | P2N P4S P11F T65A Q327F E501V Y504T | 100 |
| GA179 | P2N P4S P11F T65A E74N V79K Q327F E501V Y504T | 108 |
| GA180 | P2N P4S P11F T65A G220N Q327F E501V Y504T | 108 |
| GA181 | P2N P4S P11F T65A Y245N Q327F E501V Y504T | 102 |
| GA184 | P2N P4S P11F T65A Q253N Q327F E501V Y504T | 110 |
| GA185 | P2N P4S P11F T65A D279N Q327F E501V Y504T | 108 |
| GA186 | P2N P4S P11F T65A Q327F S359N E501V Y504T | 108 |
| GA187 | P2N P4S P11F T65A Q327F D370N E501V Y504T | 102 |
| GA192 | P2N P4S P11F T65A Q327F V460S E501V Y504T | 102 |
| GA193 | P2N P4S P11F T65A Q327F V460T P468T E501V Y504T | 102 |
| GA195 | P2N P4S P11F T65A Q327F T463N E501V Y504T | 103 |
| GA196 | P2N P4S P11F T65A Q327F S465N E501V Y504T | 106 |
| GA198 | P2N P4S P11F T65A Q327F T477N E501V Y504T | 106 |

Example 17

Test for Glucoamylase Activity of Thermo-Stable Variants

All of the above described variants disclosed in tables 15, 16, and 17 have been verified for Glucoamylase activity on culture supernatants using the pNPG assay described in Example 16.

Example 18

Improved Ethanol Production in Mashes Produced with Varying Levels of Pfu Protease.

The performance of MBG4851 compared to Ethanol Red™ was evaluated in liquefacts liquefied with a blend of alpha-amylase (2.1 μg EP AA369/gDS), glucoamylase (4.5 μg EP PoAMG498/g DS) and increasing levels of Pfu protease (0.0385, 1.5, and 3.0 μg EP Pfu/gDS).

Liquefaction

Liquefactions were prepared by combining ground corn, backset and tap water to a target total weight of 160 g at 32.50% Dry Solids (DS); backset was blended at 30% w/w (weight of backset per total weight of mash). Backset and ground corn from Lincolnway Energy, received on Dec. 12, 2012, were used for all liquefactions. Initial slurry pH was 5.0 and therefore, no further adjustment was needed. Next, water and enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. 2.1 μg EP AA369/gDS and 4.5 μg EP PoAMG498/gDS was added. Three Pfu doses were tested in liquefaction: 0.0385, 1.5, and 3.0 μg EP/g DS.

Yeast Strains and Preparation

The two yeast strains tested in this experiment were Ethanol Red™ (Fermentis) and MBG4851. Yeast were propagated in filter sterilized liquid media (2% w/v D-glucose, 1% peptone, and 0.5% yeast extract). Using a sterile loop under a UV hood, cells from a lawn were transferred into 25 mL of the liquid media in 50 mL sterile centrifuge tubes with a hole drilled in the top and incubated at 150 rpm in a 30° C. air shaker. Tubes were angled at approximately 30 degrees to increase aeration. Cells were harvested at 18 hours by spinning at 3000 rpm for 10 minutes and decanting the supernatant. Cells were washed once in 25 ml of water and the resulting cell pellet was resuspended in 1.5 ml tap water. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. Urea was added to each mash to a final concentration of 500 ppm. Approximately 5 grams of each mash was transferred to test tubes having a 1/64 hole drilled in the top to allow $CO_2$ release. A blend of Glucoamylase SA and Cellulase VD were dosed to each tube of mash at 110 μg EP GSA/gDS and 30 μg EP CVD/gDS. Yeast was dosed at 10e6 cells/g mash. Milli-Q water was added to each tube so that a total volume of liquid added (enzyme+ MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 μL of 40% v/v $H_2SO_4$, vortexing, centrifuging at 1460×g for 10 minutes, and filtering through a 0.45 μm Whatman PP filter. All 54 hour samples were processed without further dilution. Samples were stored at 4° C. prior to and during HPLC analysis.

TABLE 18

| HPLC System | |
|---|---|
| HPLC System | Agilent's 1100/1200 series with Chem station software Degasser, Quaternary Pump, Auto-Sampler, Column Compartment /w Heater Refractive Index Detector (RI) |
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M H2SO4 mobile phase Flow rate: 0.6 ml/min Column temperature: 65° C. RI detector temperature:00 55° C. |

Samples were analyzed for sugars (DP4+, DP3, DP2, glucose, and fructose), organic acids (lactic and acetic), glycerol, and ethanol. Tukey-Kramer analysis was done on the results using JMP software (SAS, Cary N.C.)

Results

Table 2 below shows the titers at 54 hours of fermentation for both yeasts in each of the three prepared mashes. Tukey Kramer analysis indicated that the final ethanol titers in all three mashes were not statistically different for MBG4851. When the fermenting organism was Ethanol Red, however, there was a statistically significant improvement seen with increased Pfu during liquefaction.

TABLE 19

Ethanol Titers and Tukey Kramer Analysis

| Strain | Pfu Dose (μg EP (Enzyme Protein)/g Ds) | Ethanol Titer (g/L) | Tukey Kramer Analysis |
|---|---|---|---|
| Ethanol Red | 0.0385 | 134.705 | C |
| Ethanol Red | 1.5 | 137.489 | B |
| Ethanol Red | 3.0 | 138.062 | B |
| MBG4851 | 0.0385 | 139.712 | A |
| MBG4851 | 1.5 | 139.590 | A |
| MBG4851 | 3.0 | 139.384 | A |

*Levels not connected by same letter are significantly different

MBG4851 had higher titers of ethanol than Ethanol Red under all conditions tested. Ethanol boost seen when MBG4851 is the fermenting organism, compared to Ethanol Red is seen in Table 20 below. The boost in final ethanol titer seen with MBG4851 decreased as Pfu during liquefaction, and therefore available nitrogen increased in the mashes.

TABLE 20

Ethanol Boost over Ethanol Red at varying levels of Pfu.

| Pfu Dose (μg EP/g DS) | % Boost over Ethanol Red |
|---|---|
| 0.0385 | 3.7% |
| 1.5 | 1.5% |
| 3.0 | 0.96% |

When the fermenting organism was MBG4851, Pfu dose did not have a significant effect on ethanol production. When Ethanol Red was the fermenting organism, increasing Pfu dose and therefore available nitrogen increased ethanol by at least 2%.

Example 19

Improved Ethanol Production and Reduced Pfu Requirements in Mashes Produced with Varying Levels of Pfu Protease.

The performance of MBG4851 compared to Ethanol Red™ was evaluated in liquefacts liquefied with a blend of alpha-amylase (2.1 μg EP AA369/gDS), glucoamylase (4.5 μg EP PoAMG498/g DS) and increasing levels of Pfu protease (0.0385, 1.5, and 3.0 μg EP Pfu/gDS).

The performance of MBG4851 compared to Ethanol Red was compared in liquefacts with increased levels of Pfu protease. This experiment was run with two levels of N, 0 and 500 ppm urea to determine if varying Pfu levels would have an effect with lower levels of added urea.

Liquefaction

Liquefactions were prepared by combining ground corn, backset and tap water to a target total weight of 160 g at 32.50% Dry Solids (DS); backset was blended at 30% w/w (weight of backset per total weight of mash). Backset from Lincolnway Energy, received on Dec. 12, 2012, and ground corn from Aurora were used for all liquefactions. Initial slurry pH was 5.0 and therefore, no further adjustment was needed. Next, water and enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. 2.1 μg EP AA369/gDS and 4.5 μg EP PoAMG498/g DS was added. Three Pfu doses were tested in liquefaction: 0.0385, 1.5, and 3.0 μg EP/g DS.

Yeast Strains and Preparation

The two yeast strains tested in this experiment were Ethanol Red (Fermentis) and MBG4851. Yeast were propagated in filter sterilized liquid media (2% w/v D-glucose, 1% peptone, and 0.5% yeast extract). Using a sterile loop under a UV hood, cells from a lawn were transferred into 25 mL of the liquid media in 50 mL sterile centrifuge tubes with a hole drilled in the top and incubated at 150 rpm in a 30° C. air shaker. Tubes were angled at approximately 30 degrees to increase aeration. Cells were harvested at 18 hours by spinning at 3000 rpm for 10 minutes and decanting the supernatant. Cells were washed once in 25 ml of water and the resulting cell pellet was resuspended in 1.5 ml tap water. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. Urea was added to half of each mash to a final concentration of 0 ppm and to the other half to a final concentration of 500 ppm. Approximately 5 grams of each of the resulting six mashes was transferred to test tubes having a 1/64 hole drilled in the top to allow $CO_2$ release. A blend of Glucoamylase SA (GSA) and Cellulase VD (CVD) were dosed to each tube of mash at 110 μg EP GSA/gDS and 30 μg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 μL of 40% v/v $H_2SO_4$, vortexing, centrifuging at 1460×g for 10 minutes, and filtering through a 0.45 μm Whatman PP filter. All 54 hour samples were processed without further dilution. Samples were stored at 4° C. prior to and during HPLC analysis.

TABLE 21

HPLC System

| | |
|---|---|
| HPLC System | Agilent's 1100/1200 series with Chem station software Degasser, Quaternary Pump, Auto-Sampler, Column Compartment /w Heater Refractive Index Detector (RI) |
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M H2SO4 mobile phase Flow rate: 0.6 ml/min Column temperature: 65° C. RI detector temperature: 55° C. |

Samples were analyzed for sugars (DP4+, DP3, DP2, glucose, and fructose), organic acids (lactic and acetic), glycerol, and ethanol. Tukey-Kramer analysis was done on the results using JMP software (SAS, Cary N.C.)

Results 54 hour ethanol titers were analyzed and Table 22 below shows the results.

TABLE 22

54 hour Ethanol Titers

| Urea Level | Strain | Pfu Dose (µg EP/g Ds) | Ethanol Titer (g/L) | Tukey Kramer Analysis* |
|---|---|---|---|---|
| 0 ppm | Ethanol Red | 0.0385 | 125.194 | F |
|  | Ethanol Red | 1.5 | 131.858 | CD |
|  | Ethanol Red | 3.0 | 132.379 | BCD |
|  | MBG4851 | 0.0385 | 131.262 | DE |
|  | MBG4851 | 1.5 | 134.534 | A |
|  | MBG4851 | 3.0 | 134.405 | A |
| 500 ppm | Ethanol Red | 0.0385 | 130.128 | E |
|  | Ethanol Red | 1.5 | 131.208 | DE |
|  | Ethanol Red | 3.0 | 132.531 | BC |
|  | MBG4851 | 0.0385 | 134.108 | A |
|  | MBG4851 | 1.5 | 133.336 | AB |
|  | MBG4851 | 3.0 | 133.962 | A |

*Levels not connected by same letter are significantly different

MBG4851 had higher titers of ethanol than Ethanol Red under all conditions tested. Ethanol boost seen when MBG4851 is the fermenting organism, compared to Ethanol Red is seen in Table 23 below. The boost in final ethanol titer seen with MBG4851 decreased as Pfu during liquefaction, and therefore available nitrogen increased in the mashes.

TABLE 23

Ethanol Boost over Ethanol Red with varying N and levels of Pfu

| Urea Dose | Pfu Dose (µg EP/g Ds) | % Boost over Ethanol Red |
|---|---|---|
| 0 ppm | 0.0385 | 4.85% |
|  | 1.5 | 2.03% |
|  | 3 | 1.53% |
| 500 ppm | 0.0385 | 3.06% |
|  | 1.5 | 1.62% |
|  | 3 | 1.08% |

When 500 ppm urea was used, MBG4851 once again did not need higher doses of Pfu to reach maximum ethanol. When no urea was added, MBG4851 performance increased with Pfu dose, but maxed out by 1.5 µg EP/g DS. Under both levels of nitrogen, higher doses of Pfu increased ethanol production when Ethanol Red was the fermenting organism.

Example 20

Improved Ethanol Production and Reduced Nitrogen Requirements in Backset Free Mashes Produced with Varying Levels of Pfu Protease The performance of MBG4851 compared to Ethanol Red was evaluated in liquefacts liquefied with a blend of alpha-amylase (2.1 µg EP AA369/gDS), glucoamylase (4.5 µg EP PoAMG498/g DS) and increasing levels of Pfu protease (0.0385 and 3.0 µg EP Pfu/gDS).

Example 19 showed that MBG4851 yeast had a lower nitrogen requirement than did Ethanol Red yeast. When 3 µg Pfu/g DS was used in liquefaction, MBG4851 did not need any added urea; however, adding 500 ppm urea increased ethanol yields for ER. When 0.0385 µg Pfu/g DS was used in liquefaction, MBG4851 needed somewhere between 0 and 500 ppm of added urea in fermentation. This previous example used plant backset in the liquefactions, which likely contributed some urea (as well as peptides and amino acids). Thus this was not a true urea-free test; if a plant eliminated urea usage, then no urea would be present in backset. The present example tested five different urea levels in fermentation of backset free liquefacts (0, 200, 300, 500, and 1000 ppm).

Liquefaction

Liquefactions were prepared by combining ground corn and tap water to a target total weight of 160 g at 32.50% Dry Solids (DS). Ground corn from Aurora was used for all liquefactions. pH was adjusted to 5.1 using 40% v/v sulfuric acid and 50% w/w potassium hydroxide. Next enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. 2.1 µg EP AA369/g DS and 4.5 µg EP DS PoAMG498 was added. Two Pfu doses were tested in liquefaction: 0.0385, and 3.0 µg EP/g DS.

Yeast Strains and Preparation

The two yeast strains tested in this experiment were Ethanol Red (Fermentis) and MBG4851. Yeasts were rehydrated by weighing 2.75 g of dried yeast into 50 ml of 32° C. tap water in a 125 mL Erlenmeyer flask. The flasks were then covered with parafilm and allowed to incubate in a 32° C. water bath. After 15 minutes, the flasks were swirled, but no other agitation took place. After a total of 30 minutes, the flasks were removed from the water bath. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. Urea was adjusted to the desired level and water added to maintain a consistent solids level between mashes. Approximately 5 grams of each of the resulting mashes was transferred to test tubes having a 1/64 hole drilled in the top to allow $CO_2$ release. A blend of Glucoamylase SA (GSA) and Cellulase VD (CVD) were dosed to each tube of mash at 110 µg EP GSA/gDS and 30 µg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 µL of 40% v/v H2SO4, vortexing, centrifuging at 1460×g for 10 minutes, and filtering through a 0.45 µm Whatman PP filter. All 54 hour samples were processed without further dilution. Samples were stored at 4° C. prior to and during HPLC analysis.

TABLE 24

HPLC System

| HPLC System | Agilent's 1100/1200 series with Chem station software Degasser, Quaternary Pump, Auto-Sampler, Column Compartment /w Heater Refractive Index Detector (RI) |
|---|---|

TABLE 24-continued

| | HPLC System |
|---|---|
| Column | Bio-Rad HPX-87H Ion Exclusion Column 300 mm × 7.8 mm part# 125-0140 |
| | Bio-Rad guard cartridge Cation H part# 125-0129, Holder part# 125-0131 |
| Method | 0.005M H2SO4 mobile phase |
| | Flow rate: 0.6 ml/min |
| | Column temperature: 65° C. |
| | RI detector temperature: 55° C. |

Samples were analyzed for sugars (DP4+, DP3, DP2, glucose, and fructose), organic acids (lactic and acetic), glycerol, and ethanol. Tukey-Kramer analysis was done on the results using JMP software (SAS, Cary N.C.)

Results 54 hour Ethanol titers were analyzed and the results and ethanol boosts observed shown in Table 8 below. When the lower level of Pfu was used, added urea increased ethanol titers for both yeasts up to 500 ppm added urea, at which point MBG4851 ethanol titers remained consistent. Ethanol Red titers continued to increase when 1000 ppm urea was added. When the higher level of Pfu was used during liquefaction, added urea had no effect on MBG4851 fermentation. At this level, 0 ppm added urea fermented at the same level as 1000 ppm added urea for this yeast. In the higher Pfu mash, Ethanol Red needed at least 500 ppm urea to ferment to maximum ethanol.

TABLE 25

Ethanol Titers and Observed Boosts at 54 Hours

| Pfu Dose | Urea addition | ER Ethanol (g/L) | MBG4851 Ethanol (g/L) | % Boost (MBG4851 over ER) |
|---|---|---|---|---|
| 0.0385 μg EP/g DS Pfu | 0 ppm | 93.18321 | 122.9076 | 31.9% |
| | 200 ppm | 112.2505 | 138.3888 | 23.3% |
| | 300 ppm | 120.9298 | 144.2185 | 19.3% |
| | 500 ppm | 133.3747 | 146.5595 | 9.9% |
| | 1000 ppm | 143.4957 | 146.6301 | 2.2% |
| 3.0 μg EP/g DS Pfu | 0 ppm | 141.0018 | 147.6714 | 4.7% |
| | 200 ppm | 143.957 | 147.6526 | 2.6% |
| | 300 ppm | 144.8663 | 148.2786 | 2.4% |
| | 500 ppm | 145.5638 | 148.6821 | 2.1% |
| | 1000 ppm | 145.2924 | 147.5827 | 1.6% |

Example 21

Reduced Nitrogen (Urea) Requirement to Ferment to Maximum Ethanol in Industrially Produced Corn Mash The performance of MBG4851 compared to Ethanol Red was evaluated in an industrially produced alpha-amylase (Alpha-Amylase A) liquefied corn mash with varying levels of urea supplementation.

Corn Mash

Industrially prepared corn mash was obtained from Lincolnland. Solids on this mash were measured to be 31.5% by 105° C. drying oven.

Yeast Strains and Preparation

The two yeast strains tested in this experiment were Ethanol Red (Fermentis) and MBG4851. Yeasts were rehydrated by weighing 2.75 g of dried yeast into 50 ml of 32° C. tap water in a 125 mL Erlenmeyer flask. The flasks were then covered with parafilm and allowed to incubate in a 36.5° C. water bath. After 15 minutes, the flasks were swirled, but no other agitation took place. After a total of 30 minutes, the flasks were removed from the water bath. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. Urea was adjusted to the desired level and water added to maintain a consistent solids level between mashes. Approximately 5 grams of each of the resulting mashes was transferred to test tubes having a 1/64 hole drilled in the top to allow $CO_2$ release. A blend of Glucoamylase SA (GSA) and Cellulase VD (CVD) were dosed to each tube of mash at 110 μg EP GSA/gDS and 30 μg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 μL of 40% v/v $H_2SO_4$, vortexing, centrifuging at 1460×g for 10 minutes, and filtering through a 0.45 μm Whatman PP filter. All 54 hour samples were processed without further dilution. Samples were stored at 4° C. prior to and during HPLC analysis.

TABLE 26

| | HPLC System |
|---|---|
| HPLC System | Agilent's 1100/1200 series with Chem station software |
| | Degasser, Quaternary Pump, Auto-Sampler, Column Compartment /w Heater |
| | Refractive Index Detector (RI) |
| Column | Bio-Rad HPX-87H Ion Exclusion Column 300 mm × 7.8 mm part# 125-0140 |
| | Bio-Rad guard cartridge Cation H part# 125-0129, Holder part# 125-0131 |
| Method | 0.005M $H_2SO_4$ mobile phase |
| | Flow rate: 0.6 ml/min |
| | Column temperature: 65° C. |
| | RI detector temperature: 55° C. |

Samples were analyzed for sugars (DP4+, DP3, DP2, glucose, and fructose), organic acids (lactic and acetic), glycerol, and ethanol. Tukey-Kramer analysis was done on the results using JMP software (SAS, Cary N.C.)

Results 54 hour results are shown in Table 27 below.

TABLE 27

54 Hour Ethanol Titers

| Yeast | Urea addition | Ethanol (g/L) | Tukey Kramer Analysis* |
|---|---|---|---|
| Ethanol Red | 0 ppm | 115.708 | G |
| | 150 ppm | 128.891 | F |
| | 300 ppm | 132.487 | CD |
| | 600 ppm | 133.369 | BC |
| | 1000 ppm | 133.556 | B |
| | 3000 ppm | 130.734 | E |
| MBG4851 | 0 ppm | 131.791 | D |
| | 150 ppm | 135.03 | A |
| | 300 ppm | 135.218 | A |
| | 600 ppm | 135.032 | A |

TABLE 27-continued

54 Hour Ethanol Titers

| Yeast | Urea addition | Ethanol (g/L) | Tukey Kramer Analysis* |
|---|---|---|---|
| | 1000 ppm | 135.259 | A |
| | 3000 ppm | 133.222 | BC |

*Levels not connected by same letter are significantly different

Both yeasts fermented to the lowest ethanol titer when no urea was added to the fermentations. Another similarity between both yeasts was a decrease in ethanol titer when extremely high levels of urea (3000 ppm) were added to the fermentation. MBG4851 showed that it needed 150 ppm or less of added urea to ferment this corn mash to maximum ethanol. Ethanol Red™ did not hit its maximum until somewhere between 300 and 600 ppm of urea was added. This means that at least a 2× reduction in urea addition is possible with this yeast.

Table 28 below shows that at each level of nitrogen supplementation, MBG4851 outperforms Ethanol Red by a minimum of 1.25%.

TABLE 28

Ethanol Boost when MBG4851 was compared to Ethanol Red at each level of nitrogen supplementation.

| Urea addition | % Boost (MBG4851 over ER) |
|---|---|
| 0 ppm | 13.90% |
| 150 ppm | 4.76% |
| 300 ppm | 2.06% |
| 600 ppm | 1.25% |
| 1000 ppm | 1.28% |
| 3000 ppm | 1.90% |

Example 22

Lactic Acid Reduction in Fermentations of Mashes Produced with Varying Levels of Pfu Protease.

The lactic acid levels when using MBG4851 compared to Ethanol Red™ were evaluated in liquefacts liquefied with a blend of alpha-amylase (2.1 µg EP AA369/gDS), glucoamylase (4.5 µg EP PoAMG498/g DS) and increasing levels of Pfu protease (0.0385, 1.5, and 3.0 µg EP Pfu/gDS).

Liquefaction

Experiment 1 liquefactions were prepared by combining ground corn, backset and tap water to a target total weight of 160 g at 32.50% Dry Solids (DS); backset was blended at 30% w/w (weight of backset per total weight of mash). Backset and ground corn from Lincolnway Energy, received on Dec. 12, 2012, were used for all liquefactions. Initial slurry pH was 5.0 and therefore, no further adjustment was needed. Next, water and enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. 2.1 µg EP AA369/g DS and 4.5 µg EP DS PoAMG498 was added. Three Pfu doses were tested in liquefaction: 0.0385, 1.5, and 3.0 µg EP/g DS.

Experiment 2 liquefactions were prepared by combining ground corn, backset and tap water to a target total weight of 160 g at 32.50% Dry Solids (DS); backset was blended at 30% w/w (weight of backset per total weight of mash). Backset from Lincolnway Energy, received on Dec. 12, 2012, and ground corn from Aurora were used for all liquefactions. Initial slurry pH was 5.0 and therefore, no further adjustment was needed. Next, water and enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. Three Pfu doses were tested in liquefaction: 0.0385, 1.5, and 3.0 µg EP/g Ds.

Yeast Strains and Preparation

The two yeast strains tested in this experiment were Ethanol Red (Fermentis) and MBG4851. Yeast were propagated in filter sterilized liquid media (2% w/v D-glucose, 1% peptone, and 0.5% yeast extract). Using a sterile loop under a UV hood, cells from a lawn were transferred into 25 mL of the liquid media in 50 mL sterile centrifuge tubes with a hole drilled in the top and incubated at 150 rpm in a 30° C. air shaker. Tubes were angled at approximately 30 degrees to increase aeration. Cells were harvested at 18 hours by spinning at 3000 rpm for 10 minutes and decanting the supernatant. Cells were washed once in 25 ml of water and the resulting cell pellet was resuspended in 1.5 ml tap water. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. In experiment 1, urea was added to each mash to a final concentration of 500 ppm. In experiment 2, half of each mash was adjusted to 500 ppm urea and the other half was adjusted with water to maintain consistent solids. Approximately 5 grams of each mash was transferred to test tubes having a 1/64 hole drilled in the top to allow $CO_2$ release. A blend of Glucoamylase SA (GSA) and Cellulase VD (CVD) were dosed to each tube of mash at 110 µg EP GSA/gDS and 30 µg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 µL of 40% v/v $H_2SO_4$, vortexing, centrifuging at 1460×g for 10 minutes, and filtering through a 0.45 µm Whatman PP filter. All 54 hour samples were processed without further dilution. Samples were stored at 4° C. prior to and during HPLC analysis.

TABLE 29

HPLC System

| | |
|---|---|
| HPLC System | Agilent's 1100/1200 series with Chem station software Degasser, Quaternary Pump, Auto-Sampler, Column Compartment /w Heater Refractive Index Detector (RI) |

TABLE 29-continued

| | HPLC System |
|---|---|
| Column | Bio-Rad HPX-87H Ion Exclusion Column 300 mm × 7.8 mm part# 125-0140 |
| | Bio-Rad guard cartridge Cation H part# 125-0129, Holder part# 125-0131 |
| Method | 0.005M H2SO4 mobile phase |
| | Flow rate: 0.6 ml/min |
| | Column temperature: 65° C. |
| | RI detector temperature: 55° C. |

Samples were analyzed for sugars (DP4+, DP3, DP2, glucose, and fructose), organic acids (lactic and acetic), glycerol, and ethanol.

Results

Table 30 below shows the lactic acid titers and percent reduction at 54 hours of fermentation for both yeasts in experiment 1.

TABLE 30

54 hour Lactic Acid Results

| Pfu dose | ER (g/L Lactic Acid) | MBG4851 (g/L Lactic Acid) | % Reduction with MBG4851 |
|---|---|---|---|
| 0.0385 µg EP/g DS Pfu | 2.607496 | 2.174635 | 16.60% |
| 1.5 µg EP/g DS Pfu | 2.491174 | 2.127822 | 14.59% |
| 3.0 µg EP/g DS Pfu | 2.521229 | 2.168343 | 14.00% |

Table 31 below shows the lactic acid titers and percent reduction at 54 hours of fermentation for both yeasts in experiment 2

TABLE 31

54 Hour Lactic Acid Results

| Pfu dose | ER (g/L Lactic Acid) | MBG4851 (g/L Lactic Acid) | % Reduction with MBG4851 |
|---|---|---|---|
| 0 ppm Added Urea | | | |
| 0.0385 µg EP/g DS Pfu | 2.748912 | 2.257129 | 17.89% |
| 1.5 µg EP/g DS Pfu | 2.597976 | 2.161818 | 16.79% |
| 3.0 µg EP/g DS Pfu | 2.597319 | 2.146677 | 17.35% |
| 500 ppm Added Urea | | | |
| 0.0385 µg EP/g DS Pfu | 2.77946 | 2.36138 | 15.04% |
| 1.5 µg EP/g DS Pfu | 2.653623 | 2.248402 | 15.27% |
| 3.0 µg EP/g DS Pfu | 2.656285 | 2.260516 | 14.90% |

Example 23

Lactic Acid Reduction in Fermentations of Backset Free Mashes Produced with Varying Levels of Pfu Protease The lactic acid levels when using MBG4851 compared to Ethanol Red™ were evaluated in backset free liquefacts liquefied with a blend of alpha-amylase (2.1 µg EP AA369/gDS), glucoamylase (4.5 µg EP PoAMG498/g DS) and increasing levels of Pfu protease (0.0385 and 3.0 µg EP Pfu/gDS).

Liquefaction

Liquefactions were prepared by combining ground corn and tap water to a target total weight of 160 g at 32.50% Dry Solids (DS). Ground corn from Aurora was used for all liquefactions. pH was adjusted to 5.1 using 40% v/v sulfuric acid and 50% w/w potassium hydroxide. Next enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. 2.1 µg EP AA369/g DS and 4.5 µg EP DS PoAMG498 was added. Two Pfu doses were tested in liquefaction: 0.0385 and 3.0 µg EP/g DS.

Yeast Strains and Preparation

The two yeast strains tested in this experiment were Ethanol Red (Fermentis) and MBG4851. Yeasts were rehydrated by weighing 2.75 g of dried yeast into 50 ml of 32° C. tap water in a 125 mL Erlenmeyer flask. The flasks were then covered with parafilm and allowed to incubate in a 32° C. water bath. After 15 minutes, the flasks were swirled, but no other agitation took place. After a total of 30 minutes, the flasks were removed from the water bath. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. Urea was adjusted to the desired level and water added to maintain a consistent solids level between mashes. Approximately 5 grams of each of the resulting mashes was transferred to test tubes having a 1/64 hole drilled in the top to allow $CO_2$ release. A blend of Glucoamylase SA (GSA) and Cellulase VD (CVD) were dosed to each tube of mash at 110 µg EP GSA/gDS and 30 µg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 µL of 40% v/v $H_2SO_4$, vortexing, centrifuging at 1460×g for 10 minutes, and filtering through a 0.45 µm Whatman PP filter. All 54 hour samples were processed without further dilution. Samples were stored at 4° C. prior to and during HPLC analysis.

TABLE 32

| | HPLC System |
|---|---|
| HPLC System | Agilent's 1100/1200 series with Chem station software Degasser, Quaternary Pump, Auto-Sampler, Column Compartment /w Heater Refractive Index Detector (RI) |
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M H2SO4 mobile phase Flow rate: 0.6 ml/min Column temperature: 65° C. RI detector temperature: 55° C. |

Samples were analyzed for sugars (DP4+, DP3, DP2, glucose, and fructose), organic acids (lactic and acetic), glycerol, and ethanol.

Results

Table 33 below shows the lactic acid results for this experiment. A significant reduction was seen in all mashes.

TABLE 33

54 hour Lactic Acid Results

| Pfu Dose | Added Urea | ER (g/L Lactic Acid) | MBG4851 (g/L Lactic Acid) | % Reduction with MBG4851 |
|---|---|---|---|---|
| 0.0385 µg EP/g DS Pfu | 0 ppm | 0.739 | 0.240 | 67.53% |
| | 200 ppm | 0.783 | 0.311 | 60.28% |
| | 300 ppm | 0.820 | 0.312 | 61.98% |
| | 500 ppm | 0.783 | 0.345 | 55.98% |
| | 1000 ppm | 0.909 | 0.598 | 34.22% |
| 3.0 µg EP/g DS Pfu | 0 ppm | 0.511 | 0.212 | 58.39% |
| | 200 ppm | 0.527 | 0.259 | 50.78% |
| | 300 ppm | 0.556 | 0.336 | 39.48% |
| | 500 ppm | 0.608 | 0.370 | 39.22% |
| | 1000 ppm | 0.788 | 0.503 | 36.12% |

Example 24

Lactic Acid Reduction in Fermentations of Corn Mash Produced Industrially with Alpha-Amylase A as the Liquefaction Enzyme The lactic acid levels when using MBG4851 compared to Ethanol Red were evaluated in an industrially produced alpha-amylase (Alpha-Amylase A) liquefied corn mash with varying levels of urea supplementation.

Corn Mash

Industrially prepared corn mash was obtained from Lincolnland. Solids on this mash were measured to be 31.5% by 105° C. drying oven.

Yeast Strains and Preparation

The two yeast strains tested in this experiment were Ethanol Red™ (Fermentis) and MBG4851. Yeasts were rehydrated by weighing 2.75 g of dried yeast into 50 ml of 32° C. tap water in a 125 mL Erlenmeyer flask. The flasks were then covered with parafilm and allowed to incubate in a 36.5° C. water bath. After 15 minutes, the flasks were swirled, but no other agitation took place. After a total of 30 minutes, the flasks were removed from the water bath. Total yeast concentration was determined using the YC-100 in duplicate.

Simultaneous Saccharification and Fermentation (SSF)

Penicillin was added to each mash to a final concentration of 3 ppm. The pH after liquefaction was 5.1 and was not adjusted further for SSF. Urea was adjusted to the desired level and water added to maintain a consistent solids level between mashes. Approximately 5 grams of each of the resulting mashes was transferred to test tubes having a 1/64 hole drilled in the top to allow $CO_2$ release. A blend of Glucoamylase SA (GSA) and Cellulase VD (CVD) were dosed to each tube of mash at 110 µg EP GSA/gDS and 30 µg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 54 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 µL of 40% v/v $H_2SO_4$, vortexing, centrifuging at 1460×g for 10 minutes, and filtering through a 0.45 µm Whatman PP filter. All 54 hour samples were processed without further dilution. Samples were stored at 4° C. prior to and during HPLC analysis.

TABLE 34

HPLC System

| HPLC System | Agilent's 1100/1200 series with Chem station software Degasser, Quaternary Pump, Auto-Sampler, Column Compartment /w Heater Refractive Index Detector (RI) |
|---|---|
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M H2SO4 mobile phase Flow rate: 0.6 ml/min Column temperature: 65° C. RI detector temperature: 55° C. |

Samples were analyzed for sugars (DP4+, DP3, DP2, glucose, and fructose), organic acids (lactic and acetic), glycerol, and ethanol.

Results

Table 35 below shows the 54 hour lactic acid results.

TABLE 35

54 Hour Lactic Acid Results

| Added Urea | ER (g/L Lactic Acid) | MBG4851 (g/L Lactic Acid) | % Reduction with MBG4851 |
|---|---|---|---|
| 0 ppm | 0.794 | 0.485 | 38.91% |
| 150 ppm | 0.862 | 0.514 | 40.41% |
| 300 ppm | 0.879 | 0.545 | 37.97% |
| 600 ppm | 1.022 | 0.609 | 40.45% |
| 1000 ppm | 1.104 | 0.703 | 36.34% |
| 3000 ppm | 1.430 | 0.954 | 33.26% |

Example 25

Lactic Acid Reduction in Fermentations of Corn Mash Produced Industrially with Alpha-Amylase F (Fuelzyme™) as the Liquefaction Enzyme The lactic acid levels when using of MBG4851 compared to Ethanol Red™ were evaluated in an industrially prepared Alpha-Amylase F (Fuelzyme™) liquefied corn mash.

Corn Mash

Industrially prepared corn mash was obtained from Pine Lake. Solids on this mash were measured to be 31.5% by 105° C. drying oven.

Yeast Strains and Preparation

The two yeast strains tested in this experiment were Ethanol Red (Fermentis) and MBG4851. Yeasts were rehydrated by weighing 2.75 g of dried yeast into 50 ml of 36.5° C. tap water in a 125 mL Erlenmeyer flask. The flasks were then covered with parafilm and allowed to incubate in a 36.5° C. water bath. After 15 minutes, the flasks were swirled, but no other agitation took place. After a total of 30 minutes, the flasks were removed from the water bath. Total yeast concentration was determined using the YC-100 in duplicate.

Simultaneous Saccharification and Fermentation (SSF)

Penicillin was added to each mash to a final concentration of 3 ppm. Urea was adjusted to 762 ppm and the pH adjusted to 5.0 using sulfuric acid. Approximately 5 grams of mash was transferred to test tubes having a 1/64 hole drilled in the top to allow CO2 release. A blend of Glucoamylase SA (GSA) and Cellulase VD (CVD) were dosed to each tube of mash at 110 µg EP GSA/gDS and 30 µg EP CVD/gDS. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 52 hours. Samples were vortexed periodically (in the morning and in the evening) throughout the fermentation.

HPLC Analysis

Fermentation sampling took place after 52 hours of fermentation by sacrificing 3 tubes per treatment. Each tube was processed for HPLC analysis by deactivation with 50 µL of 40% v/v $H_2SO_4$, vortexing, centrifuging at 1460×g for 10 minutes, and filtering through a 0.45 µm Whatman PP filter. All 52 hour samples were processed without further dilution. Samples were stored at 4° C. prior to and during HPLC analysis.

TABLE 36

| | HPLC System |
|---|---|
| HPLC System | Agilent's 1100/1200 series with Chem station software Degasser, Quaternary Pump, Auto-Sampler, Column Compartment /w Heater Refractive Index Detector (RI) |
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M $H_2SO_4$ mobile phase Flow rate: 0.6 ml/min Column temperature: 65° C. RI detector temperature: 55° C. |

Samples were analyzed for sugars (DP4+, DP3, DP2, glucose, and fructose), organic acids (lactic and acetic), glycerol, and ethanol.

Results

Table 37 below shows the 52 hour results.

TABLE 37

52 hour Lactic Acid Results

| ER | MBG4851 | % Reduction with MBG4851 |
|---|---|---|
| 0.876282 | 0.606876 | 30.74% |

Example 26

Lactic Acid Reduction in Fermentations of Corn Mash Produced Industrially with Liquefaction Enzyme Blend The lactic acid levels when using MBG4851 compared to Ethanol Red™ were evaluated in industrially prepared corn mash liquefied with a blend of alpha-amylase (2.1 µg EP AA369/gDS), glucoamylase (4.5 µg EP PoAMG498/g DS) and 0.0385 µg EP Pfu/g DS.

Corn Mash

Experiment 1—Industrially prepared corn mash was obtained from Flint Hills Shell Rock. Solids on this mash were measured to be 32.8% by 105° C. drying oven.

Experiment 2—Industrially prepared corn mash was obtained from One Earth Energy. Solids on this mash were measured to be 33.95% by 105° C. drying oven.

Yeast Strains and Preparation

The two yeast strains tested in these experiments were Ethanol Red (Fermentis) and MBG4851. Yeast were propagated in filter sterilized liquid media (2% w/v D-glucose, 1% peptone, and 0.5% yeast extract). Using a sterile loop under a UV hood, cells from a lawn were transferred into 25 mL of the liquid media in 50 mL sterile centrifuge tubes with a hole drilled in the top and incubated at 150 rpm in a 30° C. air shaker. Tubes were angled at approximately 30 degrees to increase aeration. Cells were harvested at 18 hours by spinning at 3000 rpm for 10 minutes and decanting the supernatant. Cells were washed once in 25 ml of water and the resulting cell pellet was resuspended in 1.5 ml tap water. Total yeast concentration was determined using the YC-100 in duplicate.

Simultaneous Saccharification and Fermentation (SSF)

Penicillin was added to each mash to a final concentration of 3 ppm. In experiment 1, urea was adjusted to 275 ppm and the pH adjusted to 5.0 using potassium hydroxide. In experiment 2, urea was adjusted to 644 ppm and the pH adjusted to 5.0 using sulfuric acid. Approximately 5 grams of mash was transferred to test tubes having a 1/64 hole drilled in the top to allow CO2 release. A blend of Glucoamylase SA (GSA) and Cellulase VD (CVD) (110 µg EP GSA/gDS and 30 µg EP CVD/gDS) and Glucoamylase SA alone (110 µg EP GSA/gDS) were dosed to each tube of mash. Yeast was dosed at 10e6 cells/g mash. Milli-Q water was added to each tube so that a total volume of liquid added (enzyme+MQ water) to each tube would be equally proportionate to the mash weight. Fermentations took place in a 32° C. water bath for 52 hours. Samples were vortexed periodically (in the morning and in the evening) throughout the fermentation.

HPLC Analysis

Fermentation sampling took place after 54 hours of fermentation by sacrificing 3 tubes per treatment. Each tube was processed for HPLC analysis by deactivation with 50 µL of 40% v/v $H_2SO_4$, vortexing, centrifuging at 1460×g for 10 minutes, and filtering through a 0.45 µm Whatman PP filter. All 52 hour samples were processed without further dilution. Samples were stored at 4° C. prior to and during HPLC analysis.

TABLE 38

| | HPLC System |
|---|---|
| HPLC System | Agilent's 1100/1200 series with Chem station software Degasser, Quaternary Pump, Auto-Sampler, Column Compartment /w Heater Refractive Index Detector (RI) |
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M $H_2SO_4$ mobile phase Flow rate: 0.6 ml/min Column temperature: 65° C. RI detector temperature: 55° C. |

Samples were analyzed for sugars (DP4+, DP3, DP2, glucose, and fructose), organic acids (lactic and acetic), glycerol, and ethanol.

Results

Table 39 below shows the results from Experiment 1

TABLE 39

Shell Rock Lactic Acid Results

| Glucoamylase | ER (g/L Lactic Acid) | MBG4851 (g/L Lactic Acid) | % Reduction with MBG4851 |
|---|---|---|---|
| GSA + CVD | 0.9543 | 0.6984 | 26.82% |
| GSA | 0.9894 | 0.7439 | 24.81% |

Table 40 below shows the results from Experiment 2

TABLE 40

One Earth Lactic Acid Results

| Glucoamylase | ER (g/L Lactic Acid) | MBG4851 (g/L Lactic Acid) | % Reduction with MBG4851 |
|---|---|---|---|
| GSA + CVD | 1.1601 | 0.8618 | 25.71% |
| GSA | 1.1548 | 0.8523 | 26.20% |

Example 27

Reduced Lactic Acid Accumulation During Bioreactor Fermentations of Industrially Produced Alpha-Amylase A Corn Mash.

The lactic acid levels when using of MBG4851 compared to Ethanol Red were evaluated in an industrially prepared Alpha-Amylase A liquefied corn mash.

Corn Mash

Industrially prepared corn mash was obtained from Lincolnland. Solids on this mash were measured to be 32.95% by moisture balance.

Yeast Strains and Propagation

The two yeast strains tested in this experiment were Ethanol Red (Fermentis) and MBG4851.

The target solids percentage in the propagation was 20%, 607 ml of mash was added to 393 ml of water to reach a 1000 ml propagation volume at 20% solids. Lactrol was added at a concentration of 0.024 grams per liter. Urea nitrogen was added at a concentration of 1500 ppm, by adding 3 ml of a 50% urea solution. Glucoamylase dose was calculated to be 0.075 g per 1 L fermenter. As an inoculum, 2.08 grams of dried yeast were weighed out, added to 40 ml of water preheated to 36.5° C., and allowed to rehydrate for 30 minutes with swirling at 15 minutes. Ten ml of this rehydration was then added to the propagation. Propagation time was 8 hours at 33.3° C., at which time 15.2 ml of propagation was transferred to the fermentation vessels as an approximately 1.6% inoculation.

All propagations and fermentations were run in 1 L Sartorius Q+ bioreactors.

Simultaneous Saccharification and Fermentation (SSF)

Lactrol was added to each fermenter at a concentration of 0.024 grams per liter.

Urea was added to 600 ppm total urea. Glucoamylase SA was dosed to each reactor of mash at 110 μg EP GSA/gDS. To mimic enzyme addition at the plant scale, 55% of the glucoamylase and 50% of the fermentation urea were dosed at inoculation. After 8 hours of fermentation, the remaining 45% of glucoamylase and 50% of urea were added to the fermenter.

Temperature Profiles

All fermentations started at 32° C. and then started a temperature profile as described below.

TABLE 41

Temperature Profiles

| Ferm Time | Temp Target F. | Temp Target C. |
|---|---|---|
| 10 | 92 | 33.3 |
| 18 | 93 | 33.9 |
| 25 | 91 | 32.8 |
| 35 | 89 | 31.7 |
| 45 | 89 | 31.7 |
| 60 | 88 | 31.1 |

HPLC Analysis

Fermentation sampling took place by sampling 5 grams of mash into 15 ml tubes at 0, 2, 4, 6, 8, 12, 16, 24, 30, 48, 54, and 60 hours of fermentation. Each tube was processed for HPLC analysis by deactivation with 150 μL of 40% v/v $H_2SO_4$, vortexing, centrifuging at 1460×g for 10 minutes, and filtering through a 0.45 μm Whatman PP filter. Samples were stored at 4° C. prior to and during HPLC analysis.

TABLE 42

| | HPLC System |
|---|---|
| HPLC System | Agilent's 1100/1200 series with Chem station software Degasser, Quaternary Pump, Auto-Sampler, Column Compartment /w Heater Refractive Index Detector (RI) |
| Column | Bio-Rad HPX-87H Ion Exclusion Column 300 mm × 7.8 mm part# 125-0140 Bio-Rad guard cartridge Cation H part# 125-0129, Holder part# 125-0131 |
| Method | 0.005M H2SO4 mobile phase Flow rate: 0.6 ml/min Column temperature: 65° C. RI detector temperature: 55° C. |

Samples were analyzed for sugars (DP4+, DP3, DP2, glucose, and fructose), organic acids (lactic and acetic), glycerol, and ethanol.

Results

Lactic Acid titers are shown across the entire course of the fermentation in FIG. 1 below. Levels at the end of fermentation are shown in Table 26 below.

Table 43 shows lactic acid titers in 1 L fermentations, liquefied with Alpha-Amylase A.

TABLE 43

Lactic Acid Results at 60 Hours of Fermentation

| ER (g/L Lactic Acid) | MBG4851 (g/L Lactic Acid) | % Reduction with MBG4851 |
|---|---|---|
| 1.180 | 0.894 | 24.25% |

Example 28

Reduced Lactic Acid Accumulation During Bioreactor Fermentations of Industrially Produced Corn Mash.

The lactic acid accumulation when using MBG4851 compared to Ethanol Red™ were evaluated in industrially prepared corn mash liquefied with a blend of alpha-amylase (2.1 μg EP AA369/gDS), glucoamylase (4.5 μg EP PoAMG498/g DS) and 0.0385 μg EP Pfu/g DS.

Corn Mash

Industrially prepared corn mash was obtained from Husker AG. Solids on this mash were measured to be 34.05% by moisture balance.

Yeast Strains and Propagation

The two yeast strains tested in this experiment were Ethanol Red (Fermentis) and MBG4851.

The target solids percentage in the propagation was 20%, 587 ml of mash was added to 413 ml of water to reach a 1000 ml propagation volume at 20% solids. Lactrol was added at a concentration of 0.024 grams per liter. Urea nitrogen was added at a concentration of 1500 ppm, by adding 3 ml of a 50% urea solution. Glucoamylase dose was calculated to be 0.075 g per 1 L fermenter. As an inoculum, 2.08 grams of dried yeast were weighed out, added to 40 ml of water preheated to 36.5° C., and allowed to rehydrate for 30 minutes with swirling at 15 minutes. Ten ml of this rehydration was then added to the propagation. Propagation time was 8 hours at 33.3° C., at which time 15.2 ml of propagation was transferred to the fermentation vessels as an approximately 1.6% inoculation.

All propagations and fermentations were run in 1 L Sartorius Q+ bioreactors.

Simultaneous Saccharification and Fermentation (SSF)

Lactrol was added to each fermenter at a concentration of 0.024 grams per liter.

Urea was added to 600 ppm total urea. Glucoamylase SA was dosed to each reactor at 110 µg EP GSA/gDS. To mimic enzyme addition at the plant scale, 30% of the glucoamylase and 50% of the fermentation urea were dosed at inoculation. After 8 hours of fermentation, the remaining 70% of glucoamylase and 50% of urea were added to the fermenter.

Temperature Profiles

All fermentations started at 32° C. and then started a temperature profile as described below.

TABLE 44

Temperature Profiles

| Ferm Time | Temp Target F. | Temp Target C. |
|---|---|---|
| 10 | 92 | 33.3 |
| 18 | 93 | 33.9 |
| 25 | 91 | 32.8 |
| 35 | 89 | 31.7 |
| 45 | 89 | 31.7 |
| 60 | 88 | 31.1 |

HPLC Analysis

Fermentation sampling took place by sampling 5 grams of mash into 15 ml tubes at 0, 2, 4, 6, 8, 12, 16, 24, 30, 48, 54, and 60 hours of fermentation. Each tube was processed for HPLC analysis by deactivation with 150 µL of 40% v/v $H_2SO_4$, vortexing, centrifuging at 1460×g for 10 minutes, and filtering through a 0.45 µm Whatman PP filter. Samples were stored at 4° C. prior to and during HPLC analysis.

TABLE 45

HPLC System

| HPLC System | Agilent's 1100/1200 series with Chem station software Degasser, Quaternary Pump, Auto-Sampler, Column Compartment /w Heater Refractive Index Detector (RI) |
|---|---|
| Column | Bio-Rad HPX-87H Ion Exclusion Column 300 mm × 7.8 mm part# 125-0140 Bio-Rad guard cartridge Cation H part# 125-0129, Holder part# 125-0131 |

TABLE 45-continued

HPLC System

| Method | 0.005M $H_2SO_4$ mobile phase |
|---|---|
|  | Flow rate: 0.6 ml/min |
|  | Column temperature: 65° C. |
|  | RI detector temperature: 55° C. |

Samples were analyzed for sugars (DP4+, DP3, DP2, glucose, and fructose), organic acids (lactic and acetic), glycerol, and ethanol.

Results

Figure 2:
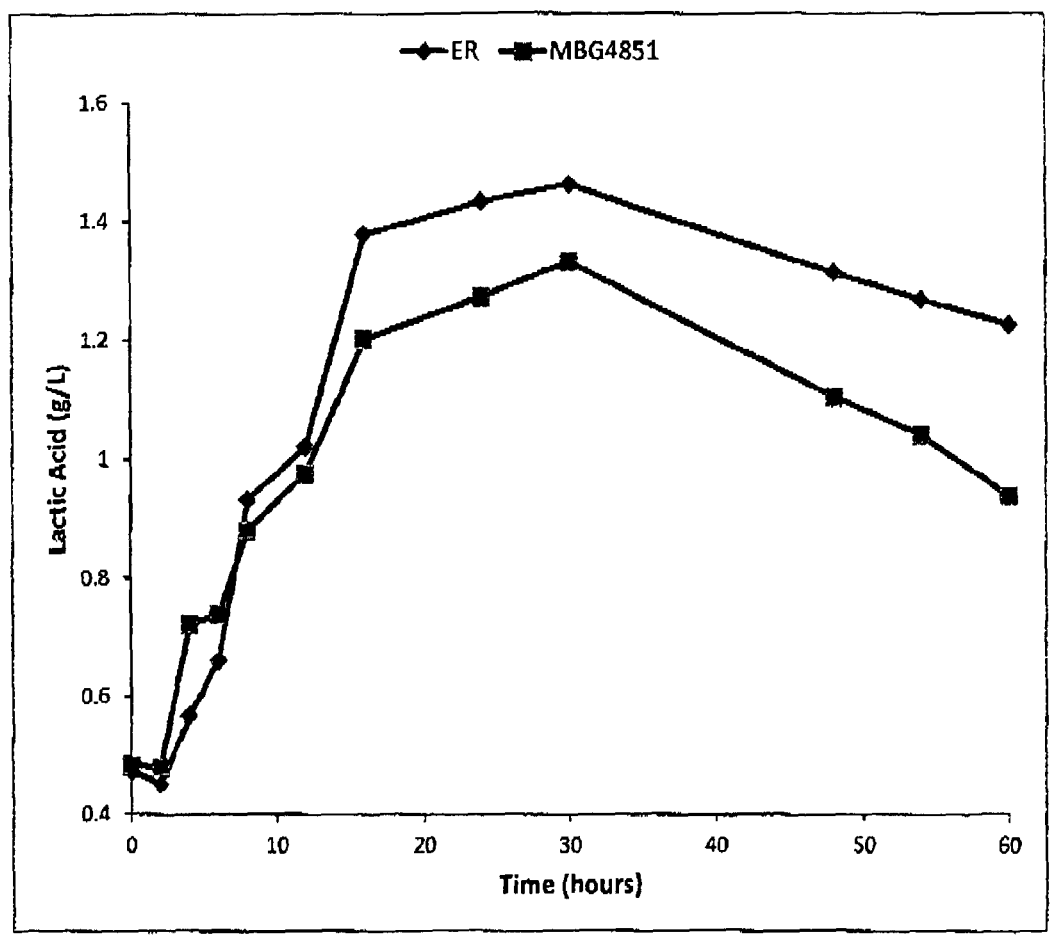
FIG. 2 shows the lactic acid levels during 1 L corn mash fermentations, liquefied with a blend of alpha-amylase (2.1 µg EP AA369/gDS), glucoamylase (4.5 µg EP PoAMG498/g DS) and 0.0385 µg EP Pfu/g DS.

Lactic Acid titers are shown across the entire course of the fermentation in FIG. 2 below. Levels at the end of fermentation are shown in Table 46 below.

Figure 3:
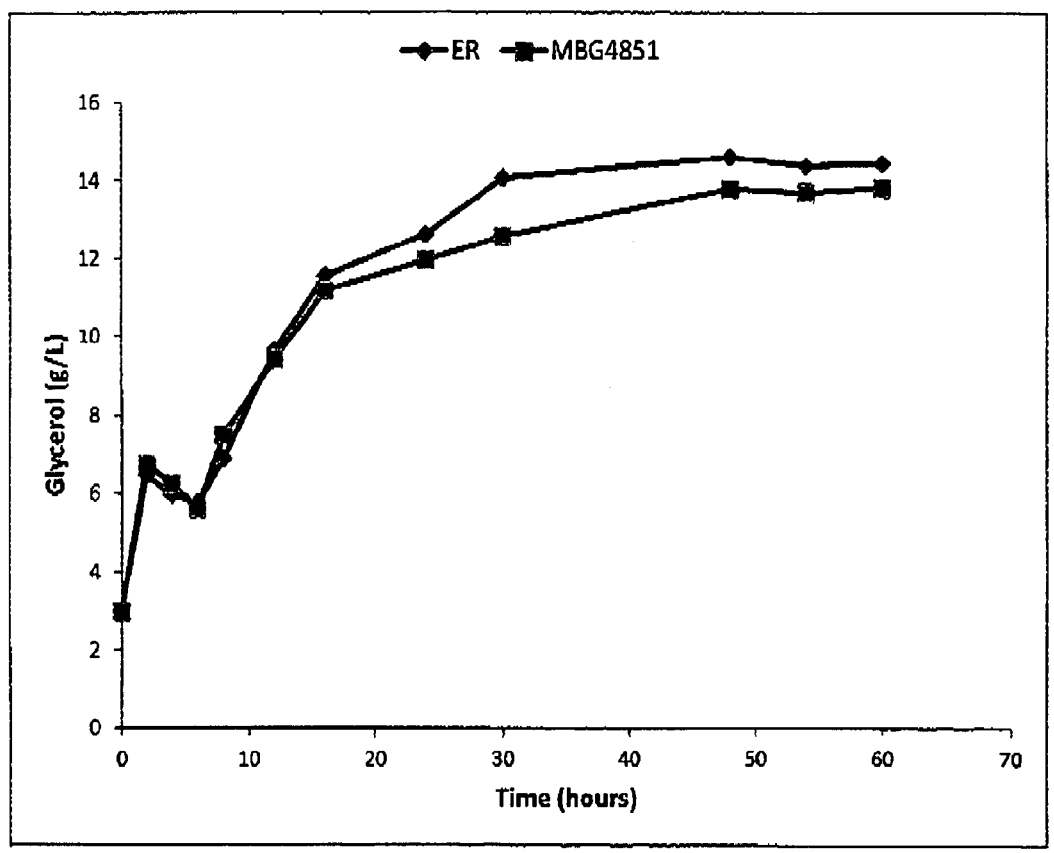
FIG. 3 shows the glycerol levels in fermentation comparing MBG4851 with Ethanol Red™ (ER) in an industrially prepared Alpha-Amylase A liquefied corn mash.

FIG. 3 shows the lactic acid levels during 1 L corn mash fermentations, liquefied with a blend of alpha-amylase (2.1 µg EP AA369/gDS), glucoamylase (4.5 µg EP PoAMG498/g DS) and 0.0385 µg EP Pfu/g DS.

TABLE 46

60 Hour Lactic Acid Results.

| ER (g/L Lactic Acid) | MBG4851 (g/L Lactic Acid) | % Reduction with MBG4851 |
|---|---|---|
| 1.226 | 0.938 | 23.54% |

Example 29

Glycerol Reduction in Fermentations of Mashes Produced with Varying Levels of Pfu Protease.

This example was carried out using the experimental set-up described in Example 22 above.

The glycerol levels when using MBG4851 compared to Ethanol Red™ were evaluated in liquefacts liquefied with a blend of alpha-amylase (2.1 µg EP AA369/gDS), glucoamylase (4.5 µg EP PoAMG498/g DS) and increasing levels of Pfu protease (0.0385, 1.5, and 3.0 µg EP Pfu/gDS).

Results

The 54 hour glycerol results are shown in Table 47 below for experiment 1 and Table 48 below for experiment 2. MBG4851 had a significant reduction of glycerol even at the highest levels of Pfu supplementation.

TABLE 47

54 hour Glycerol Results for Experiment 1

| Pfu Dose (µg EP/g Ds) | ER | MBG4851 | % Decrease |
|---|---|---|---|
| 0.0385 | 14.52546 | 12.3727325 | 14.82% |
| 1.5 | 13.57462 | 12.3477627 | 9.04% |
| 3 | 13.48923 | 12.3634329 | 8.35% |

TABLE 48

54 hour glycerol results for Experiment 2

| 0 ppm Urea | | | | 500 ppm Urea | | | |
|---|---|---|---|---|---|---|---|
| Pfu Dose (µg EP/g Ds) | ER | MBG4851 | % Decrease | Pfu Dose (µg EP/g Ds) | ER | MBG4851 | % Decrease |
| 0.0385 | 13.631 | 11.800 | 13.44% | 0.0385 | 13.665 | 11.346 | 16.97% |
| 1.5 | 13.425 | 11.565 | 13.85% | 1.5 | 13.543 | 11.503 | 15.06% |
| 3 | 12.921 | 11.362 | 12.06% | 3 | 12.902 | 11.657 | 9.65% |

Example 30

Glycerol Reduction in Fermentations of Backset Free Mashes Produced with Varying Levels of Pfu Protease This example was carried out using the experimental set-up described in Example 24 above.

The glycerol levels when using MBG4851 compared to Ethanol Red™ were evaluated in backset free liquefacts liquefied with a blend of alpha-amylase (2.1 µg EP AA369/gDS), glucoamylase (4.5 µg EP PoAMG498/g DS) and increasing levels of Pfu protease (0.0385 and 3.0 µg EP Pfu/gDS).

The 54 hour glycerol results are shown in Table 49 below. MBG4851 had a significant glycerol reduction compared to Ethanol Red regardless of added urea.

TABLE 49

54 hour glycerol results

| Pfu Dose | Urea (ppm) | ER | MBG4851 | % Decrease |
|---|---|---|---|---|
| 0.0385 µg EP/g DS Pfu | 0 | 9.033 | 7.748 | 14.23% |
| | 200 | 9.704 | 7.961 | 17.96% |
| | 300 | 10.145 | 8.103 | 20.13% |
| | 500 | 10.510 | 8.362 | 20.43% |
| | 1000 | 10.343 | 8.931 | 13.64% |
| 3.0 µg EP/g DS Pfu | 0 | 9.784 | 7.540 | 22.94% |
| | 200 | 9.621 | 7.683 | 20.14% |
| | 300 | 9.552 | 7.847 | 17.85% |
| | 500 | 9.545 | 7.787 | 18.42% |
| | 1000 | 9.660 | 7.983 | 17.35% |

Example 31

Glycerol Reduction in Fermentations of Corn Mash Produced Industrially with Alpha-Amylase A as the Liquefaction Enzyme This example was carried out using the experimental set-up described in Example 23 above.

The glycerol levels when using MBG4851 compared to Ethanol Red™ were evaluated in an industrially produced alpha-amylase (Alpha-Amylase A) liquefied corn mash with varying levels of urea supplementation.

Glycerol results can be found in Table 50 below.

TABLE 50

54 hour glycerol results

| Urea (ppm) | ER | MBG4851 | % Decrease |
|---|---|---|---|
| 0 | 11.721 | 10.007 | 14.62% |
| 150 | 12.182 | 10.162 | 16.58% |
| 300 | 12.115 | 10.289 | 15.07% |

TABLE 50-continued 54 hour glycerol results

| Urea (ppm) | ER | MBG4851 | % Decrease |
|---|---|---|---|
| 600 | 11.855 | 10.273 | 13.34% |
| 1000 | 11.714 | 10.524 | 10.16% |
| 3000 | 13.281 | 11.569 | 12.89% |

Example 32

Glycerol Reduction in Fermentations of Corn Mash Produced Industrially with Alpha-Amylase F (Fuelzyme™) as the Liquefaction Enzyme This example was carried out using the experimental set-up described in Example 25 above.

The glycerol levels when using of MBG4851 compared to Ethanol Red were evaluated in an industrially prepared Alpha-Amylase F (Fuelzyme™) liquefied corn mash.

52 hour glycerol results can be found in Table 51 below.

TABLE 51

52 hour glycerol results

| ER | MBG4851 | % Decrease |
|---|---|---|
| 10.974 | 8.518 | 22.37% |

Example 33

Glycerol Reduction in Fermentations of Corn Mash Produced Industrially with Liquefaction Enzyme Blend This example was carried out using the experimental set-up described in Example 26 above.

The glycerol levels when using MBG4851 compared to Ethanol Red were evaluated in industrially prepared corn mash liquefied with a blend of alpha-amylase (2.1 µg EP AA369/gDS), glucoamylase (4.5 µg EP PoAMG498/g DS) and 0.0385 µg EP Pfu/g DS.

54 hour glycerol results can be found in Tables 52 and 53 for Experiments 1 and 2 respectively.

TABLE 52

54 Hour Glycerol Results for Experiment 1

| Glucoamylase | ER | MBG4851 | % Decrease |
|---|---|---|---|
| GSA + CVD | 15.4833 | 13.6878 | 11.60% |
| GSA | 15.6964 | 13.9262 | 11.28% |

TABLE 53

54 Hour Glycerol Results for Experiment 2

| GA | ER | MBG4851 | % Decrease |
|---|---|---|---|
| GSA + CVD | 15.0683 | 13.3075 | 11.69% |
| GSA | 15.2362 | 13.4763 | 11.55% |

Example 34

Glycerol Level During Bioreactor Fermentations of Industrially Produced Alpha-Amylase A Corn Mash.

This example was carried out using the experimental set-up described in Example 27 above.

The glycerol levels when using of MBG4851 compared to Ethanol Red were evaluated in an industrially prepared Alpha-Amylase A liquefied corn mash.

Glycerol accumulation in the mash throughout fermentation can be seen in FIG. 3. 60 hour values can be found in Table 54.

FIG. 3 shows the glycerol levels during fermentation.

TABLE 54

60 hour Glycerol Values

| ER | MBG4851 | % Decrease |
|---|---|---|
| 14.429 | 13.799 | 4.37% |

Example 35

Glycerol Level During Bioreactor Fermentations of Industrially Produced Corn Mash.

This example was carried out using the experimental set-up described in Example 28 above.

The glycerol levels when using MBG4851 (V14/004037) compared to Ethanol Red were evaluated in industrially prepared corn mash liquefied with a blend of alpha-amylase (2.1 µg EP AA369/gDS), glucoamylase (4.5 µg EP PoAMG498/g DS) and 0.0385 µg EP Pfu/g DS.

Figure 4:
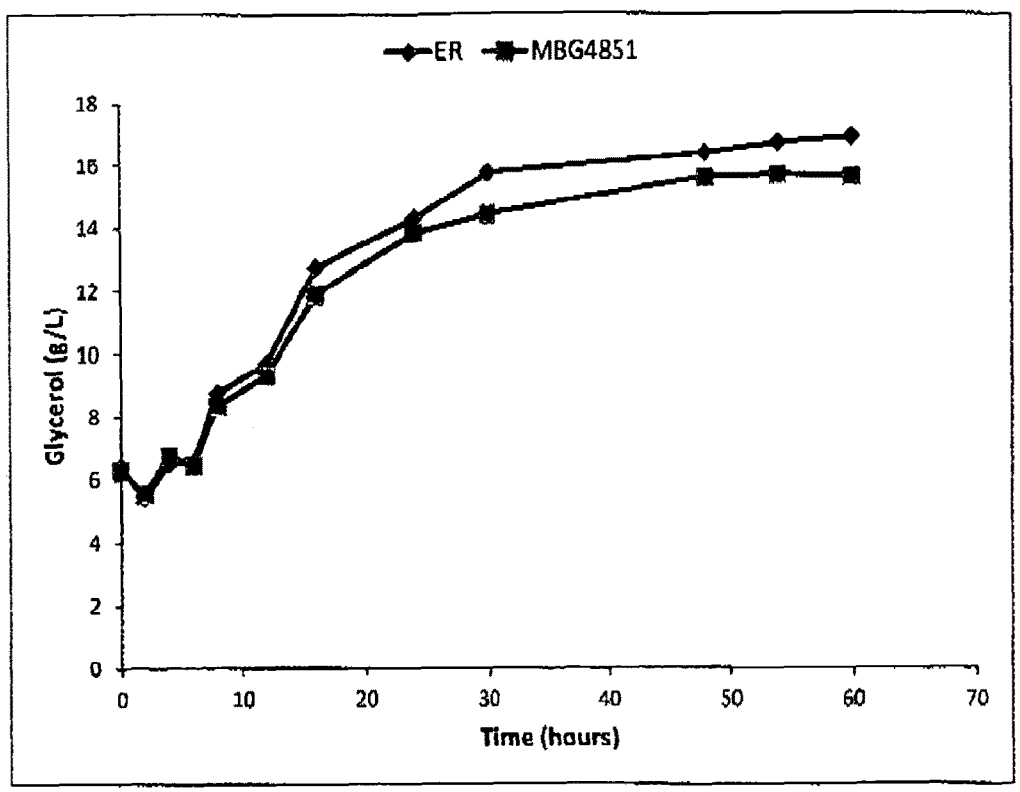
FIG. 4 shows the glycerol levels in fermentation comparing MBG4851 with Ethanol Red (ER) in industrially prepared corn mash liquefied with a blend of alpha-amylase (2.1 µg EP AA369/gDS), glucoamylase (4.5 µg EP PoAMG498/g DS) and 0.0385 µg EP Pfu/g DS.

Glycerol accumulation in the mash throughout fermentation can be seen in FIG. 4. 60 hour values can be found in Table 55.

FIG. 4 shows the glycerol levels during fermentation

TABLE 55

60 Hour Glycerol Values

| ER | MBG4851 | % Decrease |
|---|---|---|
| 16.916 | 15.643 | 7.53% |

Example 36

Production of Strain V14/004037 (MBG4851)

Strain V14/004037 was produced using the methods described in WO 2005/121337 and through matings with various strains of Saccharomyces cerevisiae combined with selection for characteristics including low glycerol and high ethanol production.

Strain V14/004037 was verified to be a Saccharomyces cerevisiae strain by its ability to sporulate and produce progeny when the germinated spores were mated with standard strains of Saccharomyces cerevisiae, including tester strains of Saccharomyces cerevisiae. One such haploid tester strain is W303-1A. Specifically, germinated spores of strain V14/004037 were able to produce hybrid progeny when mated with tester strain W303-1A.

In more detail, haploid strain W303-1A was obtained from the Yeast Genetic Stock Center at the ATCC, USA (ATCC #208352) Strain V14/004037 was cultured to form haploid Saccharomyces yeast as described in Ausubel, F. M. et al. (1997), Current Protocols in Molecular Biology, Volume 2, pages 13.2.1 to 13.2.5, published by John Wiley & Sons. Subsequently, the spores were germinated on a solid medium such as GYP containing 1% w/v D-glucose, 0.5% yeast extract, 1% w/v bacteriological peptone and 1.5% w/v agar and incubated at 30° C. for three to five days. The isolated germinated spores from strain V14/004037 were then mated together with haploid W303-1A using the method described in, for example, Ausubel, F. M. et al. (1997), Current Protocols in molecular Biology, Volume 2, pages 13.2.1 to 13.2.5, published by John Wiley & Sons. Formation of hybrid zygotes could be observed under a microscope demonstrating that strain V14/004037 is a Saccharomyces cerevisiae strain.

Strain V14/004037 was deposited on 17 Feb. 2014 at the National Measurement Institute, 1/153 Bertie Street, Port Melbourne, Victoria 3207, Australia under the Budapest Treaty and was designated accession number V14/004037.

Example 37

Growth of Strain V14/004037 (MBG4851) on Xylose Minimal Media

Growth of strain V14/004037 on xylose as a sole carbon source was determined using Test T1. Saccharomyces cerevisiae strain V14/004037 was streaked onto 2% w/v D-glucose 1% bacteriological peptone and 0.5% yeast extract medium (GYP) solidified with 2% agar using standard microbiological techniques. After incubation for 72 hours at 30 deg Celsius, yeast cells were taken from plates using a sterile microbiological loop and inoculated to an $OD_{600}$ (Optical Density at 600 nm) of between 0.1 and 0.2 units ($OD_{600}$ at T0) in 50 ml of broth. An $OD_{600}$ of 0.1 unit is equal to approximately $9 \times 10^5$ yeast cells/mL. The broth contained xylose (5% w/v), Difco Yeast Nitrogen Base w/o amino acids (0.67%), citric acid (0.3%) and trisodium citrate (0.7%) in distilled water in a 250 ml Erlenmeyer flask. Citric acid and trisodium citrate were provided as buffering agents that are not able to be used as growth substrates by Saccharomyces. D-(+)-Xylose 99% pure was obtained from Sigma-Aldrich (catalogue number X1500-500G). Cultures were incubated at 30 deg Celsius with shaking at 220 rpm (10 cm orbital diameter) for 48 hours prior to measuring $OD_{600}$ ($OD_{600}$ at $T_{48}$ hrs). The fold increase in biomass was determined by the equation: $OD_{600}$ at $T_{48}$ hrs divided by $OD_{600}$ at $T_0$.

Strain V14/004037 was inoculated at an initial $OD_{600}$ of 0.149 and increased more than 7-fold in 48 hours. Under the same conditions biomass of Ethanol Red yeast increased less than 2-fold.

Example 38

Fermentation of Corn Mash

Corn mash may be obtained from ethanol-producing companies such as described in Devantier et al., Applied Microbiology and Biotechnology 2005, 68:622-629. A method for preparing corn mash is also described in Thomas et al., Journal of Applied Microbiology 2001, 90:819-828.

Corn mash can also be prepared as follows:

Depending on the desired corn mash dry matter target, the following ingredients are placed into a glass beaker and the total weight of ingredients plus beaker is recorded.

TABLE 56

| CORN MASH % dry matter | UREA | STILLAGE BACKSET | WATER | GROUND CORN | α-AMYLASE |
|---|---|---|---|---|---|
| 30 | 0.6 g | 162 g | 231 g | 207 g | 1.34 ml |
| 31 | 0.6 g | 162 g | 224 g | 214 g | 1.34 ml |
| 32 | 0.6 g | 162 g | 217 g | 221 g | 1.34 ml |
| 33 | 0.6 g | 162 g | 210 g | 228 g | 1.34 ml |

Alpha-amylase may be for example, Liquozyme SC™ (Novozymes, Bagsvaerd, Denmark). The slurry is continuously stirred at 85° C. for 3.5 hours. The mash is then cooled, and the mass of beaker is weighed and compensated with water to account for evaporation during cooking of mash based on original weight of beaker and ingredients. Mash is cooled to 32° C. and adjusted to pH 5.2.

Glucoamylase is added. Glucoamylase may be for example Spirizyme Excel™ (Novozymes) and is dosed at 0.05% of dry corn solids. The mash is mixed, then dispensed in 15 g aliquots into 50 mL plastic screw capped tubes. The mash samples are placed in a static incubator at the desired temperature (typically 32° C.) for 30 min prior to addition of yeast. Yeast is prepared by suspending 0.1 g active dried yeast in 5 mL water at 37 deg C and leaving static for 30 min. After vortex mixing to disperse the yeast evenly, 190 microliters of the suspended yeast is inoculated per 15 g of corn mash prepared as described above.

The inoculated corn mash is incubated static for 50 hours and assayed by HPLC as described in WO 2011/035392.

The levels of ethanol, glycerol, glucose and maltose in the fermentation were determined using methods described in WO 2011/035392 following 20 hours (Table 57), 44 hrs (Table 58) and 50 hours (Table 59) of fermentation.

Figure 5:
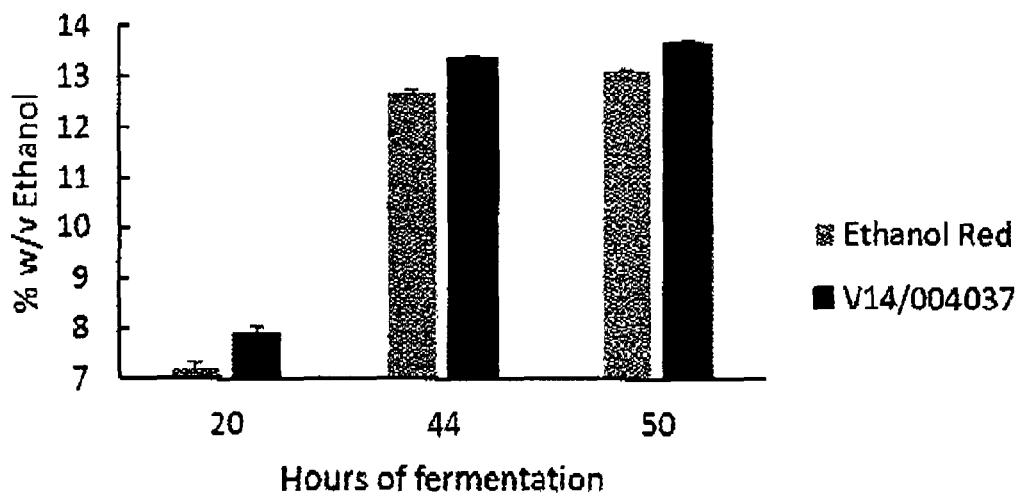
FIGS. 5 and 6 show a graph of ethanol production (top) and glucose consumption (bottom) by strains V14/004037 (black) and Ethanol Red™ (grey) following 20 hours, 44 hours and 50 hours of corn mash fermentation.
Figure 6:
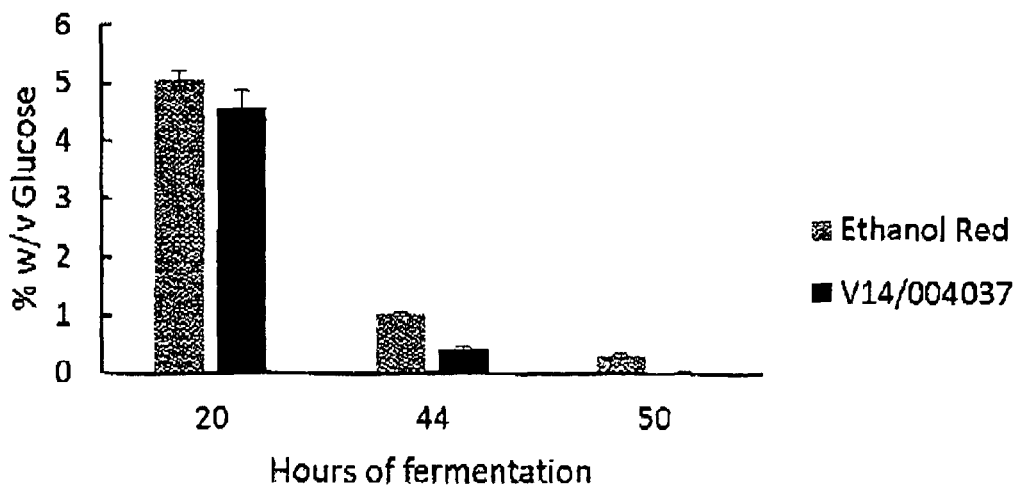

The results are also plotted graphically in FIGS. 5 and 6.

All yeasts were active dry yeasts. Ethanol Red is a commercial sample from Fermentis, BP 3029-137 rue Gabriel Peri, F-59703 Marcq-en-Baroeul, Cedex France.

V09/024011 and V14/004037 (MBG4851) were grown and dried as described in WO 2011/035392 A representative sample of Ethanol Red was deposited on 19 Mar. 2014 under the Budapest Treaty at the National Measurement Institute, 1/153 Bertie Street, Port Melbourne, Victoria 3207 and designated accession no. V14/007039. Values are presented as percent weight per volume (% w/v).

TABLE 57

Fermentation of corn mash for 20 hours

| 31% (DM) CORN MASH FERMENTATION 20 hr | Maltose | Glucose | Glycerol | Ethanol | Ethanol/ Glycerol Ratio |
|---|---|---|---|---|---|
| 1. Ethanol Red | 3.700 | 5.208 | 1.222 | 7.075 | 5.8 |
| 2. Ethanol Red | 3.602 | 5.144 | 1.218 | 7.282 | 6.0 |
| 3. Ethanol Red | 3.625 | 4.796 | 1.229 | 7.396 | 6.0 |
| 4. Ethanol Red | 3.597 | 5.025 | 1.222 | 7.186 | 5.9 |
| 5. Ethanol Red | 3.560 | 5.191 | 1.217 | 7.125 | 5.9 |
| 6. Ethanol Red | 3.633 | 5.104 | 1.221 | 7.271 | 6.0 |

TABLE 57-continued

Fermentation of corn mash for 20 hours

| 31% (DM) CORN MASH FERMENTATION 20 hr | Maltose | Glucose | Glycerol | Ethanol | Ethanol/ Glycerol Ratio |
|---|---|---|---|---|---|
| 7. V14/004037 | 3.304 | 4.522 | 1.146 | 7.726 | 6.7 |
| 8. V14/004037 | 2.610 | 5.173 | 1.165 | 8.049 | 6.9 |
| 9. V14/004037 | 3.222 | 4.451 | 1.158 | 7.880 | 6.8 |
| 10. V14/004037 | 3.234 | 4.409 | 1.156 | 7.924 | 6.9 |
| 11. V14/004037 | 3.250 | 4.559 | 1.151 | 7.853 | 6.8 |
| 12. V14/004037 | 3.195 | 4.326 | 1.161 | 7.991 | 6.9 |
| 13. V09/024011 | 4.276 | 9.725 | 1.022 | 4.667 | 4.6 |
| 14. V09/024011 | 4.205 | 9.542 | 1.039 | 4.858 | 4.7 |
| 15. V09/024011 | 4.183 | 9.714 | 1.031 | 4.771 | 4.6 |
| 16. V09/024011 | 2.445 | 11.748 | 1.052 | 4.958 | 4.7 |
| 17. V09/024011 | 4.217 | 9.802 | 1.023 | 4.750 | 4.6 |
| 18. V09/024011 | 4.179 | 9.551 | 1.030 | 4.817 | 4.7 |

As can be seen from Table 57, after 20 hours of fermentation of corn mash, strain V14/004037 produced greater amounts of ethanol than Ethanol Red and strain V09/024011 and less glycerol than Ethanol Red. The ratio of the fermentation products Ethanol to Glycerol was also significantly higher for V14/004037.

TABLE 58

Fermentation of corn mash for 44 hours

| 31% (DM) CORN MASH FERMENTATION 44 hr | Maltose | Glucose | Glycerol | Ethanol | Ethanol/ Glycerol Ratio |
|---|---|---|---|---|---|
| 1. Ethanol Red | 0.447 | 1.033 | 1.588 | 12.687 | 8.0 |
| 2. Ethanol Red | 0.465 | 1.005 | 1.577 | 12.704 | 8.1 |
| 3. Ethanol Red | 0.452 | 0.998 | 1.594 | 12.745 | 8.0 |
| 4. Ethanol Red | 0.446 | 1.017 | 1.577 | 12.679 | 8.0 |
| 5. Ethanol Red | 0.438 | 1.061 | 1.562 | 12.623 | 8.1 |
| 6. Ethanol Red | 0.447 | 1.047 | 1.574 | 12.685 | 8.1 |
| 7. V14/004037 | 0.322 | 0.401 | 1.361 | 13.379 | 9.8 |
| 8. V14/004037 | 0.324 | 0.402 | 1.350 | 13.377 | 9.9 |
| 9. V14/004037 | 0.324 | 0.481 | 1.354 | 13.361 | 9.9 |
| 10. V14/004037 | 0.324 | 0.355 | 1.355 | 13.429 | 9.9 |
| 11. V14/004037 | 0.329 | 0.449 | 1.348 | 13.313 | 9.9 |
| 12. V14/004037 | 0.321 | 0.346 | 1.354 | 13.424 | 9.9 |
| 13. V09/024011 | 0.468 | 2.647 | 1.640 | 11.578 | 7.1 |
| 14. V09/024011 | 0.466 | 2.617 | 1.636 | 11.637 | 7.1 |
| 15. V09/024011 | 0.469 | 2.556 | 1.644 | 11.733 | 7.1 |
| 16. V09/024011 | 0.461 | 2.456 | 1.633 | 11.677 | 7.2 |
| 17. V09/024011 | 0.472 | 2.648 | 1.643 | 11.613 | 7.1 |
| 18. V09/024011 | 0.464 | 2.573 | 1.639 | 11.664 | 7.1 |

As can be seen from Table 58, after 44 hours of fermentation of corn mash, strain V14/004037 produced greater amounts of ethanol than Ethanol Red and strain V09/024011, and less glycerol than both Ethanol Red and strain V09/024011.

TABLE 59

Fermentation of corn mash for 50 hours

| 31% (DM) CORN MASH FERMENTATION 50 hr | Maltose | Glucose | Glycerol | Ethanol | Ethanol/ Glycerol Ratio |
|---|---|---|---|---|---|
| 1. Ethanol Red | 0.456 | 0.290 | 1.597 | 13.116 | 8.2 |
| 2. Ethanol Red | 0.457 | 0.363 | 1.593 | 13.108 | 8.2 |
| 3. Ethanol Red | 0.467 | 0.260 | 1.607 | 13.145 | 8.2 |
| 4. Ethanol Red | 0.472 | 0.295 | 1.598 | 13.135 | 8.2 |
| 5. Ethanol Red | 0.450 | 0.298 | 1.595 | 13.133 | 8.2 |

TABLE 59-continued

Fermentation of corn mash for 50 hours

| 31% (DM) CORN MASH FERMENTATION 50 hr | Maltose | Glucose | Glycerol | Ethanol | Ethanol/ Glycerol Ratio |
|---|---|---|---|---|---|
| 6. Ethanol Red | 0.459 | 0.323 | 1.600 | 13.158 | 8.2 |
| 7. V14/004037 | 0.302 | 0.022 | 1.359 | 13.736 | 10.1 |
| 8. V14/004037 | 0.308 | 0.017 | 1.359 | 13.554 | 10.0 |
| 9. V14/004037 | 0.305 | 0.029 | 1.366 | 13.640 | 10.0 |
| 10. V14/004037 | 0.304 | 0.023 | 1.361 | 13.648 | 10.0 |
| 11. V14/004037 | 0.308 | 0.030 | 1.357 | 13.616 | 10.0 |
| 12. V14/004037 | 0.303 | 0.022 | 1.366 | 13.651 | 10.0 |
| 13. V09/024011 | 0.456 | 1.596 | 1.671 | 12.334 | 7.4 |
| 14. V09/024011 | 0.458 | 1.469 | 1.681 | 12.339 | 7.3 |
| 15. V09/024011 | 0.459 | 1.395 | 1.683 | 12.472 | 7.4 |
| 16. V09/024011 | 0.455 | 1.280 | 1.674 | 12.451 | 7.4 |
| 17. V09/024011 | 0.461 | 1.389 | 1.678 | 12.460 | 7.4 |
| 18. V09/024011 | 0.453 | 1.367 | 1.679 | 12.453 | 7.4 |

FIGS. 5 and 6 show that the rate of ethanol production by strain V14/004037 is significantly greater than both Ethanol Red and strain V09/024011 at 20 hours, indicating that strain V14/004037 is more efficient at ethanol production. This may be advantageous in reducing the time necessary for fermentation. In addition the final ratio of Ethanol to Glycerol is higher for strain V14/004037. Furthermore even conversion of the residual glucose to ethanol at maximum theoretical levels (0.51 g ethanol/g glucose) indicates the ethanol yield of strain V14/004037 is better than Ethanol Red or V09/024011.

Example 39

Reduced Acetaldehyde Accumulation in Mash Produced with Pfu Protease.

The performance of MBG4851 compared to Ethanol Red™ (ER) was evaluated in a liquefact liquefied with a blend of alpha-amylase (2.1 µg EP AA369/gDS), glucoamylase (4.5 µg EP PoAMG498/g DS) and Pfu protease (3.0 µg EP Pfu/gDS).

Liquefaction

Liquefactions were prepared by combining ground corn, backset and tap water to a target total weight of 185 g at 32.50% Dry Solids (DS); backset was blended at 30% w/w (weight of backset per total weight of mash). Backset from Lincolnway Energy, received on Dec. 12, 2012, and corn ground in house received from GPRE in Central City, Nebr., USA, were used for all liquefactions. Initial slurry pH was 5.0 and therefore, no further adjustment was needed. Next, water and enzymes were added, followed by sealing of all Labomat canisters and starting the 200 ml program: 5° C./min. Ramp, 15 minute Ramp to 80° C., hold for 1 min, Ramp to 85° C. at 1° C./min and holding for 103 min., 40 rpm for 30 seconds to the left and 30 seconds to the right. All canisters of mash were cooled in an ice bath and prepared for fermentation according to the SSF procedure described below. 2.1 µg EP AA369/gDS, 4.5 µg EP PoAMG498/gDS, and 3.0 µg EP Pfu/g DS were added.

Yeast Strains and Preparation

The two yeast strains tested in this experiment were Ethanol Red™ (Fermentis) and MBG4851. Yeasts were rehydrated by weighing 3.52 g of dried yeast into 40 ml of 37° C. tap water in a 125 mL Erlenmeyer flask. The flasks were then covered with parafilm, swirled to mix, and allowed to incubate in a 32° C. water bath. After 15 minutes, the flasks were removed from the water bath and swirled once more to mix.

Simultaneous Saccharification and Fermentation (SSF)

The pH after liquefaction was 5.1 and was not adjusted further for SSF. Mash solids were calculated to be 31.6% by moisture balance.

One 350 ml propagation was set up for each yeast in 500 ml kettles. Mash solids were adjusted to ~27%, and 0.024 g/L Lactrol was added for bacterial control. GA dose was calculated to be 0.018 g per 350 ml propagation. Five ml of rehydrated yeast was then added to start the propagation. Propagation time was 8 hours at 33.3° C., at which time 18 ml of propagation was transferred to the fermentation vessels as an approximately 1.8% inoculation.

Fermentations were set up in 1 L Sartorius Q+ reactors. Each fermentation vessel was set up with 1000 ml of the aforementioned corn mash. Mash was held at 12° C. until approximately one hour before inoculation, at which time it was warmed to 32° C. Lactrol was added to each fermenter at 0.024 g/L to limit bacterial contamination.

Urea was added to each mash to a final concentration of 200 ppm. Glucoamylase SA was dosed to each reactor of mash at 110 µg EP GSA/gDS. To mimic enzyme addition at the plant scale, 30% of the glucoamylase was dosed at inoculation. After 8 hours of fermentation, the remaining 70% of glucoamylase was added to the fermenter. The temperature of both bioreactors started at 32° C. and then followed the following profile to mimic the temperatures experienced in an industrial setting.

| Ferm Time | Temp Target F. | Temp Target C. |
|---|---|---|
| 10 | 92 | 33.3 |
| 18 | 93 | 33.9 |
| 25 | 91 | 32.8 |
| 35 | 89 | 31.7 |
| 45 | 89 | 31.7 |
| 60 | 88 | 31.1 |

Sampling and GC Analysis

Fermentation sampling took place after 54 hours of fermentation.

Reactors were not sampled during fermentation. At the final time point, three samples were taken from each reactor. 5 ml of mash was sampled into a 15 ml centrifuge tube. After sampling, 150 µl of 40% $H_2SO_4$ was used to stop the fermentation. Samples were vortexed to mix and then centrifuged at 3000 rpm for 5-10 minutes to pellet corn debris. Supernatant was then filtered through 0.45 µM filters. All 54 hour samples were processed without further dilution. Samples were stored at 4° C. prior to submission for analysis.

Acetaldehyde levels were analyzed by Enthalpy Analytical Inc. (Durham, N.C.)

Results

The results for the acetaldehyde levels are shown below. In this experiment, the MBG4851 fermentation showed a 52% reduction in acetaldehyde levels compared to Ethanol Red™ (ER).

| | Acetaldehyde µg/ml |
|---|---|
| ER | 51.36667 |
| MBG4851 | 24.56667 |

Example 40

Increased Oil Yield in Fermentations Performed with MBG4851.

Yeast Strains and Preparation

The two yeast strains tested in this experiment were Ethanol Red™ (Fermentis) and MBG4851. Yeasts were rehydrated by weighing 5.5 g of dried yeast into 100 ml of 37° C. tap water in a 250 mL Erlenmeyer flask. The flasks were then covered with parafilm, swirled to mix, and allowed to incubate in a 32° C. water bath. After 15 minutes, the flasks were removed from the water bath and swirled once more to mix.

Simultaneous Saccharification and Fermentation (SSF)

Industrially produced corn mash liquefied with a blend of alpha-amylase (2.1 μg EP AA369/gDS), glucoamylase (4.5 μg EP PoAMG498/g DS) and protease (0.0385 μg EP Pfu/g DS) was utilized for this experiment. The pH after liquefaction was 5.1 and was not adjusted further for SSF. Mash solids were calculated to be 28.30% by moisture balance. Mash was adjusted to 1000 ppm urea and 3 mg/L penicillin and aliquoted into 25 g samples in 50 mL screw cap centrifuge tubes, with 24 samples total. Glucoamylase SA ("GSA") was dosed at 0.6 AGU/gDS in all tubes. In tubes 4-6 and 10-12, Protease X was dosed at 5 μg/gDS. In tubes 1-6, 150 μL of rehydrated MBG4851 yeast was added. In tubes 7-12, 150 μL of rehydrated Ethanol Red yeast was added. Fermentations proceeded in a 32° C. shaking water bath for 64 hours.

Sampling and Oil Analysis

Oil Extraction:

Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to a pre-weighed 5 mL flip-top tube, and reweighed. The density of the sample was measured using a Rudolph Research Analytical density meter. The density of the supernatant was then calculated using the standard curve equation to find the % oil in the supernatant. From this value the total % oil in the starting material was derived.

Results

The results of the oil assays are listed in the following table.

| Treatment | Average % Oil | +/− | % Change Over Control |
|---|---|---|---|
| ER Yeast | 0.460% | 0.058% | — |
| ER Yeast + Protease X | 0.552% | 0.058% | 20.02% |
| MBG4851 Yeast | 0.549% | 0.058% | 19.32% |
| MBG4851 Yeast + Protease X | 0.673% | 0.058% | 46.15% |

The invention is further described in the following numbered paragraphs:

1. A process for producing ethanol from starch-containing material comprising the steps of:
   i) liquefying the starch-containing material at a temperature above the initial gelatinization temperature using an alpha-amylase;
   ii) saccharifying using a glucoamylase;
   iii) fermenting using a fermenting organism;
   wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851, or a derivative of *Saccharomyces* strain V14/004037 having defining characteristics of strain V14/004037.

2. The process of paragraph 1, wherein a nitrogen source, preferably urea, is added in saccharification, fermentation, or simultaneous saccharification and fermentation (SSF).

3. The process of paragraph 1, wherein less than 3,000 ppm, such as less than 2000 ppm, such as less than 1,000 ppm, such as less than 800 ppm, such as less than 600 ppm, such as less than 500 ppm, such as less than 400 ppm, such as less than 300 ppm such as less than 200 ppm, such as less than 100 ppm nitrogen source, such a no nitrogen source, especially urea, is added in saccharification or fermentation or SSF.

4. The process of paragraph 1, wherein from 100 to 600 ppm urea is adding in saccharification or fermentation or SSF.

5. The process of any of paragraphs 1-4, wherein a protease is added in saccharification or fermentation or SSF.

6. The process of any of paragraphs 1-5, further comprises, prior to the liquefaction step i), the steps of:
   x) reducing the particle size of the starch-containing material, preferably by dry milling;
   y) forming a slurry comprising the starch-containing material and water.

7. The process of any of paragraphs 1-6, wherein at least 50%, preferably at least 70%, more preferably at least 80%, especially at least 90% of the starch-containing material fit through a sieve with #6 screen.

8. The process of any of paragraphs 1-3, wherein the pH in liquefaction is between 4-7, such as between pH 4.5-6.5, such as between pH 5.0-6.5, such as between pH 5.0-6.0, such as between pH 5.2-6.2, such as around 5.2, such as around 5.4, such as around 5.6, such as around 5.8.

9. The process of any of paragraphs 1-8, wherein the temperature in liquefaction is in the range from 70-100° C., such as between 75-95° C., such as between 75-90° C., preferably between 80-90° C., such as 82-88° C., such as around 85° C.

10. The process of any of paragraphs 1-9, wherein a jet-cooking step is carried out prior to liquefaction in step i).

11. The process of paragraph 10, wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.

12. The process of any of paragraphs 1-11, wherein saccharification and fermentation is carried out sequentially or simultaneously (SSF).

13. The process of any of paragraphs 1-12, wherein saccharification is carried out at a temperature from 20-75° C., preferably from 40-70° C., such as around 60° C., and at a pH between 4 and 5.

14. The process of any of paragraphs 1-13, wherein fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

15. The process of any of paragraphs 1-14, wherein the fermentation product is recovered after fermentation, such as by distillation.

16. The process of any of paragraphs 1-15, wherein the fermentation product is an alcohol, preferably ethanol, especially fuel ethanol, potable ethanol and/or industrial ethanol.

17. The process of any of paragraphs 1-16, wherein the starch-containing starting material is whole grains.

18. The process of any of paragraphs 1-17, wherein the starch-containing material is derived from corn, wheat, barley, rye, milo, sago, cassava, manioc, tapioca, sorghum, oats, rice or potatoes.

19. The process of any of paragraphs 1-18, wherein the alpha-amylase used or added in liquefaction step i) is of bacterial origin.

20. The process of any of paragraphs 1-19, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

21. The process of paragraph 20, wherein the *Bacillus stearothermophilus* alpha-amylase or variant thereof is truncated, preferably to have from 485-495 amini acuds, such as around 491 amino acids.

22. The process of any of paragraphs 20 or 21, wherein the *Bacillus stearothermophilus* alpha-amylase has a double deletion at positions I181+G182, and optionally a N193F substitution, or deletion of R179+G180 (using SEQ ID NO: 1 for numbering).

23. The process of any of paragraphs 20-22, wherein the *Bacillus stearothermophilus* alpha-amylase has a substitution in position S242, preferably S242Q substitution (using SEQ ID NO: 1 for numbering).

24. The process of any of paragraphs 20-23, wherein the *Bacillus stearothermophilus* alpha-amylase has a substitution in position E188, preferably E188P substitution (using SEQ ID NO: 1 for numbering).

25. The process of any of paragraphs 1-24, wherein the alpha-amylase has a T½ (min) at pH 4.5, 85° C., 0.12 mM CaCl$_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

26. The process of any of paragraphs 1-25, wherein the alpha-amylase present and/or added in liquefaction step i) is selected from the group of *Bacillus stearothermophilus* alpha-amylase variants with the following mutations in addition to I181*+G182*, and optionally N193F:
  V59A+Q89R+G112D+E129V+K177L+R179E+K220P+ N224L+Q254S;
  V59A+Q89R+E129V+K177L+R179E+H208Y+K220P+ N224L+Q254S;
  V59A+Q89R+E129V+K177L+R179E+K220P+N224L+ Q254S+D269E+D281N;
  V59A+Q89R+E129V+K177L+R179E+K220P+N224L+ Q254S+I270L;
  V59A+Q89R+E129V+K177L+R179E+K220P+N224L+ Q254S+H274K;
  V59A+Q89R+E129V+K177L+R179E+K220P+N224L+ Q254S+Y276F;
  V59A+E129V+R157Y+K177L+R179E+K220P+ N224L+S242Q+Q254S;
  V59A+E129V+K177L+R179E+H208Y+K220P+ N224L+S242Q+Q254S;
  59A+E129V+K177L+R179E+K220P+N224L+S242Q+ Q254S;
  V59A+E129V+K177L+R179E+K220P+N224L+ S242Q+Q254S+H274K;
  V59A+E129V+K177L+R179E+K220P+N224L+ S242Q+Q254S+Y276F;
  V59A+E129V+K177L+R179E+K220P+N224L+ S242Q+Q254S+D281N;
  V59A+E129V+K177L+R179E+K220P+N224L+ S242Q+Q254S+M284T;
  V59A+E129V+K177L+R179E+K220P+N224L+ S242Q+Q254S+G416V;
  V59A+E129V+K177L+R179E+K220P+N224L+Q254S;
  V59A+E129V+K177L+R179E+K220P+N224L+ Q254S+M284T;
  A91L+M96I+E129V+K177L+R179E+K220P+N224L+ S242Q+Q254S;
  E129V+K177L+R179E;
  E129V+K177L+R179E+K220P+N224L+S242Q+ Q254S;
  E129V+K177L+R179E+K220P+N224L+S242Q+ Q254S+Y276F+L427M;
  E129V+K177L+R179E+K220P+N224L+S242Q+ Q254S+M284T;
  E129V+K177L+R179E+K220P+N224L+S242Q+ Q254S+N376*+1377*;
  E129V+K177L+R179E+K220P+N224L+Q254S;
  E129V+K177L+R179E+K220P+N224L+Q254S+ M284T;
  E129V+K177L+R179E+S242Q;
  E129V+K177L+R179V+K220P+N224L+S242Q+ Q254S;
  K220P+N224L+S242Q+Q254S;
  M284V;
  V59A+Q89R+E129V+K177L+R179E+Q254S+M284V.
  V59A+E129V+K177L+R179E+Q254S+M284V;

27. The process of any of paragraphs 1-26, wherein the alpha-amylase present and/or added in liquefaction step i) is selected from the following group of *Bacillus stearothermophilus* alpha-amylase variants:
  I181*+G182*+N193F+E129V+K177L+R179E;
  I181*+G182*+N193F+V59A+Q89R+E129V+K177L+ R179E+H208Y+K220P+N224L+Q254S
  I181*+G182*+N193F+V59A+Q89R+E129V+K177L+ R179E+Q254S+M284V;
  I181*+G182*+N193F+V59A+E129V+K177L+R179E+ Q254S+M284V and
  I181*+G182*+N193F+E129V+K177L+R179E+K220P+ N224L+S242Q+Q254S (using SEQ ID NO: 1 herein for numbering).

28. The process of any of paragraphs 1-27, wherein a glucoamylase is present and/or added in saccharification and/or fermentation.

29. The process of paragraph 28, wherein the glucoamylase present and/or added in saccharification, fermentation or simultaneous saccharification and fermentation (SSF) is of fungal origin, preferably from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*, such as *G. serpiarium* or *G. trabeum*, or a strain of the *Nigrofomes*.

30. The process of any of paragraphs 1-29, wherein the glucoamylase is derived from *Talaromyces emersonii*, such as the one shown in SEQ ID NO: 19 herein, 31. The process of any of paragraphs 1-29, wherein the glucoamylase is selected from the group consisting of:
(i) a glucoamylase comprising the mature polypeptide of SEQ ID NO: 19 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

32. The process of any of paragraphs 1-29, wherein the glucoamylase present and/or added in saccharification is derived from *Gloeophyllum* serpiarium, such as the one shown in SEQ ID NO: 15 herein.

33. The process of any of paragraphs 1-29, wherein the glucoamylase present and/or added in saccharification is selected from the group consisting of:
(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

34. The process of any of paragraphs 1-29, wherein the glucoamylase present and/or added in saccharification is derived from *Gloeophyllum* trabeum such as the one shown in SEQ ID NO: 17 herein.

35. The process of any of paragraphs 1-29, wherein the glucoamylase present and/or added in saccharification is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

36. The process of any of paragraphs 1-29, wherein the glucoamylase is present and/or added in saccharification and/or fermentation in combination with an alpha-amylase.

37. The process of paragraph 36, wherein the alpha-amylase is present and/or added in saccharification and/or fermentation is of fungal or bacterial origin.

38. The process of paragraph 36 or 37, wherein the alpha-amylase present and/or added in saccharification and/or fermentation is derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 16 herein.

39. The process of any of paragraphs 36-38, wherein the alpha-amylase present and/or added in saccharification and/or fermentation is selected from the group consisting of:
(i) an alpha-amylase comprising the mature polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

40. The process of any of paragraphs 36-39, wherein the alpha-amylase is a variant of the alpha-amylase shown in SEQ ID NO: 16 having at least one of the following substitutions or combinations of substitutions: D165M; Y141W; Y141R; K136F; K192R; P224A; P224R; S123H+ Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).

41. The process of any of paragraphs 36-40, wherein the alpha-amylase is derived from a *Rhizomucor pusillus* with an *Aspergillus niger* glucoamylase linker and starch-binding domain (SBD), preferably disclosed as SEQ ID NO: 16 herein, preferably having one or more of the following substitutions: G128D, D143N, preferably G128D+D143N (using SEQ ID NO: 16 for numering).

42. The process of any of paragraphs 36-41, wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 16 herein.

43. The process of any of paragraphs 1-42, wherein liquefaction step i) is carried out using:
an alpha-amylase;
a protease having a thermostability value of more than 20% determined as Relative Activity at 80° C./70° C.; and
optionally a glucoamylase.

44. The process of 43, wherein the protease with a thermostability value of more than 25% determined as Relative Activity at 80° C./70° C.

45. The process of paragraphs 43-44, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

46. The process of any of paragraphs 43-45, wherein the protease has a thermostability of between 20 and 50%, such as between 20 and 40%, such as 20 and 30% determined as Relative Activity at 80° C./70° C.

47. The process of any of paragraphs 43-46, wherein the protease has a thermostability between 50 and 115%, such as between 50 and 70%, such as between 50 and 60%, such as between 100 and 120%, such as between 105 and 115% determined as Relative Activity at 80° C./70° C.

48. The process of any of paragraphs 43-47, wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

49. The process of any of paragraphs 43-48, wherein the protease has thermostability of between 10 and 50%, such as between 10 and 30%, such as between 10 and 25% determined as Relative Activity at 85° C./70° C.

50. The process of any of paragraphs 43-49, wherein the protease has a themostability above 60%, such as above 90%, such as above 100%, such as above 110% at 85° C. as determined using the Zein-BCA assay.

51. The process of any of paragraphs 43-50, wherein the protease has a themostability between 60-120, such as between 70-120%, such as between 80-120%, such as between 90-120%, such as between 100-120%, such as 110-120% at 85° C. as determined using the Zein-BCA assay.

52. The process of any of paragraphs 43-51, wherein the protease is of fungal origin.

53. The process of any of paragraphs 43-52, wherein the protease is a variant of the metallo protease derived from a strain of the genus *Thermoascus*, preferably a strain of *Thermoascus aurantiacus*, especially *Thermoascus aurantiacus* CGMCC No. 0670.

54. The process of any of paragraphs 43-53, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein mutations selected from the group of:
S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L; and
D79L+S87P+D142L.

55. The process of any of paragraphs 43-54, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein with the following mutations:
D79L+S87P+A112P+D142L:
D79L+S87P+D142L; or
A27K+D79L+Y82F+S87G+D104P+A112P+A126V+D142L.

56. The process of any of paragraphs 43-55, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

57. The process of any of paragraphs 43-56, wherein the protease variant of the *Thermoascus aurantiacus* protease shown in SEQ ID NO: 3 herein is one of the following:
D79L S87P D142L
D79L S87P A112P D142L
D79L Y82F S87P A112P D142L
S38T D79L S87P A112P A126V D142L
D79L Y82F S87P A112P A126V D142L
A27K D79L S87P A112P A126V D142L
S49P D79L S87P A112P D142L
S50P D79L S87P A112P D142L
D79L S87P D104P A112P D142L
D79L Y82F S87G A112P D142L
570V D79L Y82F S87G Y97W A112P D142L
D79L Y82F S87G Y97W D104P A112P D142L
570V D79L Y82F S87G A112P D142L
D79L Y82F S87G D104P A112P D142L
D79L Y82F S87G A112P A126V D142L
Y82F S87G S70V D79L D104P A112P D142L
Y82F S87G D79L D104P A112P A126V D142L
A27K D79L Y82F S87G D104P A112P A126V D142L 58. The process of any of paragraphs 43-57, wherein the protease is of bacterial origin.

59. The process of any of paragraphs 43-58, wherein the protease is derived from a strain of *Pyrococcus*, preferably a strain of *Pyrococcus furiosus*.

60. The process of any of paragraphs 1-41, wherein the protease is the one shown in SEQ ID NO: 1 in U.S. Pat. No. 6,358,726, or SEQ ID NO: 13 herein.

61. The process of any of paragraphs 43-60, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 13 herein.

62. The process of any of paragraph 43-61, wherein 0.5-100 micro gram *Pyrococcus furiosus* protease per gram DS, such as 1-50 micro gram *Pyrococcus furiosus* protease per gram DS, such as 1-10 micro gram *Pyrococcus furiosus* protease per gram DS, such as 1.5-5 micro gram *Pyrococcus furiosus* protease per gram DS, such as around or more than 1.5 micro gram *Pyrococcus furiosus* protease per gram DS are present and/or added in liquefaction step i).

63. The process of any of paragraphs 43-62, wherein 2-100 micro gram *Pyrococcus furiosus* protease per gram DS, such as 2.5-50 micro gram *Pyrococcus furiosus* protease per gram DS, such as 2.5-10 micro gram *Pyrococcus furiosus* protease per gram DS, such as 2.5-5 micro gram *Pyrococcus furiosus* protease gram DS, especially around 3 micro gram *Pyrococcus furiosus* protease per gram DS are present and/or added in liquefaction step i).

64. The process of any of paragraphs 43-63, wherein a glucoamylase is present and/or added during liquefaction step i).

65. The process of any of paragraphs 43-64, wherein the glucoamylase present and/or added in liquefaction has a heat stability at 85° C., pH 5.3, of at least 20%, such as at least 30%, preferably at least 35%.

66. The process of any of paragraphs 43-65, wherein the glucoamylase present and/or added in liquefaction has a relative activity pH optimum at pH 5.0 of at least 90%, preferably at least 95%, preferably at least 97%.

67. The process of any of paragraphs 43-66, wherein the glucoamylase present and/or added in liquefaction has a pH stability at pH 5.0 of at least at least 80%, at least 85%, at least 90%.

68. The process of any of paragraphs 43-67, wherein the glucoamylase present and/or added in liquefaction step i) is derived from a strain of the genus *Penicillium*, especially a strain of *Penicillium oxalicum* disclosed as SEQ ID NO: 2 in WO 2011/127802 or SEQ ID NOs: 9 or 14 herein.

69. The process of paragraph 43-68, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

70. The process of any of paragraphs 43-69, wherein the glucoamylase is a variant of the *Penicillium oxalicum* glucoamylase shown in SEQ ID NO: 2 in WO 2011/127802 having a K79V substitution (using the mature sequence shown in SEQ ID NO: 14 herein for numbering), such as a variant disclosed in WO 2013/053801.

71. The process of any of paragraph 43-70, wherein the *Penicillium oxalicum* glucoamylase has a K79V substitution (using SEQ ID NO: 14 for numbering) and further one of the following:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

72. The process of any of paragraphs 43-71, wherein the glucoamylase present and/or added in liquefaction is the *Penicillium oxalicum* glucoamylase has a K79V substitution (using SEQ ID NO: 14 herein for numbering) and further one of the following:
P11F+T65A+Q327F;
P2N+P4S+P11F+T65A+Q327F (using SEQ ID NO: 14 herein for numbering).

73. The process of any of paragraphs 43-72, wherein the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 14 herein.

74. The process of any of paragraphs 1-73, further wherein a pullulanase is present during liquefaction and/or saccharification.

75. The process of any of paragraphs 1-74, comprising the steps of:
i) liquefying the starch-containing material at a temperature above the initial gelatinization temperature using an alpha-amylase derived from *Bacillus stearothermophilus*;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

76. The process of any of paragraphs 1-74, comprising the steps of:
i) liquefying the starch-containing material at a temperature above the initial gelatinization temperature using:
an alpha-amylase derived from *Bacillus stearothermophilus* comprising a double deletion at positions I181+G182, and optionally a N193F substitution; (using SEQ ID NO: 1 herein for numbering);
ii) saccharifying using a glucoamylase derived from a strain of *Gloephyllum*, such as *Gloephyllum serpiarium* or *Gloephyllum trabeum*.
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

77. The process of any of paragraphs 1-76, comprising the steps of:
i) liquefying the starch-containing material at a temperature above the initial gelatinization temperature using:
an alpha-amylase derived from *Bacillus stearothermophilus*;
a protease having a thermostability value of more than 20% determined as Relative Activity at 80° C./70° C., preferably derived from *Pyrococcus furiosus* and/or *Thermoascus aurantiacus*; and
optionally a *Penicillium oxalicum* glucoamylase;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

78. A process of paragraphs 1-77, comprising the steps of:
i) liquefying the starch-containing material at a temperature above the initial gelatinization temperature using:
an alpha-amylase, preferably derived from *Bacillus stearothermophilus*, comprising a double deletion at positions I181+G182, and optionally a N193F substitution (using SEQ ID NO: 1 for numbering) and having a T½ (min) at pH 4.5, 85° C., 0.12 mM $CaCl_2$ of at least 10;
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

79. A process of paragraphs 1-78, comprising the steps of:
i) liquefying the starch-containing material at a temperature between 80-90° C.:
an alpha-amylase, preferably derived from *Bacillus stearothermophilus*, having a T % (min) at pH 4.5, 85° C., 0.12 mM $CaCl_2$ of at least 10;
a protease, preferably derived from *Pyrococcus furiosus* and/or *Thermoascus aurantiacus*, having a thermostability value of more than 20% determined as Relative Activity at 80° C./70° C.;
optionally a *Penicillium oxalicum* glucoamylase
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

80. A process of paragraphs 1-79, comprising the steps of:
i) liquefying the starch-containing material at a temperature above the initial gelatinization temperature using:
  an alpha-amylase derived from *Bacillus stearothermophilus* having a double deletion at positions I181+G182, and optional substitution N193F; and optionally further one of the following set of substitutions:
  E129V+K177L+R179E;
  V59A+Q89R+E129V+K177L+R179E+H208Y+K220P+N224L+Q254S;
  V59A+Q89R+E129V+K177L+R179E+Q254S+M284V;
  V59A+E129V+K177L+R179E+Q254S+M284V;
  E129V+K177L+R179E+K220P+N224L+S242Q+Q254S (using SEQ ID NO: 1 herein for numbering);
ii) saccharifying using a glucoamylase, such as one from a strain of *Gloephyllum*, such as a strain of *Gloephyllum serpiarium*;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

81. A process of paragraphs 1-80, comprising the steps of:
i) liquefying the starch-containing material at a temperature above the initial gelatinization temperature using:
  an alpha-amylase derived from *Bacillus stearothermophilus* having a double deletion at positions I181+G182, and optional substitution N193F, and optionally further one of the following set of substitutions:
  E129V+K177L+R179E;
  V59A+Q89R+E129V+K177L+R179E+H208Y+K220P+N224L+Q254S;
  V59A+Q89R+E129V+K177L+R179E+Q254S+M284V;
  V59A+E129V+K177L+R179E+Q254S+M284V;
  E129V+K177L+R179E+K220P+N224L+S242Q+Q254S (using SEQ ID NO: 1 herein for numbering).
  a protease having a thermostability value of more than 20% determined as Relative Activity at 80° C./70° C., preferably derived from *Pyrococcus furiosus* and/or *Thermoascus aurantiacus*; and
  optionally a *Penicillium oxalicum* glucoamylase shown in SEQ ID NO: 14 having substitutions selected from the group of:
  K79V;
  K79V+P11F+T65A+Q327F; or
  K79V+P2N+P4S+P11F+T65A+Q327F; or
  K79V+P11F+D26C+K33C+T65A+Q327F; or
  K79V+P2N+P4S+P11F+T65A+Q327W+E501V+Y504T; or
  K79V+P2N+P4S+P11F+T65A+Q327F+E501V+Y504T; or
  K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

82. A process of paragraphs 1-81, comprising the steps of:
i) liquefying the starch-containing material at a temperature between 80-90° C. using:
  an alpha-amylase derived from *Bacillus stearothermophilus* having a double deletion at positions I181+G182, and optional substitution N193F, and further optionally one of the following set of substitutions:
  E129V+K177L+R179E;
  V59A+Q89R+E129V+K177L+R179E+H208Y+K220P+N224L+Q254S;
  V59A+Q89R+E129V+K177L+R179E+Q254S+M284V;
  V59A+E129V+K177L+R179E+Q254S+M284V;
  E129V+K177L+R179E+K220P+N224L+S242Q+Q254S (using SEQ ID NO: 1 herein for numbering),
  a protease having a thermostability value of more than 20% determined as Relative Activity at 80° C./70° C., preferably derived from *Pyrococcus furiosus* and/or *Thermoascus aurantiacus*;
  a *Penicillium oxalicum* glucoamylase shown in SEQ ID NO: 14 having substitutions selected from the group of:
  K79V;
  K79V+P11F+T65A+Q327F; or
  K79V+P2N+P4S+P11F+T65A+Q327F; or
  K79V+P11F+D26C+K33C+T65A+Q327F; or
  K79V+P2N+P4S+P11F+T65A+Q327W+E501V+Y504T; or
  K79V+P2N+P4S+P11F+T65A+Q327F+E501V+Y504T; or
  K79V+P11F+T65A+Q327W+E501V+Y504T (using SEQ ID NO: 14 for numbering);
ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

83. The process of any of paragraphs 1-82, comprising the steps of:
i) liquefying the starch-containing material at a temperature above the initial gelatinization temperature using:
  an alpha-amylase derived from *Bacillus stearothermophilus* having a double deletion at positions I181+G182, and optional substitution N193F (using SEQ ID NO: 1 herein for numbering);
  a protease having a thermostability value of more than 20% determined as Relative Activity at 80° C./70° C., preferably derived from *Pyrococcus furiosus* and/or *Thermoascus aurantiacus*; and
  optionally a pullulanase;
  a *Penicillium oxalicum* glucoamylase having a K79V substitution (using SEQ ID NO: 14 herein for numbering);
ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

84. A process of paragraphs 1-63, comprising the steps of:
i) liquefying the starch-containing material at a temperature above the initial gelatinization temperature using:

an alpha-amylase, preferably derived from *Bacillus stearothermophilus*, having a T % (min) at pH 4.5, 85° C., 0.12 mM CaCl₂ of at least 10;
between 0.5 and 10 micro grams *Pyrococcus furiosus* protease per g DS;

ii) saccharifying using a glucoamylase selected from the group of glucoamylase derived from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloephyllum*, such as *G. serpiarium* or *G. trabeum*, or a strain of the *Nigrofomes*;

iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

85. A process of paragraphs 1-84, comprising the steps of:
i) liquefying the starch-containing material at a temperature between 80-90° C. using:
an alpha-amylase, preferably derived from *Bacillus stearothermophilus* having a double deletion at positions I181+G182, and optional substitution N193F and having a T % (min) at pH 4.5, 85° C., 0.12 mM CaCl₂ of at least 10;
between 0.5 and 10 micro grams *Pyrococcus furiosus* protease per g DS;
optionally a pullulanase;
a *Penicillium oxalicum* glucoamylase;

ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

86. A process of paragraphs 1-85, comprising the steps of:
i) liquefying the starch-containing material at a temperature a temperature between 80-90° C. using;
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V:
V59A+E129V+K177L+R179E+Q254S+M284V
E129V+K177L+R179E+K220P+N224L+S242Q+Q254S
(using SEQ ID NO: 1 herein for numbering);
between 0.5 and 10 micro grams *Pyrococcus furiosus* protease per g DS; and
optionally a pullulanase;
a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);

ii) saccharifying using a glucoamylase;
iii) fermenting using a fermenting organism;
wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

87. A process of paragraphs 1-86, comprising the steps of:
i) liquefying the starch-containing material at a temperature between 80-90° C. using:
an alpha-amylase derived from *Bacillus stearothermophilus* having a double deletion I181+G182 and optional substitution N193F; and further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V;
E129V+K177L+R179E+K220P+N224L+S242Q+Q254S
(using SEQ ID NO: 1 herein for numbering).
a protease having a thermostability value of more than 20% determined as Relative Activity at 80° C./70° C., preferably derived from *Pyrococcus furiosus* and/or *Thermoascus aurantiacus*; and
optionally a pullulanase;
a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);

ii) saccharifying using a glucoamylase selected from the group of glucoamylase derived from a strain of *Aspergillus*; or a strain of *Trichoderma*; a strain of *Talaromyces*, a strain of *Pycnoporus*; a strain of *Gloephyllum*; and a strain of the *Nigrofomes*;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

88. A process of any of paragraphs 1-87, comprising the steps of:
i) liquefying the starch-containing material at a temperature between 80-90° C. at a pH between 5.0 and 6.5 using:
an alpha-amylase derived from *Bacillus stearothermophilus* having a double deletion I181+G182 and optional substitution N193F; and optionally further one of the following set of substitutions:

E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V;
E129V+K177L+R179E+K220P+N224L+S242Q+Q254S
(using SEQ ID NO: 1 herein for numbering);
a protease derived from *Pyrococcus furiosus*, preferably the one shown in SEQ ID NO: 13 herein;
a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

89. The process of any of paragraphs 1-88, wherein a cellulolytic composition is present in saccharification, fermentation or simultaneous saccharification and fermentation (SSF).

90. The process of any of paragraphs 1-89, wherein the fermentin organism strain has properties that are about the same as that of *Saccharomyces cerevisiae* MBG4851, or a derivative of *Saccharomyces* strain V14/004037 having the defining characteristics of strain V14/004037, as it provides an increase in ethanol yield compared to Ethanol Red™ under the same process conditions.

91. The process of any of paragraphs 1-90, wherein the fermenting organism strain has properties that are about the same as that of *Saccharomyces cerevisiae* MBG4851, or a derivative of *Saccharomyces* strain V14/004037 having defining characteristics of strain V14/004037, as it provides an increase in ethanol yield compared to Ethanol Red™ (ER) under the same conditions where no urea is present and/or added in simultaneous saccharification and fermentation (SSF).

92. The process of any of paragraphs 1-91, wherein the fermenting organism strain having properties that are about the same as that of *Saccharomyces cerevisiae* MBG4851 or a derivative of *Saccharomyces* strain V14/004037 having the defining characteristics of strain V14/004037, as it produces reduced levels of lactic acid compared to Ethanol Red™ under the same process conditions.

93. The process of any of paragraphs 1-92, wherein the fermenting organism strain having properties that are about the same as that of *Saccharomyces cerevisiae* MBG4851 or a derivative of *Saccharomyces* strain V14/004037 having the defining characteristics of strain V14/004037, as it produces reduced levels of glycerol compared to Ethanol Red™ under the same process conditions.

94. The process of any of paragraphs 1-93, wherein the fermenting organism strain having properties that are about the same as that of *Saccharomyces cerevisiae* MBG4851 or a derivative of *Saccharomyces* strain V14/004037 having the defining characteristics of strain V14/004037, as it has faster fermentation kinetics compared to Ethanol Red™ under the same process conditions.

95. The process of any of paragraphs 1-94, wherein the fermenting organism strain having properties that are about the same as that of *Saccharomyces cerevisiae* MBG4851 or a derivative of *Saccharomyces* strain V14/004037 having the defining characteristics of strain V14/004037, as it reduces the level of acetaldehyde in fermentation compared to Ethanol Red™ under the same process condition.

96. The process of any of paragraphs 1-95, wherein the fermenting organism strain having properties that are about the same as that of *Saccharomyces cerevisiae* MBG4851 or a derivative of *Saccharomyces* strain V14/004037 having the defining characteristics of strain V14/004037, as it increases the oil recovery level compared to Ethanol Red™ under the same process conditions 97. The process of any of paragraphs 1-96, wherein the fermenting organism strain having properties that are about the same as that of *Saccharomyces cerevisiae* MBG4851, or a derivative of *Saccharomyces* strain V14/004037 having defining characteristics of strain V14/004037, has one or more, such as all, of the following properties and defining characteristics:
  increases ethanol yield compared to Ethanol Red™ under the same process conditions;
  produces reduced levels of lactic acid compared to Ethanol Red™ under the same process conditions;
  produces reduced levels of glycerol compared to Ethanol Red™ under the same process conditions;
  reduces the level of acetaldehyde in fermentation compared to Ethanol Red™ under the same process condition;
  increases the oil recovery level compared to Ethanol Red™ under the same process conditions;
  has faster fermentation kinetics compared to Ethanol Red™ under the same process conditions.

98. The process of any of paragraphs 1-97, wherein the fermenting organism is a non-recombinant *Saccharomyces* strain, preferably non-recombinant *Saccharomyces cerevisiae* strain.

99. The process of any of paragraphs 1-98, wherein the fermenting organism strain is a non-recombinant *Saccharomyces* strain preferably non-recombinant *Saccharomyces cerevisiae* strain produced using the method described and concerned in U.S. Pat. No. 8,257,959-BB.

100. The process of any of paragraphs 1-99, wherein the wherein the fermenting organism strain having properties that are about the same as that of *Saccharomyces cerevisiae* MBG4851, or a derivative of *Saccharomyces* strain V14/004037 having defining characteristics of strain V14/004037, provides an ethanol yield boost over Ethanol Red™ (ER) of more than 1.0% at 0 ppm urea and at a Pfu dose of 3 µg EP/gDS, such as more than 1.5% at 0 ppm urea and at a Protease Pfu dose of 1.5 µg EP/gDS, such as more than 4.0% at 0 ppm urea and at a Protease Pfu dose of 0.0385 µg EP/gDS when determined using the process set-up and conditions used in Example 19.

101. The process of any of paragraphs 1-100, wherein the fermenting organism strain having properties that are about the same as that of *Saccharomyces cerevisiae* MBG4851, or a derivative of *Saccharomyces* strain V14/004037 having defining characteristics of strain V14/004037, provides an ethanol yield boost of more than 1.0% at urea levels of 300 ppm, such as more than 3.0% at urea levels of 150 ppm, such as more than 10.0% at urea levels of 0 ppm over Ethanol Red™ (ER) when determined using the process set-up and conditions used in Example 21.

102. The process of any of paragraphs 1-101, wherein the fermenting organism strain having properties that are about the same as that of *Saccharomyces cerevisiae* MBG4851, or a derivative of *Saccharomyces* strain V14/004037 having defining characteristics of strain V14/004037, provides a reduction in lactic acid in a 54 hours fermentation of more than 50% at urea levels of 0 ppm and at a Protease Pfu dose of 0.0385 µg/g DS, such as more than 50% at urea levels of 0 ppm and a Pfu dose of 3 µg/gDS over Ethanol Red™ (ER) when determined using the process set-up and conditions used in Example 23.

103. The process of any of paragraphs 1-102, wherein the fermenting organism strain having properties that are about the same as that of *Saccharomyces cerevisiae* MBG4851, or a derivative of *Saccharomyces* strain V14/004037 having the defining characteristics of strain V14/004037, provides a reduction in glycerol levels in a 60 hours fermentation of more than 2.0% such as more than 3.0%, such as more than 4.0% over Ethanol Red™ (ER) when determined using the process set-up and conditions used in Example 34.

104. The process of any of paragraphs 1-103, wherein the fermenting organism strain having properties that are about the same as that of *Saccharomyces cerevisiae* MBG4851, or a derivative of *Saccharomyces* strain V14/004037 having the defining characteristics of strain V14/004037, provides a reduction in the acetaldehyde level, in a 54 hours fermentation, of more than 30%, such as more than 40%, such as more than 50% over Ethanol Red™ (ER) when determined using the process set-up and conditions used in Example 39.

105. A process for producing ethanol from starch-containing material comprising the steps of:
i) liquefying the starch-containing material at a temperature above the initial gelatinization temperature using an alpha-amylase derived from *Bacillus stearothermophilus*;
ii) saccharifying using a glucoamylase;
iii) fermenting using a fermenting organism;
wherein the fermenting organism has one or more, such as all, of the following properties and defining characteristics:
   increases ethanol yield compared to Ethanol Red™ (ER) under the same process conditions;
   produces reduced levels of lactic acid compared to Ethanol Red™ under the same process conditions;
   produces reduced levels of glycerol compared to Ethanol Red™ under the same process conditions;
   reduces the level of acetaldehyde in fermentation compared to Ethanol Red™ under the same process condition;
   increases the oil recovery level compared to Ethanol Red™ under the same process conditions;
   has faster fermentation kinetics compared to Ethanol Red™ under the same process conditions.

106. The process of paragraph 103, wherein the fermenting organism is a *Saccharomyces cerevisiae* yeast.

107. The process of paragraphs 105 or 106, wherein the fermenting organism is a non-recombinant *Saccharomyces cerevisiae* yeast.

108. A process of any of paragraphs 1-107, comprising the steps of:
i) liquefying the starch-containing material at a temperature between 80-90° C. at a pH between 5.0 and 6.5 using:
   an alpha-amylase derived from *Bacillus stearothermophilus* having a double deletion I181+G182 and optional substitution N193F; and optionally further one of the following set of substitutions:
      E129V+K177L+R179E;
      V59A+Q89R+E129V+K177L+R179E+H208Y+K220P+N224L+Q254S;
      V59A+Q89R+E129V+K177L+R179E+Q254S+M284V;
      V59A+E129V+K177L+R179E+Q254S+M284V;
      E129V+K177L+R179E+K220P+N224L+S242Q+Q254S
         (using SEQ ID NO: 1 herein for numbering).
   a protease derived from *Pyrococcus furiosus*, preferably the one shown in SEQ ID NO: 13 herein present and/or added in a dosage of 1-5 micro gram protease per gram DS, such as around 1.5 or 3 micro gram protease per gram DS;
   a *Penicillium oxalicum* glucoamylase shown in SEQ ID NO: 14 having substitutions selected from the group of:
      K79V;
      K79V+P11F+T65A+Q327F; or
      K79V+P2N+P4S+P11F+T65A+Q327F; or
      K79V+P11F+D26C+K33C+T65A+Q327F; or
      K79V+P2N+P4S+P11F+T65A+Q327W+E501V+Y504T; or
      K79V+P2N+P4S+P11F+T65A+Q327F+E501V+Y504T; or
      K79V+P11F+T65A+Q327W+E501V+Y504T (using SEQ ID NO: 14 for numbering);
ii) saccharifying using a glucoamylase;
iii) fermenting using a fermenting organism; wherein the fermenting organism is *Saccharomyces cerevisiae* MBG4851 (deposited under Accession No. V14/004037 at National Measurement Institute, Victoria, Australia) or a strain having properties that are about the same as that of *Saccharomyces cerevisiae* MBG4851 or a derivative of *Saccharomyces* strain V14/004037 having the defining characteristics of strain V14/004037.

109. The process of any of paragraphs 105-108, wherein the fermenting organism is *Saccharomyces cerevisiae* MBG4851 (deposited under Accession No. V14/004037 at National Measurement Institute, Victoria, Australia), or the fermenting organism strain has properties that are about the same as that of *Saccharomyces cerevisiae* MBG4851, or a derivative of *Saccharomyces* strain V14/004037 having the defining characteristics of strain V14/004037.

110. A process of recovering oil from a fermentation product production process comprising the steps of:
i) liquefying starch-containing material at a temperature above the initial gelatinization temperature using an alpha-amylase;
ii) saccharifying using a glucoamylase;
iii fermenting using a fermenting organism.
iv) recovering the fermentation product to form whole stillage;
v) separating the whole stillage into thin stillage and wet cake;
vi) optionally concentrating the thin stillage into syrup;
wherein oil is recovered/extracted downstream from fermentation step iii) and wherein the fermenting organism is *Saccharomyces cerevisiae* MBG4851 (deposited under Accession No. V14/004037 at National Measurement Institute, Victoria, Australia) or a fermenting organism strain having properties that are about the same as that of *Saccharomyces cerevisiae* MBG4851 or a derivative of *Saccharomyces* strain V14/004037 having defining characteristics of strain V14/004037.

111. The process of claim 110, wherein a protease is present or added in saccharification and/or fermentation or simultaneous saccharification and fermentation (SSF).

112. A *Saccharomyces* yeast strain deposited under the Budapest Treaty and having NMI accession no. V14/004037

(*Saccharomyces cerevisiae* MBG4851) or a strain having properties that are about the same as that of *Saccharomyces cerevisiae* MBG4851 or a derivative of strain V14/004037 which exhibits one or more defining characteristics of strain V14/004037.

113. The strain of paragraph 112, wherein the strain is strain V14/004037 (MBG4851).

114. A method of producing a derivative of strain V14/004037 which exhibits the defining characteristics of strain V14/004037, comprising:
  (a) providing:
    (i) a first yeast strain; and
    (ii) a second yeast strain, wherein the second yeast strain is strain V14/004037 or a derivative of strain V14/004037;
  (b) culturing the first yeast strain and the second yeast strain under conditions which permit combining of DNA between the first and second yeast strains;
  (c) screening or selecting for a derivative of strain V14/004037.

115. The method of paragraph 114, wherein step (c) comprises screening or selecting for a hybrid strain which exhibits one or more defining characteristic of strain V14/004037.

116. The method of paragraph 114, comprising the further step of:
  (d) repeating steps (b) and (c) with the screened or selected strain from step (c) as the first and/or second strain, until a derivative is obtained which exhibits the defining characteristics of strain V14/004037.

117. The method of paragraph 114 or 115, wherein the culturing step (b) comprises:
  (i) sporulating the first yeast strain and the second yeast strain;
  (ii) hybridizing germinated spores produced by the first yeast strain with germinated spores produced by the second yeast strain.

118. A *Saccharomyces* strain produced by the method of paragraph 114.

119. A method of producing ethanol, comprising incubating a strain of paragraph 112 or 118 with a substrate comprising a fermentable sugar under conditions which permit fermentation of the fermentable sugar to produce ethanol.

120. Use of a strain of paragraph 112 or 118 in the production of ethanol.

121. A method of producing distiller's grain, comprising:
  (a) incubating a *Saccharomyces* strain of paragraphs 112 or 118 with a substrate comprising fermentable sugar under conditions which allow fermentation of the fermentable sugar to produce ethanol and distiller's grains;
  (b) isolating the distiller's grains.

122. Distiller's grain produced by the method of paragraph 121.

123. Use of a strain of paragraph 112 or 118 in the production of distiller's grains.

124. Use of strain V14/004037 (*Saccharomyces cerevisiae* MBG4851) in the production of a *Saccharomyces* strain having properties that are about the same as that of *Saccharomyces cerevisiae* MBG4851 or which exhibits one or more defining characteristics of strain V14/004037.

125. Use of strain V14/004037 (*Saccharomyces cerevisiae* MBG4851) or a strain having properties that are about the same as that of *Saccharomyces cerevisiae* MBG4851 or a derivative of strain V14/004037 in a process according to any of paragraphs 1-111.

126. Use of strain V14/004037 (*Saccharomyces cerevisiae* MBG4851) or a derivative of strain V14/004037 for reducing the level of acetaldehyde in fermentation compared to Ethanol Red™ under the same process condition.

127. The use according to paragraph 126, wherein the mash in fermentation has been subjected to alpha-amylase and from 0.5-50 micro gram protease per gram DS, such as 1-5 micro gram protease per gram DS such as around 1.5 or 3 micro gram protease per gram DS.

128. The use according to paragraph 127, wherein the protease is a bacterial protease.

129. The use according to claims 127-128, wherein the protease is derived from a strain of the bacterium *Pyrococcus*, such as a strain of *Pyrococcus furiosus* (pfu protease), such as or SEQ ID NO: 13 herein.

130. The use according to paragraph 129, wherein the protease is the one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 13 herein.

131. The use according to paragraphs 125-128, wherein the alpha-amylase is of bacterial origin, such as from the genus *Bacillus*, such as a strain of *Bacillus stearothermophilus*, in particular a variant of a *Bacillus stearothermophilus* alpha-amylase, such as the one shown in SEQ ID NO: 1 herein.

132. The use according to paragraph 130, wherein the *Bacillus stearothermophilus* alpha-amylase variant is selected from the group with the following mutations:
  I181*+G182*+N193F+E129V+K177L+R179E;
  I181*+G182*+N193F+V59A+Q89R+E129V+K177L+R179E+H208Y+K220P+N224L+Q254S;
  I181*+G182*+N193F+V59A+Q89R+E129V+K177L+R179E+Q254S+M284V;
  I181*+G182*+N193F+V59A+E129V+K177L+R179E+Q254S+M284V; and
  I181*+G182*+N193F+E129V+K177L+R179E+K220P+N224L+S242Q+Q254S (using SEQ ID NO: 1 for numbering).

133. Th use according to any of paragraphs 125-132, where the mash to be fermented has been subjected to alpha-amylase, glucoamylase and from 0.5-50 micro gram protease per gram DS, such as 1-5 micro gram protease per gram DS such as around 1.5 or 3 micro gram protease per gram DS.

134. The use according to paragraph 133, wherein the glucoamylase is derived from a strain of the genus *Penicillium*, especially a strain of *Penicillium oxalicum* disclosed in SEQ ID NOs: 9 or 14 herein.

135. The use according to 134, wherein the glucoamylase is a variant of the *Penicillium oxalicum* glucoamylase having a K79V substitution (using the mature sequence shown in SEQ ID NO: 14 for numbering).

136. The use according to paragraph 135, wherein the *Penicillium oxalicum* glucoamylase has a K79V substitution (using SEQ ID NO: 14 for numbering) and further one of the following:
  P11F+T65A+Q327F;
  P2N+P4S+P11F+T65A+Q327F (using SEQ ID NO: 14 for numbering).

137. Use of strain V14/004037 (*Saccharomyces cerevisiae* MBG4851) or a derivative of strain V14/004037 for increasing oil recovery/extraction in an ethanol production process compared to Ethanol Red™ under the same process condition.

138. A composition comprising a *Saccharomyces* yeast strain of any of paragraphs 112 or 118 and one or more naturally occurring and/or non-naturally occurring components.

139. The composition of paragraph 138, wherein the components are selected from the group consisting of: surfactants, emulsifiers, gums, swelling agents, and antioxidants.

140. The composition of paragraphs 138-139, wherein the *Saccharomyces* yeast strain is *Saccharomyces* MBG4851.

141. The composition of paragraphs 138-140, wherein the *Saccharomyces* yeast strain is in a viable form, in particular in dry, cream or compressed form.

The invention claimed is:

1. A *Saccharomyces* yeast strain deposited under the Budapest Treaty and having NMI accession no. V14/004037 (*Saccharomyces cerevisiae* MBG4851).

2. A composition comprising a *Saccharomyces* yeast strain of claim 1, and one or more naturally occurring and/or non-naturally occurring components selected from the group consisting of: surfactants, emulsifiers, gums, swelling agents, and antioxidants.

3. A process for producing ethanol from starch-containing material comprising the steps of:
  i) liquefying the starch-containing material at a temperature above the initial gelatinization temperature using an alpha-amylase;
  ii) saccharifying using a glucoamylase; and
  iii) fermenting using the *Saccharomyces* yeast strain of claim 1.

4. The process of claim 3, wherein 100 to 600 ppm urea is added in saccharification step ii) or fermentation step iii) or added during simultaneous saccharification and fermentation (SSF) of steps ii) and iii).

5. The process of claim 3, wherein a protease is added in saccharification step ii) or fermentation step iii) or added during simultaneous saccharification and fermentation (SSF) of steps ii) and iii).

6. A method of producing ethanol, comprising incubating the yeast strain of claim 1 with a substrate comprising a fermentable sugar under conditions which permit fermentation of the fermentable sugar to produce ethanol.

7. A method of producing distiller's grain, comprising:
  (a) incubating the yeast strain of claim 1 with a substrate comprising fermentable sugar under conditions which allow fermentation of the fermentable sugar to produce ethanol and distiller's grains;
  (b) isolating the distiller's grains.

8. A process of recovering/extracting oil from an ethanol fermentation product production process comprising the steps of:
  i) liquefying starch-containing material at a temperature above the initial gelatinization temperature using an alpha-amylase;
  ii) saccharifying using a glucoamylase;
  iii) fermenting using a fermenting organism;
  iv) recovering the fermentation product to form whole stillage;
  v) separating the whole stillage into thin stillage and wet cake;
  vi) optionally concentrating the thin stillage into syrup;
  wherein oil is recovered/extracted downstream from fermentation step iii) and wherein the fermenting organism is the *Saccharomyces* yeast strain of claim 5.

* * * * *